United States Patent
Kuball et al.

(10) Patent No.: US 11,596,654 B2
(45) Date of Patent: Mar. 7, 2023

(54) HUMAN LEUKOCYTE ANTIGEN RESTRICTED GAMMA DELTA T CELL RECEPTORS AND METHODS OF USE THEREOF

(71) Applicant: Gadeta B.V., Utrecht (NL)

(72) Inventors: Jürgen Herbert Ernst Kuball, Hilversum (NL); Guido Joris Jan Kierkels, Utrecht (NL); Zsolt Sebestyen, Amsterdam (NL)

(73) Assignee: GADETA B.V., Utrecht (NL)

( * ) Notice: Subject to any disclaimer, the term of this patent is extended or adjusted under 35 U.S.C. 154(b) by 751 days.

(21) Appl. No.: 16/215,452

(22) Filed: Dec. 10, 2018

(65) Prior Publication Data

US 2019/0169260 A1    Jun. 6, 2019

Related U.S. Application Data

(63) Continuation of application No. PCT/EP2017/064323, filed on Jun. 12, 2017.

(30) Foreign Application Priority Data

Jun. 10, 2016  (EP) ..................... 16173970
Jun. 10, 2016  (EP) ..................... 16173986

(51) Int. Cl.
| | | |
|---|---|---|
| A61K 35/17 | (2015.01) | |
| C07K 16/28 | (2006.01) | |
| C07K 16/30 | (2006.01) | |
| C12N 5/0783 | (2010.01) | |
| G01N 33/569 | (2006.01) | |
| C07K 14/725 | (2006.01) | |
| A61P 35/00 | (2006.01) | |
| C12N 15/62 | (2006.01) | |
| C12N 15/90 | (2006.01) | |
| C12Q 1/6809 | (2018.01) | |
| A61K 38/00 | (2006.01) | |

(52) U.S. Cl.
CPC ............. *A61K 35/17* (2013.01); *A61P 35/00* (2018.01); *C07K 14/7051* (2013.01); *C07K 16/2833* (2013.01); *C07K 16/30* (2013.01); *C12N 5/0636* (2013.01); *C12N 5/0638* (2013.01); *C12N 15/62* (2013.01); *C12N 15/907* (2013.01); *C12Q 1/6809* (2013.01); *G01N 33/56977* (2013.01); *A61K 38/00* (2013.01); *C07K 2317/32* (2013.01); *G01N 2800/7028* (2013.01)

(58) Field of Classification Search
None
See application file for complete search history.

(56) References Cited

U.S. PATENT DOCUMENTS

| | | |
|---|---|---|
| 5,260,223 A | 11/1993 | Brenner et al. |
| 5,723,309 A | 3/1998 | Bonneville |
| 8,999,715 B2 | 4/2015 | Bonini et al. |
| 9,891,211 B2 | 2/2018 | Kuball et al. |
| 2002/0011914 A1 | 1/2002 | Ikeura et al. |
| 2002/0119149 A1 | 8/2002 | Jakobsen et al. |
| 2002/0142389 A1 | 10/2002 | Jakobsen et al. |
| 2006/0093613 A1 | 5/2006 | Jakobsen et al. |
| 2006/0155115 A1 | 7/2006 | Jakobsen et al. |
| 2007/0036812 A1 | 2/2007 | Sato et al. |
| 2008/0131415 A1 | 6/2008 | Riddell et al. |
| 2009/0105133 A1 | 4/2009 | Boulter |
| 2010/0151467 A1 | 6/2010 | Wohlgemuth et al. |
| 2014/0120622 A1 | 5/2014 | Gregory et al. |
| 2014/0219975 A1 | 8/2014 | June et al. |
| 2014/0308250 A1 | 10/2014 | Handgretinger et al. |
| 2014/0356398 A1 | 12/2014 | Riddell et al. |
| 2015/0017137 A1 | 1/2015 | Spencer et al. |
| 2015/0050670 A1 | 2/2015 | Kuball et al. |
| 2015/0306142 A1 | 10/2015 | Bonini et al. |
| 2015/0344844 A1 | 12/2015 | Better et al. |
| 2015/0353643 A1 | 12/2015 | Olive et al. |
| 2017/0174741 A1 | 6/2017 | Kuball et al. |
| 2018/0188234 A1 | 7/2018 | Kuball et al. |

FOREIGN PATENT DOCUMENTS

| | | |
|---|---|---|
| CN | 1379041 A | 11/2002 |
| CN | 101155829 A | 4/2008 |
| CN | 102453701 A | 5/2012 |
| CN | 102532269 A | 7/2012 |
| CN | 102532269 B | 7/2014 |
| CN | 105296431 A | 2/2016 |
| EP | 1080193 A2 | 3/2001 |
| EP | 1066380 B1 | 11/2001 |
| EP | 2099902 A1 | 9/2009 |
| EP | 1956080 B1 | 9/2011 |
| EP | 2710123 A2 | 3/2014 |
| EP | 2686417 B1 | 6/2016 |
| EP | 3102609 A2 | 12/2016 |
| EP | 3144388 | 3/2017 |
| WO | WO-9412648 A2 | 6/1994 |

(Continued)

OTHER PUBLICATIONS

Xu et al. (PNAS, 108(6): 2414-2419, 2011).*

(Continued)

*Primary Examiner* — Nelson B Moseley, II

(74) *Attorney, Agent, or Firm* — Polsinelli PC

(57) ABSTRACT

Disclosed herein are compositions and methods of treating a subject with cancer. The compositions and methods utilize immunoresponsive cells to effect killing of tumor cells.

9 Claims, 23 Drawing Sheets

Specification includes a Sequence Listing.

(56) References Cited

FOREIGN PATENT DOCUMENTS

| | | |
|---|---|---|
| WO | WO-9958557 A2 | 11/1999 |
| WO | WO9960120 A2 | 11/1999 |
| WO | WO-0224718 A1 | 3/2002 |
| WO | WO-03060097 A2 | 7/2003 |
| WO | WO-2004016225 A2 | 2/2004 |
| WO | WO-2005016962 A2 | 2/2005 |
| WO | WO-2005019258 A2 | 3/2005 |
| WO | WO-2005051988 A3 | 7/2005 |
| WO | WO-2006056733 A1 | 6/2006 |
| WO | WO-2006026051 A3 | 7/2007 |
| WO | WO-2007034489 A3 | 12/2007 |
| WO | WO-2009136874 A1 | 11/2009 |
| WO | WO2010058023 A1 | 5/2010 |
| WO | WO-2010087335 A1 | 8/2010 |
| WO | WO-2013147606 A1 | 10/2013 |
| WO | WO-2014179202 A1 | 11/2014 |
| WO | WO-2015063069 A1 | 5/2015 |
| WO | WO-2015075939 A1 | 5/2015 |
| WO | WO-2015174439 A1 | 11/2015 |
| WO | WO-2016195086 A1 | 12/2016 |
| WO | WO-2017096239 A1 | 6/2017 |
| WO | WO-2017212072 A1 | 12/2017 |
| WO | WO-2018211115 A1 | 11/2018 |

OTHER PUBLICATIONS

Niemeyer, G., et al., Long-term correction of inhibitor-prone hemophilia B dogs treated with liver-directed AAV2-mediated factor IX gene therapy, Blood. Jan. 22, 2009;113(4):797-806.
Airoldi, I., et al. (2015). gammadelta T-cell reconstitution after HLA-haploidentical hematopoietic transplantation depleted of TCR-alphabeta+/CD19+ lymphocytes. Blood 125: 2349-58.
Altschul, et al. Basic local alignment search tool. J Mol Biol. Oct. 5, 1990;215(3):403-10.
Amado and Chen, Lentiviral vectors—the promise of gene therapy within reach?,1999, Science 285: 674-6.
Anderson, W. French, Human gene therapy, 1998, Nature 392: pp. 25-30.
Anonymous: "EM_STD:BC030554", Dec. 2, 2006 (Dec. 2, 2006), XP055403988, Retrieved from the Internet: URL:http://ibis.internal.epo.org/exam/dbfetch.jsp?id=EM_STD:BC030554 [retrieved on Sep. 5, 2017].
Anonymous: "UP10000480E66", Mar. 23, 2007 (Mar. 23, 2007), XP055403650, Retrieved from the Internet: URL:http://www.uniprot.org/ uniparc/UPI0000480E66 [retrieved on Sep. 4, 2017].
Anonymous: "UPI0000117293", Mar. 28, 2003 (Mar. 28, 2003), XP055403635, Retrieved from the Internet: URL:http://www.uniprot.org/ uniparc/UPI0000117293 [retrieved on Sep. 4, 2017].
Apparailly, M., et al., Adeno-Associated Virus Psuedotype 5 Vector Improves Gene Transfer in Arthritic Joints, Hum Gene Ther, Apr. 2005; 16(4): 426-34.
Ausubel, et al., (1987) Current Protocols in Molecular Biology.
Bender, C, et al. (2009). Analysis of colorectal cancers for human cytomegalovirus presence. Infect Agent Cancer 4: 6.
Bolotin, DA, et al. (2015), MiXCR: software for comprehensive adaptive immunity profiling. Nat Methods 12: 380-1.
Born, et al., Peptide antigens for gamma/delta T cells. 2011, Cell Mol. Life Sci., 68: 2335-2343.
Bosnes, Vidar et al.: "Recognition of a particular HLA-DQ heterodimer by a human γ/6 T cell clone*",Eur. J. Immunol, Jan. 1, 1990 (Jan. 1, 1990), pp. 1429-1433, XP055406203, Retrieved from the Internet: URL:http://onlinelibrary.wiley.com/store/10.1002/eji.1830200704/asset/1830200704_ftp.pdf? v=1 &t=j7iu67qt&s= 6a5f4ca4b764249f46da541f127c2ef6eb44352a.
Bouchie, A. et al., 2017. Nature Biotechnology's academic spinouts of 2016, Nat Biotechnol 35: 322-33.
Bowness, P. et al., Th17 Cells Expressing KIR3DL2+ and Responsive to HLA-B27 Homodimers Are Increased in Ankylosing Spondylitis, The Journal of Immunology, vol. 186, No. 4, Feb. 15, 2011 (Feb. 15, 2011), pp. 2672-2680, XP55373331, US ISSN: 0022-1767, DOI: 10.4049/jimmunol.1002653.
Brauninger, A., (1999). Identification of common germinal-center B-cell precursors in two patients with both Hodgkin's disease and non-Hodgkin's lymphoma, N Engl J Med 340: 1239-47.
Bukowski, et al., (1998) Crucial Role of TCRgamma Chain Junctional Region in Prenyl Pyrophosphate Antigen Recognition by gamma delta T cells, J. Immunol. 161: 286-293.
Carillo et al. The Multiple Sequence Alignment Problem in Biology. SIAM J. Appl. Math 48(5):907-1082 (1988).
Castella, et al., (2011) V gamma 9 V delta 2 T cell-based immunotherapy in hematological malignancies: from bench to bedside, Cell Mol. Life Sci. 68: 2419-2432.
Chien, Y.H., et al., (2014) gammadelta T Cells: First Line of Defense and Beyond. Annu. Rev. Immunol., vol. 32:121-155.
Coffelt, S.B., (2015). IL-17-producing gammadelta T cells and neutrophils conspire to promote breast cancer metastasis. Nature 522: 345-8.
Colman et al., Effects of amino acid sequence changes on antibody-antigen interactions, Research in Immunology, 1994; 145(1):33-36.
Corrected Notice of Allowability dated Aug. 23, 2016 for U.S. Appl. No. 14/388,675.
Corrected Notice of Allowability dated Dec. 13, 2016 for U.S. Appl. No. 14/388,675.
Couzin-Frankel, J., (2013), Breakthrough of the year 2013. Cancer immunotherapy. Science 342: 1432-3.
Dadi, S., et al., (2016). Cancer Immunosurveillance by Tissue-Resident Innate Lymphoid Cells and Innate-like T Cells. Cell 164: 365-77.
Davey, MS, et al., (2017), Clonal selection in the human Vdelta1 T cell repertoire indicates gammadelta TCR-dependent adaptive immune surveillance. Nat Commun 8: 14760.
David, A. et al., Transient Transgenesis in The Endocrine System: Viral Vectors for Gene Delivery (1999), J. Gen. Virol. 80: 3049-64.
Davis et al. Development of human anti-murine T-cell receptor antibodies in both responding and nonresponding patients enrolled in TCR gene therapy trials. Clin Cancer Res. Dec. 1, 2010;16(23):5852-61.
De Witte, M.A., et al. (2015), Orchestrating an immune response against cancer with engineered immune cells expressing alphabetaTCRs, CARs, and innate immune receptors: an immunological and regulatory challenge. Cancer Immunol Immunother 64: 893-902.
Deniger, D.C., et al., (2014), Clinical applications of gamma delta T cells with multivalent immunity. Front Immunol 5: 636.
Devereux et al., A comprehensive set of sequence analysis programs for the VAX. Nucleic Acids Res. Jan. 11, 1984;12(1 Pt 1):387-95.
Ding, Y., et al., (2015). Characteristics of the Vdelta2 CDR3 Sequence of Peripheral gammadelta T Cells in Patients with Pulmonary Tuberculosis and Identification of a New Tuberculosis-Related Antigen Peptide. Clin Vaccine Immunol 22: 761-8.
Elmaagacli, A.H., et al., (2016), Cytomegalovirus replication reduces the relapse incidence in patients with acute myeloid leukemia, Blood 128: 456-9.
EP17203843.2 European Search Report dated Mar. 9, 2018.
Federico, Maurizio, Lentiviruses as gene delivery vectors, (1999), Curr. Opin. Biotechnol.10: 448-53.
Fisch, P. et al. Recognition By Human V-Gamma-9-V-Delta-2 T Cells Of A GroEL Homolog on Daudi Burkitt's Lymphoma Cell. vol. 250, No. 4985, pp. 1269-1273, 1990.
Fooksman, David et al., Clustering Class I MHC Modulates Sensitivity of T-cell Recognition 1,2, Jun. 1, 2006 (Jun. 1, 2006), XP55406164, Retrieved from the Internet: URL:https://http://www.ncbi.nlm.nih.gov/pmc/articles/PMC1524854/pdf/nihms11101.pdf [retrieved on Sep. 13, 2017].
Gentles, A.J., et al., (2015). The prognostic landscape of genes and infiltrating immune cells across human cancers. Nat Med 21: 938-45.
Gomes, A., et al.,. Targeting gamma delta T Lymphocytes for Cancer Immunotherapy: From Novel Mechanistic Insight to Clinical Application. 2010, Cancer Res. 70: 10024-10027.

(56) References Cited

OTHER PUBLICATIONS

Grunder C., et al., 2012. gamma9 and delta2CDR3 domains regulate functional avidity of T cells harboring gamma9delta2TCRs. Blood 120: 5153-62.
Grunder, et al. Individual T-Cell Receptors of γ9δ2T-Cells Mediate Differential Anti-Tumor-reactivity. Abstract Only. From Blood 2011; 118:4312.
Harly C., Guillaume Y, (2012), Key implication of CD277/butyrophilin-3 (BTN3A) in cellular stress sensing by a major human gammadelta T-cell subset. Blood 120: 2269-79.
Hentikoff and Hentikoff, (1992), Amino acid substitution matrices from protein blocks, Proc. Natl. Acad. Sci. USA. 89:10915-10919.
Hildalgo, J.V., et al., (2014). Histological Analysis of gammadelta T Lymphocytes Infiltrating Human Triple-Negative Breast Carcinomas. Front Immunol 5: 632.
Ho, S.N., et al., Site-directed mutagenesis by overlap extension using the polymerase chain reaction. Gene, 1989. 77(1): p. 51-9.
Holtmeier, W., et al. (1995), The delta T cell receptor repertoire in human colon and peripheral blood is oligoclonal irrespective of V region usage, J Clin Invest 96: 1108-17.
InMunoGeneTics information system (http://www.imgt.org/IMGTScientificChart/Nomenclature/IMGT- 20 FRCDRdefinition.html).
International Preliminary Report on Patentability dated May 23, 2017 for International PCT Patent Application No. PCT/EP2015/077286.
International Search Report dated Jan. 27, 2016 for International PCT Patent Application No. PCT/EP2015/077286.
International Search Report for PCT/NL2013/050235 dated Oct. 9, 2013.
Kabelitz, D., et al., (2007) Perspectives of T Cells in Tumor Immunology. Cancer Research, vol. 67, No. 1, pp. 5-8.
Kabelitz, D., et al., Potential Of Human [gamma][delta] T Lymphocytes For Immunotherapy Of Cancer. International Journal of Cancer, 112:727-732 (2004).
Kay et al., Viral vectors for gene therapy: the art of the turning infectious agents into vehicles of therapeutics, (2001), Nat. Med. 7: 33-40.
Kershaw et al. Gene-engineered T cells for cancer therapy. Nat Rev Cancer 13(8):525-541 (2013).
Kim, S.K., et al., (2005), Private specificities of CD8 T cell responses control patterns of heterologous immunity, J Exp Med 201: 523-33.
Kuball, et al. Increasing functional avidity of TCR-redirected T cells by removing defined N-glycosylation sites in the TCR constant domain. J Exp Med. Feb. 16, 2009;206(2):463-75.
Kuball, et al. Multipotent Vδ2-negative γδT-cells after CMV-reactivation in allogeneic stem cell transplantation (162.36). Abstract Only. From J Immunol May 1, 2012, 188 (1 Supplement) 162.36.
Kuball, J, et al, 2007, Facilitating matched pairing and expression of TCR chains introduced into human T cells. Blood 109: 2331-8.
Li, B., et al. (2016), Landscape of tumor-infiltrating T cell repertoire of human cancers. Nat. Genetics 48,725-732.
Lim, W.A., (2017). The Principles of Engineering Immune Cells to Treat Cancer. Cell 168: 724-40.
Loi, S., et al., (2016), RAS/MAPK Activation Is Associated with Reduced Tumor-Infiltrating Lymphocytes in Triple-Negative Breast Cancer: Therapeutic Cooperation Between MEK and PD-1/PD-L1 Immune Checkpoint Inhibitors. Clin Cancer Res 22: 1499-509.
M. Ferez et al: "Cognate Peptide-MHC Complexes Are Expressed as Tightly Apposed Nanoclusters in Virus-Infected Cells To Allow TCR Crosslinking", The Journal of Immunology, vol. 192, No. 1, Dec. 4, 2013 (Dec. 4, 2013), pp. 52-58, XP55406156, US ISSN: 0022-1767, DOI: 10.4049/jimmunol.1301224.
Mamedov, I.Z., et al. (2013), Preparing unbiased T-cell receptor and antibody cDNA libraries for the deep next generation sequencing profiling, Front Immunol 4: 456.
Mami-Chouaib, F. et al: "Further evidence for a gamma/delta T cell receptor-mediated TCT.1/CD48 recognition", The Journal of Immunology, Nov. 1, 1991 (Nov. 1, 1991), pp. 2864-2867, XP055403236, United States Retrieved from the Internet: U RL:http://www.ji mmunol.org/content/147/9/2864.full-text.pdf.
Mandel, R.J.,et al. Clinical trials in neurological disorders using AAV vectors: promises and Challenges (2004), CurrOpin Mol Ther. 6(5):482-90.
Marcu-Malina et al. Re-targeting T-cells against cancer by gene-transfer of tumor-reactive receptors. 2009, Expert Opin. Biol. Ther. 9: 579-591.
MARCU-MALINA et al. Redirecting alpha betaT cells against cancer cells by transfer of a broadly tumor-reactive gamma deltaT-cell receptor. 2011, Blood 118: 50-59.
Marin, M. et al., (1997) Towards efficient cell targeting by recombinant retroviruses, Mol. Med. Today 3: 396-403.
Martin, K.R.G., et al., (2004), Gene therapy for optic nerve disease, , Eye 18(11):1049-55.
Meeh, P.F., (2006), Characterization of the gammadelta T cell response to acute leukemia. Cancer Immunol.Immunother. 55: 1072-80.
Metzger, D., et al., (1988), The human oestrogen receptor functions in yeast, Nature, 334: 31-36.
Miles, JJ, et al., 2005. CTL recognition of a bulged viral peptide involves biased TCR selection. J Immunol 175: 3826-34.
Miyagawa, et al., (2001), Essential Contribution of Germline-Encoded Lysine Residues in J gamma1.2 Segment to the Recognition of Nonpeptide Antigens by Human gamma delta T Cells, J. Immunol. 167: 6773-6779.
Miyazaki, K., (2011) Megawhop cloning: a method of creating random mutagenesis libraries via megaprimer PCR of whole plasmids. Methods Enzymol, 498: p. 399-406.
Moser Bernhard. Tumor-Killing [gamma] [delta]—TCRs take center stage. Blood, vol. 120, No. 26, pp. 5093-5094, Dec. 20, 2012, XP002700185.
Nathwani et al, N Eng' J Med. Dec. 22, 2011;365(25):2357-65.
Needleman, S. et al., (1970), A general method applicable to the search for similarities in the amino acid sequence of two proteins, J. Mol. Biol. 48:443-453.
Nicol, et al., (2011) Clinical evaluation of autologous gamma delta T cell-based immunotherapy for metastatic solid tumors, Br. J. Cancer 105: 778-786.
Nielsen, T.O., (2004), Immunohistochemical and clinical characterization of the basal-like subtype of invasive breast carcinoma. Clin Cancer Res 10: 5367-74.
Notice of Allowance dated Aug. 15, 2016 for U.S. Appl. No. 14/388,675.
Notice of Allowance dated Sep. 15, 2017 for U.S. Appl. No. 14/388,675.
Office Action dated Apr. 26, 2016 for U.S. Appl. No. 14/388,675.
Office Action dated Nov. 20, 2017 for U.S. Appl. No. 15/374,613.
Office Action dated Dec. 29, 2015 for U.S. Appl. No. 14/388,675.
Paul, Fundamental Immunology. 3rd Edition, pp. 292-295, Raven Press, 1993.
Pauza, C. David, et al., Evolution and function of the TCR Vgamma9 chain repertoire: It's good to be public, Cellular Immunology, vol. 296, No. 1, Jul. 1, 2015 (Jul. 1, 2015), pp. 22-30, XP055320697, US ISSN: 0008-8749, DOI: 10.1016/j.cellimm.2015.02.010.
Peng, K.W., et al., (1999), Viral vector targeting, Curr. Opin. Biotechnol. 10: 454-7.
Ravens, S., et al., (2017). Human gammadelta T cells are quickly reconstituted after stem-cell transplantation and show adaptive clonal expansion in response to viral infection. Nature Immunology, 18, 393-401.
Reiser,J. (2000), Production and concentration of pseudotyped HIV-1-based gene transfer vectors, Gene Ther. 7: 910-913.
Roberts, S. et al. (1987), Generation of an antibody with enhanced affinity and specificity for its antigen by protein engineering, Nature 328:731-734.
Rudikoff et al. Single amino acid substitution altering antigen-binding Specificity. PNAS USA 79:1979-1983 (1982).
Russell, W.C., 2000, Update on adenovirus and its vectors, J. Gen. Virol. 81: 2573-604.
Salgado, R, (2015), Tumor-Infiltrating Lymphocytes and Associations With Pathological Complete Response and Event-Free Sur-

(56) References Cited

OTHER PUBLICATIONS vival in HER2-Positive Early-Stage Breast Cancer Treated With Lapatinib and Trastuzumab: A Secondary Analysis of the NeoALTTO Trial. JAMA Oncol 1: 448-54.
Sambrook et al. Molecular Cloning, Second Ed., Cold Spring Harbor Laboratory, Plainview, NY. (1989).
Sandstrom, A, (2014), The intracellular B30.2 domain of butyrophilin 3A1 binds phosphoantigens to mediate activation of human Vgamma9Vdelta2 T cells. Immunity 40: 490-500.
Scheper, W. 2014. Cancer immunotherapy using γδT cells: dealing with diversity. Thesis.
Scheper W., et al., (2013), gammadeltaT cells elicited by CMV reactivation after allo-SCT cross-recognize CMV and leukemia. Leukemia 27: 1328-38.
Scheper, et al. (2012) 477. Multipotent VΔ2-Negative γΔT-Cells after CMV-Reactivation in Allogeneic Stem Cell Transplantation. Molecular Therapy. vol. 20, Supplement 1, p. S185.
Scheper, W., et al., (2014), Cancer Immunotherapy Using gammadeltaT Cells: Dealing with Diversity. Front Immunol 5: 601.
Schneider, C.A., et al., (2012), NIH Image to ImageJ: 25 years of image analysis. Nat Methods 9: 671-5.
Sebestyen, Z. et al., (2016), RhoB Mediates Phosphoantigen Recognition by Vgamma9Vdelta2 T Cell Receptor. Cell Rep 15: 1973-85.
Shugay, M., et al., (2014). Towards error-free profiling of immune repertoires. Nat Methods 11: 653-5.
Simmonelli, Francesca et al, Gene Therapy for Leber's Congenital Amaurosis is Safe and Effective Through 1.5 Years After Vector Administration, American Society of Gene & Cell Ther. Mar. 2010;18(3):643-50. Epub Dec. 1, 2009.
Sittig, S.P, et al.,( 2013), Clonal expansion of renal cell carcinoma-infiltrating T lymphocytes. Oncoimmunology 2: e26014.
Stanislawski et al., Circumventing tolerance to a human MDM2-derived tumor antigen by TCR gene transfer. Nat Immunol. 2001; 2(10): 962-970.
Straetemans T et al. Towards gamma/delta TCR gene therapy: the optimal gamma/delta TCR transgene cassette. Bone Marrow Transplantation, vol. 48 No. Suppl. 2, pp. S72, Apr. 2013, XP002700187.
Straetemans, T., et al., (2015), Untouched GMP-ready purified engineered immune cells to treat cancer. Clin Cancer Res., 21 (17); 3957-68.
Tripodo, et al. Gamma-delta T-cell lymphomas. 2009, Nat. Rev. Clin. Oncol. 6: 707-717.
U.S. Appl. No. 15/374,613 Notice of Allowance dated Jul. 6, 2018.
U.S. Appl. No. 14/388,675 Office Action dated Jul. 20, 2017.
U.S. Appl. No. 15/374,613 Office Action dated Mar. 22, 2018.
U.S. Appl. No. 15/842,784 Office Action dated Jul. 5, 2018.
Uldrich, A.P., et al., (2013) CD1d-lipid antigen recognition by the gammadelta TCR. Nat Immunol 14: 1137-45.
Venturi V., et al., (2008), The molecular basis for public T-cell responses? Nat Rev Immunol 8: 231-8.
Vigna, E. et al., (2000), Lentiviral vectors: excellent tools for experimental gene transfer and promising candidates for gene therapy, J. Gene Med. 2: 308-16.
Voss, et al., (2005), Designing TCR for Cancer Immunotherapy. Adoptive Immunotherapy: Methods and Protocols pp. 229-256. Part of the Methods in Molecular Medicine™ book series, vol. 109.
Walther, W., et al., (2000), Viral Vectors for Gene Transfer, Drugs 60: 249-71.
Wang et al., A comprehensive study of optimal conditions for naked plasmid DNA transfer into skeletal muscle by electroporation, (2005), J Gene Med. Sept. 7(9):12325-45.
Wang, C., et al., (2015), B-cell repertoire responses to varicella-zoster vaccination in human identical twins., Proc Natl Acad Sci U S A 112: 500-5.
Wang, Hong et al. Vgamma2Vdelta2 T Cell Receptor Recognition of Prenyl Pyrophosphates Is Dependent on All CDRs. 2010, J. Immunol. 184: 6209-6222.

Wells, J.A., et al. (1985), Cassette mutagenesis: an efficient method for generation of multiple mutations at defined sites, Gene 34: 315-323.
Willcox, C.R., et al., (2012),.Cytomegalovirus and tumor stress surveillance by binding of a human gammadelta T cell antigen receptor to endothelial protein C receptor, Nat.Immunol. 13: 872-9.
Xi, X. et al. The Recognition Of TCR Protein Antigen Does Not Depend On The Hydrophobic 197 Residue Of CDR3. International Immunology, vol. 22, No. 4, pp. 299-306, Apr. 1, 2010, XP055069895.
Xiang, Z., (2014), Targeted activation of human Vgamma9Vdelta2-T cells controls epstein-barr virus-induced B cell lymphoproliferative disease. Cancer Cell 26: 565-76<a></a>.
Xu, C, et al., (2007), Gammadelta T cells recognize tumor cells via CDR3delta region. Mol Immunol 44: 302-10.
Xu, Chungping et al. γδ T Cells Recognize Tumor Cells Via CDR3δ Region. Molecular Immunology, 2007, vol. 44, pp. 302-310.
Zhao, et al. CDR3δ-grafted γ9δ2T cells mediate effective antitumor reactivity. Cell Mol Immunol. Mar. 2012;9(2):147-54. doi: 10.1038/cmi.2011.28. Epub Sep. 12, 2011.
Morita, Craig T., et al., Nonpeptide antigens, presentation mechanisms, and immunological memory of human Vγ2Vδ2 T cells: discriminating friend from foe through the recognition of prenyl pyrophosphate antigens, Immunological Reviews 2007, vol. 215: 59-76.
Davey et al., Recasting Human Vδ1 Lymphocytes in an Adaptive Role. Davey et al. Willcox Trends Immunol. Jun. 2018; 39(6): 446-459.
European Appl. No. 177339994.2 Office Action dated Feb. 24, 2020.
Grunder C, (2012), gamma9 and delta2CDR3 domains regulate functional avidity of T cells harboring gamma9delta2TCRs. Blood 120: 5153-62.
Grunder C., et al. Gamma 9-and Delta 2-CDR3 Domains Regulate Functional Avidity Of T Cells Harboring c9d2 T Cell Receptors. Journal Of Immunotherapy, vol. 35, No. 9, pp. 723, Nov. 2012.
Halary et al, Shared reactivity of V2neg T cells against cytomegalovirus-infected cells and tumor intestinal epithelial cells, J Exp Med. May 16, 2005; 201(10): 1567-1578.
International Search Report and Written Opinion dated Jul. 8, 2019 for PCT/EP2019/063004 (Published as WO2019/219979)—Applicant: UMC Utrecht Holding B.V.
Lal, Nareej et al., Endothelial protein C receptor is overexpressed in colorectal cancer as a result of amplification and hypomethylation of chromosome 20q, The Journal of Pathology Clinical Research, Jul. 2017; 3(3):155-170.
Melandri et al., The γδ T cell receptor combines innate with adaptive immunity by utilizing spatially distinct regions for agonist-selection and antigen responsiveness, Nat Immunol.. Nat Immunol. Dec. 1, 2019; 19(12): 1352-1365.
Non-Final Office Action dated Feb. 7, 2020, for U.S. Appl. No. 16/275,070.
Willcox et al., Butyrophilin-like 3 Directly Binds a Human Vγ4+T Cell Receptor Using a Modality Distinct from Clonally-Restricted Antigen, Immunity. Nov. 19, 2019; 51(5): 813-825.
XP-002789044 Database Geneseq [Online] Jan. 11, 2018 , Human:BES28452 Database Accession No. BES28452.
XP-002789045 Database Geneseq [online] Feb. 8, 2018, TCR Delta CDR3 peptide VD2#4, retrieved from EBI accession No. GP:BES28452 Database Accession No. BES28452.
Zsolt, Sebestyen et al., RhoB Mediates Phosphoantigen Recognition by V[gamma]9V[delta]2 T Cell Receptor, Cell Reports, vol. 15, No. 9, May 1, 2016.
Non-Final Office Action dated Febr. 7, 2020, for U.S. Appl. No. 16/275,070.
Bernatchez, Chantale et al., Adoptive T Cell Transfer and Cell Therapy as Cancer Immunotherapy (CARS), Abstracts for the 27th Annual Scientific Meeting of the Society for Immunotherapy of Cancer (SITC), J. Immunother, vol. 35, No. 9, Nov. 9, Nov.-Dec. 2012, p. 721-791.
Gonzalez-Villasana, et al., Rac1/Pak1/p38/MMP-2 Axis Regulates Angiogenesis in Ovarian Cancer, Clinical Cancer Research, vol. 21, No. 9, Jan. 16, 2015 (Jan. 16, 2015), pp. 2127-2137, XP055411010, US ISSN: 1078-0432, DOI: 10.1158/1078-0432.CCR-14-2279.

(56) References Cited

OTHER PUBLICATIONS

Huang, M., RhoB facilitates c-Myc turnover by supporting efficient nuclear accumulation of GSK-3, Oncogene, vol. 25, No. 9, Oct. 17, 2005 (Oct. 17, 2005), pp. 1281-1289, XP055496792, London ISSN: 0950-9232, DOI: 10.1038/sj.onc.1209174.

Paterson et al: "Cost-effectiveness of Oral Clodronate Compared with Oral Ibandronate, Intravenous Zoledronate or Intravenous Pamidronate in Breast Cancer Patients", Journal of International Medical Research, vol. 36, No. 3, May 1, 2008 (May 1, 2008), pp. 400-413, XP055496644, GB ISSN: 0300-0605, DOI: 10.1177/147323000803600304.

Straetmans, T. et al., (2013) Towards gamma/delta TCR gene therapy: the optimal gamma/delta TCR transgene cassette. S72-S72, Bone Marrow Transplantation, Apr. 2013, vol. 48 Suppl 2, pp. S72-S72.

XP-002778544 (Database Geneseq [online] May 20, 2004 (May 20, 2004), "Human tumour-associated antigenic target (TAT) polypeptide #22.", XP002778544, retrieved from EBI accession No. GSP:ADL06523 Database accession No. ADL06523 & WO 2004016225 A2 20040226—Genentech Inc [US]) (See WO 2004016225 A2).

XP-002778546 ( Database Geneseq [online] Mar. 5, 2009 (Mar. 5, 2009), "Human PRO amino acid sequence Seq Id No. 2103.", XP002778546, retrieved from EBI accession No. GSP:AUZ26487 Database accession No. AUZ26487 & WO 2005016962 A2 20050224—Genentech Inc [US], et al.) (See WO2005016962A2).

XP-002778547 (Database Geneseq [online] Jun. 15, 2007 (Jun. 15, 2007), "Human lymphocyte clone G 115 soluble TCR Vgamma chain.", XP002778547, retrieved from EBI accession No. GSP:AAR55705 Database accession No. AAR55705 & WO 9412648 A2 19940609—Inst Nat Sante Rech Med [Fr], et al) (See WO9412648A2).

XP-002778548 ([X] Database USPTO Proteins [online] Aug. 10, 1998 (Aug. 10, 1998), "Sequence 17 from U.S. Pat. No. 5,723,309.", XP002778548, retrieved from EBI accession No. USPOP:I90500 Database accession No. AAC30862 & U.S. Pat. No. 5723309 A 19980303—Bonneville Marc [FR] (See U.S. Pat. No. 5,723,309).

Yu, Songtao et al. T cell receptor γδ phenotypic lymphocyte with tumor immunity, "Overseas Medicine (Immunology division)", No. 2, 1997 (machine translation of the abstract provided).

\* cited by examiner

```
CLUSTAL W (1.83) multiple sequence alignment
HLA_A02         MAVMAPRTLVLLLSGALALTQTWAGSHSMRYFFTSVSRPGRGEPRFIAVG
HLA_A24         MAVMAPRTLVLLLSGALALTQTWAGSHSMRYFSTSVSRPGRGEPRFIAVG
                ******************************** *****************

HLA_A02         YVDDTQFVRFDSDAASQRMEPRAPWIEQEGPEYWDGETRKVKAHSQTHRV
HLA_A24         YVDDTQFVRFDSDAASQRMEPRAPWIEQEGPEYWDEETGKVKAHSQTDRE
                ***********************************  ** ********.*

HLA_A02         DLGTLRGYYNQSEAGSHTVQRMYGCDVGSDWRFLRGYHQYAYDGKDYIAL
HLA_A24         NLRIALRYYNQSEAGSHTLQMMFGCDVGSDGRFLRGYHQYAYDGKDYIAL
                 :*    ***********:* *:****** *******************

HLA_A02         KEDLRSWTAADMAAQTTKHKWEAAHVAEQLRAYLEGTCVEWLRRYLENGK
HLA_A24         KEDLRSWTAADMAAQITKRKWEAAHVAEQQRAYLEGTCVDGLRRYLENGK
                *************** **:********** ********:  ********

HLA_A02         ETLQRTDAPKTHMTHHAVSDHEATLRCWALSFYPAEITLTWQRDGEDQTQ
HLA_A24         ETLQRTDPPKTHMTHHPISDHEATLRCWALGFYPAEITLTWQRDGEDQTQ
                ******* ******** :*********** *******************

HLA_A02         DTELVETRPAGDGTFQKWAAVVVPSGQEQRYTCHVQHEGLPKPLTLRWEP
HLA_A24         DTELVETRPAGDGTFQKWAAVVVPSGEEQRYTCHVQHEGLPKPLTLRWEP
                ************************** **********************

HLA_A02         SSQPTIPIVGIIAGLVLFGAVITGAVVAAVMWRRKSSDRKGGSYSQAASS
HLA_A24         SSQPTVPIVGIIAGLVLLGAVITGAVVAAVMWRRNSSDRKGGSYSQAASS
                *****.*********** **************** **************
```

FIG. 5

```
     AA Position              160          170
180
A*24:02:01:01    HVAEQQRAYL   EGTCVDGLRR   YLENGKETLQ
A*02:01:01:01    -----L----   -----EW---   ----------
A*24:03:01:01    ----------   -----EW---   ----------
A*25:01:01       -E---W----   --R--EW---   ----------
```

HUMAN LEUKOCYTE ANTIGEN RESTRICTED GAMMA DELTA T CELL RECEPTORS AND METHODS OF USE THEREOF

CROSS-REFERENCE

This application is a continuation of International Application No. PCT/EP2017/064323, filed Jun. 12, 2017, which claims the benefit of EP Application No. 16173970.1, filed Jun. 10, 2016; and EP Application No. 16173986.7, filed Jun. 10, 2016; all of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Dec. 7, 2018, is named 51887-709.301 SEQL.txt and is 159,744 bytes in size.

BACKGROUND

Cancer has a major impact on society across the globe. In 2016, an estimated 1,685,210 new cases of cancer will be diagnosed in the United States alone, and 595,690 people will die from the disease. By 2020, 18.2 million Americans, roughly 1 in 19 people, will be cancer patients or cancer survivors, up from 11.7 million (1 in 26) in 2005, according to the *Journal of Oncology Practice* (Erikson 2007).

In the light of overwhelming clinical success of cancer immunotherapies, γδ-T cells have come into the spotlight of interest, as tumor infiltrating γδ-T cells are the major predictor of clinical outcome across many cancer types. Several approaches have been tested in preclinical models and a number of clinical trials are currently on going. Despite multiple efforts to bring γδ-T cells into the clinic, their use has been largely ineffective. Therefore, new modalities of harnessing their anti-tumor efficacy are needed.

SUMMARY OF THE INVENTION

There exists a pressing need for alternative and effective treatment for a wide variety of cancers. The present invention addresses this need and provides related advantages as well. Accordingly, the present invention discloses a method of treating Disclosed herein is a composition comprising a polypeptide construct that selectively binds a human leukocyte antigen (HLA) molecule or portion thereof on a target cell when the HLA molecule is complexed to at least one additional HLA molecule on the target cell, wherein the polypeptide construct does not bind an uncomplexed HLA molecule. In certain cases, the uncomplexed HLA molecule is an HLA molecule which is not complexed to at least one additional HLA molecule. In some cases the polypeptide construct is expressed on a cell or synthesized. In some cases, an HLA molecule can be an HLA-A serotype or variant thereof. In some cases, an HLA-A serotype can be HLA-A*24. An HLA-A*24 can be HLA-A*24:02. In some cases a HLA molecule recognized by a polypeptide described herein can be complexed to a plurality of HLA molecules. In specific cases, the complexed HLA molecules can optionally form a cluster. A polypeptide construct can bind at least one co-receptor. In some cases, at least one co-receptor can be selected from a group consisting of: CD8, CD4, CD28, CCR, and CXCR4. In some cases, at least one co-receptor can be CD8. At least one co-receptor can comprise at least one of CD8 alpha or CD8 beta. In some cases, a target cell can be a cancer cell. A cancer cell may aberrantly express an HLA molecule. An aberrant expression can comprise a complexing on a target cell and an aberrant expression and a complexing may not be present on a comparable normal cell. An aberrant expression can comprise at least one of structure, mobility, flexibility, or compartmentalization as compared to a non-aberrantly expressed HLA on a comparable normal cell. A complexing can be detected by flow cytometry or microscopy. A cancer cell can overexpress an HLA as compared to a comparable normal cell. An overexpression can comprise from about 1% to about 100% expression on a population of cancer cells as detected by flow cytometry. An overexpression can comprise a positive detection of an HLA molecule by immunohistochemistry (IHC) analysis. A polypeptide construct can be expressed on immune cells. Immune cells can be from a myeloid or lymphoid lineage. In some cases, immune cells can be from a lymphoid lineage Immune cells from a lymphoid lineage can be at least one of natural killer (NK) cells, B cells, or T cells. In some cases, immune cells can be a plurality of T cells. A plurality of T cells can be engineered ail T cells. In some cases, immune cells can be virally modified to express a polypeptide construct. In some cases, immune cells can be non-virally modified to express a polypeptide construct. A polypeptide construct can encodes at least a portion of a: T cell receptor (TCR), antibody, chimeric antigen receptor (CAR), B cell receptor, and any combination thereof. In some cases, at least a portion of a TCR can be an engineered TCR. A TCR can be a γδTCR. A γδTCR can be a γ9δ2TCR or γ5δ1TCR. A γδTCR can be exogenous to an immune cell. Immune cells can be expanded Immune cells can be administered to a subject in need thereof. A subject in need thereof may have received a lymphodepleting regime prior to an administration of immune cells. A lymphodepleting regime can comprise an administration of cyclophosphamide, fludarabine, radiation, or a combination thereof. A polypeptide construct can comprise at least one of a γ-TCR polypeptide sequence, a δ-TCR polypeptide sequence, variants and fragments thereof. A polypeptide construct can comprise a CDR3 region of a γ-TCR polypeptide sequence selected from the list in Tables 2 and 6, a CDR3 region of a δ-TCR polypeptide sequence selected from the list in Tables 2 and 5, variants, and fragments thereof. A polypeptide construct can comprise a sequence with at least from about 80%, 90%, 95%, 98%, to about 99% sequence identity to a sequence selected from the sequences in the group consisting of SEQ ID NO: 2, SEQ ID NO: 3, amino acids 19-309 of SEQ ID NO: 4, amino acids 21-293 of SEQ ID NO: 5, SEQ ID NO: 4, SEQ ID NO:5 and SEQ ID NO: 6 to SEQ ID NO: 428. A composition can be administered in combination with at least one additional therapeutic agent to a subject in need thereof. A composition can be a pharmaceutical composition.

Disclosed herein is a pharmaceutical composition comprising: a composition as provided herein; and at least one of: an excipient, a diluent, or a carrier. A pharmaceutical composition can be administered in unit dosage form. A pharmaceutical composition can be in the form of a tablet, a liquid, a syrup, an oral formulation, an intravenous formulation, an intranasal formulation, a subcutaneous formulation, an inhalable respiratory formulation, a suppository, and any combination thereof. A pharmaceutical composition can be administered in the form of an infusion. In some cases, administering of a pharmaceutical composition at least partially ameliorates a disease or condition in a subject in need thereof. An amelioration can comprise a reduction in tumor size by at least about 30% as measured by computerized tomography (CT) scan. An amelioration can comprise stabilizing tumor size as measured by a less than 10% change in a baseline measurement of a diameter of a tumor lesion as measured by computerized tomography (CT) scan.

Disclosed herein is a method of treating a subject in need thereof comprising administering to the subject: an effective amount of a pharmaceutical composition comprising a polypeptide construct that binds a human leukocyte antigen (HLA) molecule complexed to at least one additional HLA molecule, and wherein the polypeptide construct does not bind an uncomplexed HLA molecule. In certain cases, the polypeptide construct does not bind the HLA molecule when the HLA molecule is not complexed to at least one additional HLA molecule. An HLA molecule can be of an HLA-A serotype or variant thereof. An HLA-A can be HLA-A*24. An HLA-A24 can be HLA-A*24:02. A polypeptide construct can comprise at least one of a γ-TCR polypeptide sequence, a δ-TCR polypeptide sequence, variants and fragments thereof. A polypeptide construct can comprise a CDR3 region of a γ-TCR polypeptide sequence selected from the list in Tables 2 and 6, a CDR3 region of a δ-TCR polypeptide sequence selected from the list in Tables 2 and 5, variants, and fragments thereof. A polypeptide construct can comprise a sequence with at least from about 80%, 90%, 95%, 98%, to about 99% sequence identity to a sequence selected from the sequences in the group consisting of SEQ ID NO: 2, SEQ ID NO: 3, amino acids 19-309 of SEQ ID NO: 4, amino acids 21-293 of SEQ ID NO: 5, SEQ ID NO:4, SEQ ID NO:5 and SEQ ID NO: 6 to SEQ ID NO: 428. In some cases, a method can further comprise administering at least one of a cytokine, chemotherapy, radiation, or a combination thereof to a subject in need thereof. A cytokine can be interleukin-2. In some cases, chemotherapy can comprise at least one of cyclophosphamide or fludarabine. In some cases, a polypeptide construct can be lyophilized. In some cases, a method can further comprise an adjuvant, diluent, carrier, or a combination thereof.

Disclosed herein is a method of treating a disease comprising aberrant HLA-A*24 expression comprising administering a first therapeutic agent that binds at least a portion of a human leukocyte antigen (HLA)-A*24, and at least one of: subsequently re-administering said first therapeutic agent, and administering a second therapeutic agent. A first therapeutic agent can comprise at least a portion of a T cell receptor (TCR), antibody, chimeric antigen receptor (CAR), B cell receptor, and any combination thereof. In some cases, at least a portion of a TCR can be an αβTCR or a γδTCR. A TCR can be a γδTCR. A first therapeutic agent can be an engineered cell expressing a γδTCR. An engineered cell can be from a lymphoid lineage or myeloid lineage. An engineered cell can be from a lymphoid lineage and may be selected from a natural killer (NK) cell, B cell, or T cell. An engineered cell can be a T cell. A first therapeutic agent can bind a cancer cell when an HLA-A*24 may be complexed to at least one additional HLA molecule. In some cases, a re-administration can be performed from about 24 hours to about 1 year after an administering a first therapeutic agent. In some cases, a method can further comprise detecting a level of a first therapeutic agent by at least one of quantitative PCR (qPCR) or flow cytometry. A second therapeutic agent can be selected from a group consisting of: chemotherapeutic, radiotherapeutic, or immunotherapeutic. A second therapeutic agent can be an immunotherapeutic.

Disclosed herein is an engineered cell comprising: a genomic alteration encoding a polypeptide construct that selectively binds a human leukocyte antigen (HLA) molecule or portion thereof on a target cell when said HLA molecule is complexed to at least one additional HLA molecule on said target cell, wherein said polypeptide construct does not bind an uncomplexed HLA molecule or does not bind said HLA molecule when said HLA molecule is not complexed to at least one additional HLA molecule. An HLA can comprise class I, class II, or a combination thereof. An HLA can comprise class I (HLA-I). An HLA-I can comprise HLA-A. HLA-A can be HLA-A*24. HLA-A*24 allele can comprise HLA-A*24:02. In some cases, a genomic alteration can comprise a knock in comprising a viral introduction of said polypeptide construct. A viral introduction can comprise a virus selected from a group consisting of a lentivirus, retrovirus, adenovirus, and any combination thereof. A viral introduction can comprise a retrovirus. In some cases, a polypeptide construct can comprise at least one γδTCR or fragment or variant thereof. A γδTCR can comprise a γ-TCR polypeptide sequence selected from the list in Tables 2 and 6, a CDR3 region of a δ-TCR polypeptide sequence selected from the list in Tables 2 and 5, variants, and fragments thereof. A polypeptide construct can selectively bind an HLA on a target cell, in a presence of at least one additional peptide and/or at least one co-receptor. In some cases, at least one co-receptor can be selected from a group consisting of: CD8, CD4, CD28, CCR, and CXCR4. At least one co-receptor can be CD8. At least one co-receptor can be at least one of CD8 alpha or CD8 beta.

Disclosed herein is a population of cells comprising the engineered cell of the present disclosure. In some cases, from about 60% to about 100% of engineered cells can express a polypeptide construct. Engineered cells can be a plurality of αβ T cells. A population can be administered to a subject in need thereof to control, reduce, or eliminate a cancer. In some cases, when a population can be administered to a subject in need thereof a viral infection can be controlled, reduced, or eliminated. An administration of an engineered cell can be effective in reducing tumor size by at least 30% as measured by computerized tomography (CT) scan. An administration can be effective in stabilizing tumor size as measured by a less than 10% change in a baseline measurement of a diameter of a tumor lesion as measured by computerized tomography (CT) scan. In some cases, from about $5 \times 10^4$ to about $1 \times 10^{12}$ cells can be administered to a subject in need thereof. In some cases, an administration can extend a life of a subject in need thereof from about 1 week to about 50 years as compared to an untreated subject. In some cases, engineered cells can be inhibited by a binding of an antibody. A binding of an antibody can reduce toxicity associated with an administration of engineered cells. The variant can be a humanized variant. In some cases, the variant is an scFv, or scFab.

Disclosed herein is a polynucleic acid comprising a sequence that is at least 90%, 95%, 97% or 99% identical to a sequence encoding a polypeptide sequence of at least one of SEQ ID NO: 2, SEQ ID NO: 3, amino acids 19-309 of SEQ ID NO: 4, amino acids 21-293 of SEQ ID NO: 5, SEQ ID NO: 4, or SEQ ID NO: 5.

Disclosed herein is an engineered cell comprising a receptor sequence that is at least 95%, 96%, 97%, 98%, or 99% identical to at least one of SEQ ID NO: 2, SEQ ID NO: 3, amino acids 19-309 of SEQ ID NO: 4, and amino acids 21-293 of SEQ ID NO: 5, SEQ ID NO: 4, or SEQ ID NO: 5.

Disclosed herein is an engineered cell comprising at least a portion of a receptor with a sequence that is at least 95%, 96%, 97%, 98%, or 99% identical to at least one of SEQ ID NO: 2, SEQ ID NO: 3, amino acids 19-309 of SEQ ID NO: 4, amino acids 21-293 of SEQ ID NO: 5, SEQ ID NO: 4, SEQ ID NO:5 and SEQ ID NO: 6 to SEQ ID NO: 428. In some cases, an engineered cell can be expanded to a population of engineered cells. A population of engineered cells can be formulated into a pharmaceutical composition.

Disclosed herein is a polypeptide that selectively binds a human leukocyte antigen (HLA) molecule or portion thereof on a target cell when said HLA molecule is complexed to at least one additional HLA molecule on said target cell, wherein said polypeptide does not bind an uncomplexed HLA molecule, or does not bind said HLA molecule when said HLA molecule is not complexed to at least one additional HLA molecule. In some cases, an HLA molecule can be an HLA-A serotype or variant thereof, preferably an HLA-A serotype can be HLA-A*24, more preferably, an HLA-A*24 can be HLA-A*24:02. A target cell can be a cancer cell, preferably a cancer cell can aberrantly expresses an HLA molecule. In some cases a polypeptide can be a δT-cell receptor chain or part thereof comprising a CDR3 region, a δT-cell receptor chain or part thereof can be represented by an amino acid sequence, an amino acid sequence comprising at least 60% sequence identity or similarity with any one of amino acid sequence SEQ ID NO: 3, amino acids 21-293 of SEQ ID NO: 5, SEQ ID NO:5 or SEQ ID NOs: 6 to 237. In some cases, a polypeptide can be a γT-cell receptor chain or part thereof comprising a CDR3 region, a γT-cell receptor chain or part thereof being represented by an amino acid sequence, an amino acid sequence comprising at least 60% sequence identity or similarity with any one of amino acid sequence SEQ ID NO: 2, amino acids 19-309 of SEQ ID NO: 4, SEQ ID NO:4 or SEQ ID NOs: 238 to 428.

Disclosed herein is a T cell receptor (TCR), preferably an engineered TCR comprising a δT-cell receptor chain or part thereof and a γT-cell receptor chain or part thereof.

Disclosed herein is a nucleic acid molecule encoding a polypeptide or a TCR.

Disclosed herein is a nucleic acid construct comprising a nucleic acid molecule.

Disclosed herein is a cell comprising a nucleic acid construct.

Disclosed herein is a polypeptide, a TCR, a nucleic acid molecule, a nucleic acid construct, or a cell for use as a medicament.

Disclosed herein is a polypeptide, a TCR, a nucleic acid molecule, a nucleic acid construct, or a cell for use as a medicament against cancer or an infection.

Disclosed herein is a method of reducing toxicity associated with the administration of an engineered cell, or a cell, comprising administration of at least one antibody or portion thereof to a subject in need thereof. In some cases, an antibody can be a blocking antibody or a neutralizing antibody. An antibody or portion thereof can inhibit binding of an engineered cell or a cell to a cell expressing HLA-A*24:02. A cell expressing HLA-A*24:02 can be at least one of a cancer cell or a comparable normal cell. An administration of at least one antibody or portion thereof can reduce a level of a cytokine release syndrome (CRS) in a subject in need thereof.

Provided herein are compositions and pharmaceutical compositions with a robust shelf life.

In some cases, a composition or pharmaceutical composition described herein containing at least one polypeptide described herein or a cell expressing a polypeptide described herein is stored in a sealed container at 25° C. or 4° C. and the container is placed in an atmosphere having 30%, 40%, 50%, 60%, 70%, 75%, 80%, 90% or 95% relative humidity. After 1 month, 2 months, 3 months, 6 months, 1 year, 1.5 years, 2 years, 2.5 years or 3 years, at least 50%, 60%, 70%, 80% or 90% of the composition or pharmaceutical composition remains as determined by standard protocols.

INCORPORATION BY REFERENCE

All publications, patents, and patent applications herein are incorporated by reference to the same extent as if each individual publication, patent, or patent application was specifically and individually indicated to be incorporated by reference. In the event of a conflict between a term herein and a term in an incorporated reference, the term herein controls.

BRIEF DESCRIPTION OF THE DRAWINGS

The novel features of the disclosure are set forth with particularity in the appended claims. A better understanding of the features and advantages of the disclosure will be obtained by reference to the following detailed description that sets forth illustrative embodiments, in which the principles of the disclosure can be utilized, and the accompanying drawings of which:

FIG. 1A shows results of an ELISPOT assay where γδ-T cell clone described herein are cocultured with SW480, EBV-LCL, and PBMCs. IFNγ spots/15,000 γδ T cells is shown.

FIG. 5 shows a sequence alignment between HLA-A*02:01 (SEQ ID NO: 439) and HLA-A*24:02 (SEQ ID NO: 440).

DETAILED DESCRIPTION OF THE DISCLOSURE

Figure 1:
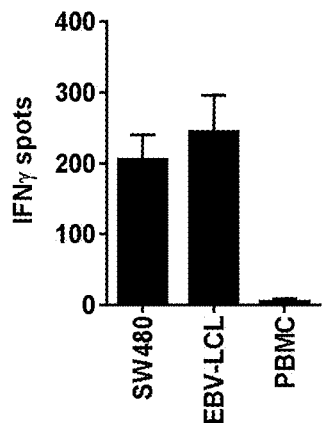
FIG. 1 B shows results of an ELISPOT assay of mock transduced cells and γδ-TCR cells described herein cocultured with, SW480, EBV-LCL, and PBMCs. IFNγ spots/15,000 γδ T cells is shown.
Figure 1:
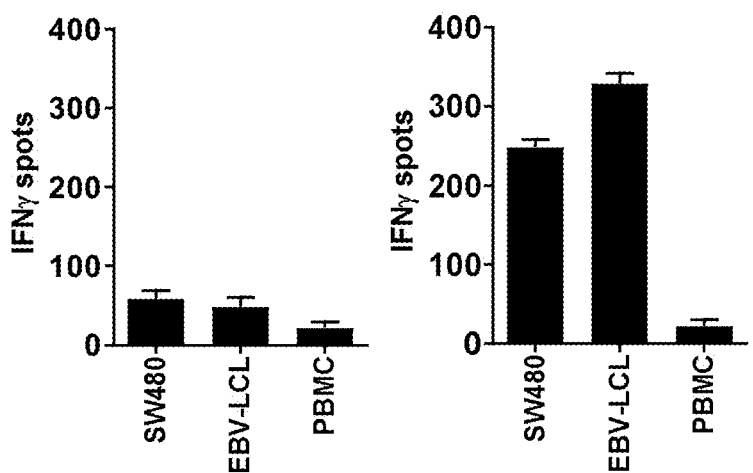

The following description and examples illustrate embodiments of the disclosure in detail. It is to be understood that this disclosure is not limited to the particular embodiments described herein and as such can vary. Those of skill in the art will recognize that there are numerous variations and modifications of the disclosure, which are encompassed within its scope. Unless otherwise indicated, any embodiment can be combined with any other embodiment.

All terms are intended to be understood as they would be understood by a person skilled in the art. Unless defined otherwise, all technical and scientific terms used herein have the same meaning as commonly understood by one of ordinary skill in the art to which the disclosure pertains.

As used herein, unless otherwise indicated, some inventive embodiments herein contemplate numerical ranges. A variety of aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range as if explicitly written out. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. When ranges are present, the ranges include the range endpoints.

The following definitions supplement those in the art and are directed to the current application and are not to be imputed to any related or unrelated case, e.g., to any commonly owned patent or application. Although any methods and materials similar or equivalent to those described herein can be used in the practice for testing of the present disclosure, the preferred materials and methods are described herein. Accordingly, the terminology used herein

Definitions

As used herein, unless otherwise indicated, the article "a" means one or more unless explicitly otherwise provided for.

As used herein, unless otherwise indicated, terms such as "contain," "containing," "include," "including," and the like mean "comprising".

The term "activation" and its grammatical equivalents as used herein can refer to a process whereby a cell transitions from a resting state to an active state. This process can comprise a response to an antigen, migration, and/or a phenotypic or genetic change to a functionally active state.

"Antigen" as used herein means a substance that is recognized and bound specifically by an antigen binding unit. Antigens can include peptides, proteins, glycoproteins, polysaccharides, and lipids; portions thereof and combinations thereof "Antigen" can also refer to a molecule that provokes the immune response. This immune response may involve either antibody production, or the activation of specific immunologically-competent cells, or both. The skilled artisan will understand that any macromolecule, including virtually all proteins or peptides, can serve as an antigen.

The term "autologous" and its grammatical equivalents as used herein can refer to as originating from the same being. For example, a sample (e.g., cells) can be removed, processed, and given back to the same subject (e.g., patient) at a later time. An autologous process is distinguished from an allogenic process where the donor and the recipient are different subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the invention, and vice versa. Furthermore, compositions of the invention can be used to achieve methods of the invention.

The term "epitope" and its grammatical equivalents as used herein can refer to a part or a portion or a fragment of an antigen that can be recognized by antibodies, B cells, T cells or engineered cells expressing polypeptide constructs described herein. For example, an epitope can be a cancer epitope that is recognized by a TCR, for instance a gamma delta TCR described herein. Multiple epitopes within an antigen can also be recognized. The epitope can also be mutated.

The term "engineered" and its grammatical equivalents as used herein can refer to one or more alterations of a nucleic acid, e.g., the nucleic acid within an organism's genome or of a polypeptide. The term "engineered" can refer to alterations, additions, and/or deletion of genes or polypeptides. An engineered cell can also refer to a cell with an added, deleted and/or altered gene or polypeptide.

The term "cell" or "engineered cell" and their grammatical equivalents as used herein can refer to a cell of human or non-human animal origin. An engineered cell can also refer to an engineered effector cell. In certain cases, an engineered cell refers to an effector cell engineered to express a polypeptide construct described herein.

The term "good manufacturing practices" (GMP) and its grammatical equivalents as used herein can refer to products that are safe, effective, or pure according to the FDA. GMP can also sometimes be referred to as "cGMP". The "c" stands for "current." Manufacturers of a product can employ technologies and systems which are up-to-date in order to comply with regulation of GMP products. GMP compatible products are typically utilized in the clinical setting as opposed to the research setting.

The term "transfection" as used herein refers to the introduction of foreign nucleic acid into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign nucleic acid, DNA or RNA, into the genome of the transfected cell. The term "stable transfectant" refers to a cell which has stably integrated foreign DNA into the genomic DNA.

Nucleic acids and/or nucleic acid sequences are "homologous" when they are derived, naturally or artificially, from a common ancestral nucleic acid or nucleic acid sequence. Proteins (or polypeptides) and/or protein (polypeptide) sequences are homologous when their encoding DNAs are derived, naturally or artificially, from a common ancestral nucleic acid or nucleic acid sequence.

In the context of the invention, a polypeptide is represented by an amino acid sequence. Preferred polypeptides are δT-cell and/or γT-cell receptor chains or parts thereof which mediate an anti-tumor response as explained herein. In the context of the invention, a nucleic acid molecule as a nucleic acid molecule encoding such a δT-cell and/or γT-cell receptor chain or part thereof is represented by a nucleic acid or nucleotide sequence which encodes such a polypeptide. A nucleic acid molecule may comprise a regulatory region. It is to be understood that each nucleic acid molecule or polypeptide or construct as identified herein by a given Sequence Identity Number (SEQ ID NO) is not limited to this specific sequence as disclosed. Throughout this application, each time one refers to a specific nucleotide sequence SEQ ID NO (take SEQ ID NO: X as example) encoding a given polypeptide, one may replace it by an homologous nucleotide sequence defined as follows: i. a nucleotide sequence comprising a nucleotide sequence that has at least 60% sequence identity or similarity with SEQ ID NO: X; ii. a nucleotide sequences the complementary strand of which hybridizes to a nucleic acid molecule of sequence of (i); (iii). a nucleotide sequence the sequence of which differs from the sequence of a nucleic acid molecule of (i) or (ii) due to the degeneracy of the genetic code; or, (iv) a nucleotide sequence that encodes an amino acid sequence that has at least 60% amino acid identity or similarity with an amino acid sequence encoded by a nucleotide sequence SEQ ID NO: X. Throughout this application, each time one refers to a specific amino acid sequence SEQ ID NO (take SEQ ID NO: Y as example), one may replace it by: a polypeptide comprising an amino acid sequence that has at least 60% sequence identity or similarity with amino acid sequence SEQ ID NO: Y. Each nucleotide sequence or amino acid sequence described herein by virtue of its identity or similarity percentage (at least 60%) with a given nucleotide sequence or amino acid sequence respectively has in a further preferred embodiment an identity or a similarity of at least 65%, 70%, 75%, 80%, 85%, 90%, 95%, 97%, 98%, 99% or more identity or similarity with the given nucleotide or amino acid sequence respectively. In a preferred embodiment, sequence identity or similarity is determined by comparing the whole length of the sequences as identified herein. Unless otherwise indicated herein, identity or similarity with a given SEQ ID NO means identity or similarity based on the full length of said sequence (i.e. over its whole length or as a whole).

The homologous molecules can be termed homologs. For example, any naturally occurring proteins, as described herein, can be modified by any available mutagenesis method. When expressed, this mutagenized nucleic acid encodes a polypeptide that is homologous to the protein encoded by the original nucleic acid. Homology is generally inferred from sequence identity between two or more nucleic acids or proteins (or sequences thereof). The precise percentage of identity between sequences that is useful in establishing homology varies with the nucleic acid and protein at issue, but as little as 25% sequence identity is routinely used to establish homology. Higher levels of sequence identity, e.g., 30%, 40%, 50%, 60%, 70%, 80%, 90%, 95% or 99% or more can also be used to establish homology. Identity of at least 65%, 70%, 75%, 80%, 85%, 90%, 95%, 97%, 98%, 99% or 100% are encompassed herein.

"Sequence identity" is herein defined as a relationship between two or more amino acid (polypeptide or protein) sequences or two or more nucleic acid (polynucleotide) sequences, as determined by comparing the sequences. The identity between two amino acid or two nucleic acid sequences is preferably defined by assessing their identity within a whole SEQ ID NO as identified herein or part thereof. Part thereof may mean at least 50% of the length of the SEQ ID NO, or at least 60%, or at least 70%, or at least 80%, or at least 90%. In the art, "identity" also means the degree of sequence relatedness between amino acid or nucleic acid sequences, as the case may be, as determined by the match between strings of such sequences. "Similarity" between two amino acid sequences is determined by comparing the amino acid sequence and its conserved amino acid substitutes of one polypeptide to the sequence of a second polypeptide. "Identity" and "similarity" can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48:1073 (1988). Preferred methods to determine identity are designed to give the largest match between the sequences tested. Methods to determine identity and similarity are codified in publicly available computer programs. Preferred computer program methods to determine identity and similarity between two sequences include e.g. the GCG program package (Devereux, J., et al., Nucleic Acids Research 12 (1): 387 (1984)), BestFit, BLASTP, BLASTN, and FASTA (Altschul, S. F. et al., J. Mol. Biol. 215:403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215:403-410 (1990). The well-known Smith Waterman algorithm may also be used to determine identity. Preferred parameters for polypeptide sequence comparison include the following: Algorithm: Needleman and Wunsch, J. Mol. Biol. 48:443-453 (1970); Comparison matrix: BLOSSUM62 from Hentikoff and Hentikoff, Proc. Natl. Acad. Sci. USA. 89:10915-10919 (1992); Gap Penalty: 12; and Gap Length Penalty: 4. A program useful with these parameters is publicly available as the "Ogap" program from Genetics Computer Group, located in Madison, Wis. The aforementioned parameters are the default parameters for amino acid comparisons (along with no penalty for end gaps). Preferred parameters for nucleic acid comparison include the following: Algorithm: Needleman and Wunsch, J. Mol. Biol. 48:443-453 (1970); Comparison matrix: matches=+10, mismatch=0; Gap Penalty: 50; Gap Length Penalty: 3. Available as the Gap program from Genetics Computer Group, located in Madison, Wis. Given above are the default parameters for nucleic acid comparisons. Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to Ser; Arg to Lys; Asn to Gln or His; Asp to Glu; Cys to Ser or Ala; Gln to Asn; Glu to Asp; Gly to Pro; His to Asn or Gln; Ile to Leu or Val; Leu to Ile or Val; Lys to Arg, Gln or Glu; Met to Leu or Ile; Phe to Met, Leu or Tyr; Ser to Thr; Thr to Ser; Trp to Tyr; Tyr to Trp or Phe; and Val to Ile or Leu.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The nucleic acid sequence thus codes for the amino acid sequence.

The term "subject", as used herein, refers to any animal, e.g., a mammal or marsupial. Subjects of the present invention include but are not limited to humans, non-human primates (e.g., rhesus or other types of macaques), mice, pigs, horses, donkeys, cows, sheep, rats and fowl of any kind.

The term "recipient" and their grammatical equivalents as used herein can refer to a human or non-human animal in receipt of a therapy or treatment.

The term "peripheral blood lymphocytes" (PBL) and its grammatical equivalents as used herein can refer to lymphocytes that circulate in the blood (e.g., peripheral blood). Peripheral blood lymphocytes can refer to lymphocytes that are not localized to organs. Peripheral blood lymphocytes can comprise T cells, NK cells, B cell, or any combinations thereof.

The term "immunoresponsive cell" can refer to a cell that can elicit an immune response, including but not limited to T cells, B cells, and NKT cells, their respective precursor cells and progeny thereof. An immunoresponsive cell can also refer to a cell of a lymphoid or myeloid lineage.

The term "T cell" and its grammatical equivalents as used herein can refer to a T cell from any origin. For example, a T cell can be a primary T cell, e.g., an autologous T cell, a cell line, etc. The T cell can also be human or non-human.

The term "T cell activation" or "T cell triggering" and its grammatical equivalents as used herein can refer to the state of a T cell that has been sufficiently stimulated to induce detectable cellular proliferation, cytokine production and/or detectable effector function. In some cases, "full T cell activation" can be similar to triggering T cell cytotoxicity. T cell activation can be measured using various assays known in the art. Said assays can be an ELISA to measure cytokine secretion, an ELISPOT, flow cytometry assays to measure intracellular cytokine expression (CD107), flow cytometry assays to measure proliferation, and cytotoxicity assays (51Cr release assay) to determine target cell elimination.

The term "sequence" and its grammatical equivalents when used to refer to a nucleotide sequence (SEQ ID NO in the sequence listing), that can encompass DNA or RNA, and can be either single-stranded or double stranded. A nucleic acid sequence can be mutated. A nucleic acid sequence can be of any length, for example, between 2 and 1,000,000 or more nucleotides in length (or any integer value there between or there above), e.g., between about 100 and about 10,000 nucleotides or between about 200 and about 500 nucleotides.

As defined herein a polypeptide construct is preferably an engineered polypeptide or a recombinant polypeptide which has been constructed by standard molecular biology techniques and which does not occur in nature. The expression "polypeptide construct" may be replaced by the word polypeptide.

The word "about" when used in association with an integer (about 10) preferably means that the value may be the given value of 10 more or less 1 of the value: about 10 preferably means from 9 to 11. The word "about" when used in association with a numerical value (about 10.6) preferably means that the value may be the given value of 10.6 more or less 1% of the value 10.6.

In the context of the invention reference is made to a healthy, normal, or non-cancerous or non-infected cell by comparison to a diseased, cancerous, aberrant, malignant or infected cell. Each of the terms healthy, normal, non-cancerous or non-infected is synonymous and may be interchangeably used. Each of the terms diseased, aberrant is synonymous and can be interchanged with cancerous, malignant or infected.

In the context of the invention, a part or a fragment or a portion of a nucleic acid or of a nucleic acid sequence or of a polypeptide or of a polypeptide sequence or of an epitope or of an epitope sequence, means at least 50% of the length of its sequence, or at least 60%, or at least 70%, or at least 80%, or at least 90%.

The term "vector" and its grammatical equivalents can refer to a composition of matter which comprises an isolated nucleic acid and which can be used to deliver isolated nucleic acid to an interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Targeting Compositions and Methods of Use Thereof

Disclosed herein are compositions of human leukocyte antigen (HLA)-specific receptors that mediate anti-tumor responses when an HLA receptor is detected on a cell surface. In certain embodiments is a composition comprising polypeptide constructs that encompass one or more HLA-specific receptors, for instance γδ TCRs fragments or variants thereof that can mediate anti-tumor responses. A polypeptide described herein can be utilized to selectively bind a conformationally constrained HLA molecule. In specific embodiments, a polypeptide construct described herein can bind an HLA molecule expressed on a cancer cell selectively as compared to corresponding HLA molecule on non-cancer cells. A polypeptide construct described herein can comprise at least one receptor comprising a sequence disclosed in any one of Table 2, Table 4 and Table 5 or a portion thereof. In some cases, provided herein can be a composition comprising polypeptide constructs that can encompass one or more HLA-specific receptors, for instance γδ TCR fragments or variants thereof that can mediate anti-tumor responses. A polypeptide disclosed herein can be utilized to selectively bind a conformationally constrained HLA molecule. For example, a polypeptide construct disclosed herein can selectively bind a HLA molecule or portion thereof on a target cell when said HLA molecule can be complexed to at least one additional HLA molecule on a target cell. In some cases, a polypeptide construct does not bind to an uncomplexed HLA molecule. In some embodiments, an uncomplexed HLA molecule is a HLA molecule which is not complexed to at least one additional HLA molecule. The polypeptide construct can be expressed in an engineered cell or synthesized.

In some cases is a method of making an engineered cell expressing a polypeptide construct comprising a HLA receptor described herein. For example, a method can include a step of providing cells; providing a nucleic acid sequence encoding γδ TCR chains or fragments or variants thereof, introducing the nucleic acid sequence into cells to provide for an engineered cell with a γδ TCR receptor, fragment or variant thereof, exhibiting specificity to HLA.

In some embodiments is a polypeptide construct that selectively binds a HLA molecule or portion thereof on a target cell when said HLA molecule is complexed to at least one additional HLA molecule on a target cell. In some cases, a polypeptide construct does not bind to an HLA molecule which is not complexed to at least one additional HLA molecule (also referred to herein in certain embodiments as an uncomplexed HLA molecule). In some cases, a polypeptide construct can be expressed in an engineered cell or synthesized.

Disclosed herein can be various forms of binding units comprised by polypeptide constructs described herein. For example, a binding unit comprised by a polypeptide construct described herein can be a γδ TCR, for instance comprising a sequence disclosed in at least one of Table 2, Table 4 and Table 5. A γδ TCR can directly recognize antigens in the form of intact proteins or non-peptidic compounds, unlike αβ TCRs which recognize peptide antigens bound to major histocompatibility complex molecules (MHC). Gamma-delta T cells (γδ T cells) can express a unique T-cell receptor (TCR) composed in some cases of one γ-chain and one δ-chain. Each T cell receptor can be a dimer consisting of one alpha and one beta chain or one delta and one gamma chain. In a single cell, the T cell receptor loci are rearranged and expressed in the order delta, gamma, beta, and alpha. The gamma locus includes V (variable), J (joining), and C (constant) segments.

For example, in some cases γδT cell clones can recognize Class I or Class II MHCs, including HLA-DR7, HLA-A2, HLA-A*24 (see Spits et al., 1990, Cytotoxic activity and lymphokine production of T cell receptor (TCR)-αβ+ and TCR-γδ+ cytotoxic T lymphocyte (CTL) clones recognizing HLA-A2 and HLA-A2 mutants, *The Journal of Immunology* 144: 4156-4162, and Ciccone et al., 1989, Specificity of human T lymphocytes expressing a γ/δ T cell antigen receptor. *European Journal of Immunology* 19: 1267-1271). However, in direct contrast to the aforementioned references, γδT cell compositions described herein recognize HLA-A*24:02 expressed by malignant cells and not healthy counterpart cells and the recognition can be inhibited by fixation of cells, which may suggest spatial and conformational changes during the recognition process which differs from also classical allo- or peptide-reactivitiy of αβT cells.

In embodiments described herein, a polypeptide construct comprises a γδTCR that can target a cancer. Examples of various cancers that can be targeted with engineered T cells, including γδTCR-engineered T cells, include but are not limited to liver cancer, stomach cancer, esophageal cancer, lung cancer, breast cancer, head and neck cancer, ovarian cancer, kidney cancer, bladder cancer, cervical cancer, pancreatic cancer, liposarcoma, testicular noneminomatous germ cell cancer, melanoma, adenoma, adrenal cancer, schwannoma, malignant, fibrous histiochytoma, or any combination thereof. Additionally immunoresponsive cells disclosed herein, such as γδTCR-expressing T cells disclosed herein, can be utilized to target ovarian carcinoma, cholangiocarcinoma, mesothelioma, breast cancer, squamous cell carcinoma of the lunch, cervical intraetithelial neoplasia, squamous cell carcinoma of the cervix, intrahepatic and extrahepatic cancer, gallbladder carcinoma, invasive ductal carcinoma, clear cell carcinoma, oncocytoma, papillary carcinoma, adenocarcinoma, papillary carcinoma, and lobular and medullary carcinoma of the breast.

In some cases, a γδTCR can target an antigen or portion thereof expressed on a tumor, such as HLA-A*24:02 without the need for HLA processing and presentation. A γδ TCR described herein can bind a germline-encoded receptor repertoire. For example, a γδTCR can recognize and bind stress-induced self-antigens, lipids, or pyrophosphates that can be secreted by some microbes, for instance a virus or can be overproduced in tumor cells. A γδ TCR can additionally bind a surface expressed protein of a cell or portion thereof. In some cases, a γδ TCR can also bind a protein or portion thereof that can be expressed due to a DNA damage pathway. In some cases, a γδTCR described herein can also bind a lipid or portion thereof expressed on a cancer cell.

In some cases, HLA-A*24:02 may be overexpressed on a cancer and have reduced or no expression on normal tissue. In some cases, specific antigens and epitopes thereof of a cancer can be targeted with a γδTCR or an endogenous or exogenous αβTCR. Antigens may be derived from a wide variety of tumor antigens such as those from tumors resulting from mutations, shared tumor specific antigens, differentiation antigens, and antigens overexpressed in tumors.

In some cases, a peptide can be any self-peptide in combination with spatial and/or conformational changes (target-conformation, short: T-conformation) in an HLA, such as HLA-A*24:02, which can differ from healthy, non-stressed, or non-transformed cells. In some cases, a cancer cell may aberrantly express an HLA-A protein in a K-confirmation. In some cases, complexing of an HLA-A can comprise a clustering of an HLA molecule on a tumor cell surface. In some cases, a complex comprises a K-conformation. A K-conformation can comprise at least one of differential special distribution or differential clustering of an HLA molecule on a tumor cell when compared to a comparable normal cell, such as a non-tumorous comparable cell.

In some cases, provided herein can be a method of identifying an antigen binding unit that can be immunoreactive with a desired antigen. Such a method can involve the following steps: (a) preparing a genetically diverse library of antigen binding units, wherein a library can comprise at least one subject antigen binding unit; (b) contacting a library of antigen binding units with a desired antigen; (c) detecting a specific binding between antigen binding units and an antigen, thereby identifying an antigen binding unit that can be immunoreactive with a desired antigen.

Tissue expression of an antigen or T-conformation (both can be a target or "the target") may be measured by immunohistochemistry (IHC) analysis and/or flow cytometric analysis. Tissue expression may also be measured in terms of copy number by quantitative PCT (qPCR). In some cases, a target antigen may be expressed on a cell surface of a cancer. γδTCR may target cell surface antigens in a non-MHC restricted manner. Overexpression can be or can be about 1-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, or up to 100-fold over expression on a normal tissue as measured by IHC, qPCR, or flow cytometry.

The ability of an antigen binding unit to specifically bind to a desired antigen or target can be tested by a variety of procedures well established in the art. See Harlow and Lane (1988) Antibodies: A Laboratory Manual, Cold Spring Harbor Laboratory, New York; Gherardi et al. (1990) *J. Immunol. Meth.* 126:61-68. Typically, antigen binding units exhibiting desired binding specificities can be detected directly by immunoassays, for example, by reacting labeled antigen binding units with the antigens that are immobilized on a solid support or substrate. In general, a substrate to which an antigen can adhere can be fabricated with material exhibiting a low level of non-specific binding during immunoassay. An example solid support can be made from one or more of the following types of materials: plastic polymers, glass, cellulose, nitrocellulose, semi-conducting material, and metal. In some examples, a substrate can be a petri dish, chromatography beads, magnetic beads, and the like.

For such solid-phase assays, unreacted antigen binding units can be removed by washing. In a liquid-phase assay, however, unreacted antigen binding units can be removed by some other separation technique, such as filtration or chromatography. After binding an antigen to labeled antigen binding units, an amount of bound label can be determined. A variation of this technique can be a competitive assay, in which an antigen can be bound to saturation with an original binding molecule. When a population of a subject antigen binding unit can be introduced to a complex, only those that exhibit higher binding affinity may be able to compete, and thus remain bound to an antigen.

Alternatively, specific binding to a given antigen or to a given target can be assessed by cell sorting, which involves presenting a desired antigen on cells to be sorted, then labeling target cells with antigen binding units that may be coupled to detectable agents, followed by separating labeled cells from unlabeled ones in a cell sorter. A sophisticated cell separation method can be fluorescence-activated cell sorting (FACS).

Subsequent analysis of eluted antigen or target binding units may involve protein sequencing for delineating amino acid sequences of the light chains and heavy chains. Based on the deduced amino acid sequences, a cDNA encoding antibody polypeptides can then be obtained by recombinant cloning methods including PCR, library screening, homology searches in existing nucleic acid databases, or any combination thereof. Commonly employed databases include but are not limited to GenBank, EMBL, DDBJ, PDB, SWISS-PROT, EST, STS, GSS, and HTGS.

Due to the degeneracy of the genetic code, there can be considerable variation in nucleotides of a polypeptide construct coding sequence, as well as sequences suitable for construction of a polynucleotide and vectors disclosed herein. Sequence variants may have modified DNA or amino acid sequences, one or more substitutions, deletions, or additions, the net effect of which can be to retain a desired binding activity. For instance, various substitutions can be made in a coding region that either do not alter amino acids encoded or result in conservative changes. These substitutions can be encompassed herein. Conservative amino acid substitutions can include substitutions within the following groups: glycine, alanine; valine, isoleucine, leucine; aspartic acid, glutamic acid; asparagine, glutamine; serine, threonine; lysine, arginine; and phenylalanine, tyrosine. While conservative substitutions may not effectively change one or more amino acid residues contained in a polypeptide to be produced, substitutions may not interfere with an antigen-binding activity of a resulting antigen binding unit to be produced. Nucleotide substitutions that may not alter amino acid residues encoded can be useful for optimizing gene expression in different systems. Suitable substitutions are known to those of skill in the art and are made, for instance, to reflect preferred codon usage in expression systems. In some cases, modifications to a binding unit can be made to alter binding activity of a target.

In some cases, a desired binding unit in a polypeptide construct may be an alpha beta TCR (αβ-TCR). In some embodiments, a T cell receptor (TCR) comprised by a polypeptide construct described herein is composed of multiple chains (αβ or γδ) that pair on the surface of the T cell to form a heterodimeric receptor.

An αβ TCR can be expressed on most T cells in the body and can be known to be involved in the recognition of specific MHC-restricted antigens. Each α and β chain are composed of two domains: a constant domain (C) which anchors the protein to the cell membrane and is associated with invariant subunits of the CD3 signaling apparatus; and a variable domain (V) that confers antigen recognition through six loops, referred to as complementarity determining regions (CDRs). Each of the V domains comprises three CDRs; e.g., CDR1, CDR2 and CDR3 with CDR3 as the hypervariable region. These CDRs interact with a complex formed between an antigenic peptide bound to a protein encoded by the major histocompatibility complex (pepMHC) (e.g., HLA-A, HLA-B, HLA-C, HLA-DPA1, HLA-DPB1, HLA-DQA1, HLA-DQB1, HLA-DRA, or HLA-DRB1 complex). In some instances, the constant domain further comprises a joining region that connects the constant domain to the variable domain. In some cases, the beta chain further comprises a short diversity region which makes up part of the joining region.

In some cases, γδT cells can bind to ligands that can be different from those of αβT cells. For example, γδT cell recognition in some cases may not utilize antigen processing and in some cases γδT cells can recognize proteins directly (Chien et al., 1996, Recognition by γ/δ T cells, *Annual Review of Immunology* 14: 511-532). In contrast to an αβ TCR, the γδ TCR is composed of one γ chain and one δ chain. Although much less abundant in the body than αβ Tcells, γδ T cells combine potent anti-tumor effector functions with the recognition of broadly expressed tumor-associated molecules, and therefore are strong candidates for clinical application in cancer immunotherapy. The majority of γδ T cells are activated in an MHC-independent manner and do not require antigen processing, which is in contrast to MHC-restricted αβ T cells. Instead, γδ T cells rely on cell-cell contact with antigen-presenting cells and directly recognize antigens in the form of intact proteins or non-peptidic compounds. Activation of γδ T cells by TCR-mediated antigen recognition on a target cell can lead to production of cytokines and chemokines as well as cytoloysis of the target cell (e.g., tumor cell).

In some cases, a difference between HLA-A*02 and HLA-A*24 can reside in a peptide binding cleft, α1 and α2 helices, or a combination thereof. In some cases, a residue that may be altered can be W107, A185, S207, or a combination thereof in an HLA-A*02 structure. In other cases, an HLA-A*24 protein may have substitutions of G, P and G at these locations, respectively. Polymorphisms can exist throughout an HLA-A*24 protein. For example, a polymorphism can be on a C-terminus, N-terminus, or a combination thereof.

In some cases, a polymorphism can be plotted in an HLA-A protein. For example, an HLA-A*02 can have a polymorphism on an alpha3 domain. In some cases a polymorphism can have effects on binding. In some cases polymorphisms on an HLA-A protein, such as HLA-A*24 can result in differences in binding at the CD4 vs CD8 binding site.

Vγ9Vδ2 T cells, the major γδ T cell subset in human peripheral blood, can express γδ TCRs composed of Vγ9 and Vδ2 chains, and are specifically activated by intermediates of the mammalian mevalonate pathway such as isopentenyl pyrophosphate (IPP) or the microbial 2-C-methyl-D-erythritol 4-phosphate (MEP) pathway. Intracellular phosphoantigen (pAg) levels accumulate in tumor cells due to dysregulation of the mevalonate pathway or upon microbial infection, allowing the targeting of transformed or infected cells by Vγ9Vδ2 cells. Similarly, intracellular pAg levels can be pharmaceutically increased by treating cells with mevalonate pathway inhibitors such as aminobisphosphonates (ABPs), thereby sensitizing cells toward recognition by Vγ9Vδ2 T cells. In some cases, a Vγ5Vδ1 TCR can be utilized in a composition provided herein.

Any Vγ Vδ TCR, preferably a Vγ5Vδ1 TCR or other Vδ2$^{neg}$ γδ TCR can be isolated and introduced into a T cell, preferably an αβ T cell. In some cases, an endogenous TCR of an αβ T cell remains present. In other cases, an endogenous αβ TCR is genomically disrupted before, concurrent with, or after introduction of a Vγ5Vδ1 TCR or other Vδ2$^{neg}$ γδ TCR.

In adult peripheral blood, a γδT cell subset can express TCRs comprising Vδ2 and Vγ9 gene segments and can be referred to as Vδ2$^{pos}$ γδT cells. In contrast, γδ T cells that reside in epithelial tissue express TCRs composed of mainly Vδ1 or Vδ3 chains paired with diverse Vγ chains, and a proportion of these γδ-T cells expresses CD8αα or CD8αβ, which can be referred to as Vδ2$^{neg}$ γδ-T cells. It has been demonstrated that CD8αα or CD8αβ can play a co-stimulatory role for leukemia-reactive Vδ1 TCRs (Scheper et al., 2013, γδ T cells elicited by CMV reactivation after allo-SCT cross-recognize CMV and leukemia, *Leukemia* 27: 1328-1338). In some cases, Vδ2$^{neg}$ γδT cells may be used as a tool to tackle CMV infection and leukemia. In other cases, a CD8αα, CD8αβ, or other molecules can play a co-stimulatory role for γδT cells that are reactive to HLA-A*24 expressed by cancer cells.

In some cases, a co-receptor may be involved in HLA interaction of a polypepetide construct described herein. For example, a co-receptor may be recruited or involved in a TCR-peptide binding in the context of HLA or independent of HLA. Various co-receptors may be involved. For example, at least one of CD8, CD4, CD28, CCR, and CXCR4 may be involved. A CD receptor may be a co-receptor for a TCR-HLA interaction. For example, CD4 acts as a co-receptor to the TCR when it can bind HLA-Class II. CD8 acts as a co-receptor to the TCR when it can bind HLA-Class I. A CD4 receptor in particular can interact with HLA class II following a "ball-on-stick" model, where a Phe-43 ball fits into the conserved hydrophobic α2 and β2 domain residues. During binding with class II, CD4 maintains independent structure and may not form any bonds with the TCR receptor. In some cases, a co-receptor can be CD8, such as CD8 alpha.

In some cases, a soluble binding unit can be generated and included as part of a polypeptide construct described herein. An affinity of a TCR ligand interaction can be relatively low as compared to an antibody. One of the reasons for this difference can be avidity. For example, antibodies can have 2 ligand binding sites on one molecule leading to enhanced binding. Antibodies can have from 1 to 10 ligand binding sites in some cases. For example, several TCR-antibody chimeras can be generated and tested before arriving at a desired chimera. For example, γδ-variable domains can replace heavy and light chain variable domains of an antibody. In addition to enhanced binding, an Fc domain of an antibody can mediate cytotoxicity through Fcγ-receptor positive immune cells and/or a complementary system. In some cases, TCR-antibody chimeras can be generated using HEK293 cells and subsequently purified using protein A affinity chromatography followed by size exclusion chromatography. A proper folding of chimeras can be probed using conformational-specific antibodies that can target γ and δ variable domains. Chimeras can be used in antibody dependent cell mediated cytotoxicity (ADCC) and complement dependent cytotoxicity (CDC) assays to determine functional efficacy to HLA-A*24:02 tumor cells. After performing in vitro assays, functional efficacy of TCR-antibody chimeras can be tested in vitro and/or in vivo.

In some cases, a soluble form of a polypeptide construct can recognize a complexed HLA-A*24 or portion thereof. A polypeptide construct can include various forms to binding entities such as a TCR, antibody, scFv, BCR, or any combination thereof. In some cases, at least a portion of a TCR, such as a Vγ9Vδ2 or Vγ5Vδ1, can be generated and utilized in a pharmaceutical composition. A soluble form of a Vγ9Vδ2 or Vγ5Vδ1 can recognize and bind a complexed HLA-A. In some cases, a soluble form of a Vγ9Vδ2 or Vγ5Vδ1 can recognize and bind a complexed HLA-A*24 on a tumor cell. In some cases, a soluble form of Vγ9Vδ2 or Vγ5Vδ1 can recognize and bind a complexed HLA-A*24: 02. A soluble form of a polypeptide can also recognize and bind an aberrant expression of an HLA-A*24 that may comprise at least one of an aberrant structure, aberrant mobility, aberrant flexibility, or aberrant compartmentalization as compared to a non-aberrantly expressed HLA-A*24 on a comparable healthy cell. In some cases, complexing can comprise a clustering of an HLA molecule. In some cases, a complex comprises a K-conformation. A K-conformation can comprise at least one of differential special distribution or differential clustering of said HLA molecule when compared to a comparable normal cell. In some cases, a composition disclosed herein can target and bind an HLA-A*24: 02 in a K-conformation.

Human Leukocyte Antigen (HLA)

HLA-A belong to a HLA class I heavy chain paralogue. This class I molecule can be a heterodimer including a heavy chain and a light chain (beta-2 microglobulin). A heavy chain can be anchored in the membrane. Class I molecules can play a role in an immune system by presenting peptides derived from an endoplasmic reticulum lumen. They can be expressed in nearly all cells. A heavy chain can be approximately 45 kDa and its gene can contain 8 exons. Exon 1 can encode a leader peptide, exons 2 and 3 can encode alpha1 and alpha2 domains, which can both bind a peptide, exon 4 can encode an alpha3 domain, exon 5 can encode a transmembrane region, and exons 6 and 7 can encode a cytoplasmic tail. Polymorphisms within exon 2 and exon 3 can be responsible for the peptide binding specificity of each class one molecule. Hundreds of HLA-A alleles have been described. Provided herein are polypeptide constructs comprising, for instance, γδ TCR or fragment or variant thereof with a pre-defined specificity that can be introduced into a cell. In certain cases, a γδ TCR can be specific to HLA-A or a residue thereof of Table 1 and/or one or more of its polymorphisms. Preferably a γδ TCR can be specific to and bind the identity of at least 65%, 70%, 75%, 80%, 85%, 90%, 95%, 97%, 98%, 99% or 100% of SEQ ID NO: 1.

TABLE 1

HLA-A

| SEQ ID NO: | Abbrev. | Name | NCBI No: GRCh38.p7 | Genomic sequence |
|---|---|---|---|---|
| 1 | HLA-A | major histo-compatibility complex, class I, A | 3105 | GAGAAGCCAATCAGTGTCGTCGCGGTCGCTGTTCTA AAGTCCGCACGCACCCACCGGGACTCAGATTCTCCC CAGACGCCGAGGATGGCCGTCATGGCGCCCCGAACC CTCCTCCTGCTACTCTCGGGGGCCCTGGCCCTGACC CAGACCTGGGCGGGTGAGTGCGGGGTCGGGAGGGAA ACCGCCTCTGCGGGGAGAAGCAAGGGGCCCTCCTGG CGGGGGCGCAGGACCGGGGGAGCCGCGCCGGGAGGA GGGTCGGGCAGGTCTCAGCCACTGCTCGCCCCCAGG CTCCCACTCCATGAGGTATTTCTTCACATCCGTGTC |

TABLE 1-continued

HLA-A

| SEQ ID NO: | Abbrev. Name | NCBI No: GRCh38.p7 | Genomic sequence |
|---|---|---|---|
| | | | CCGGCCCGGCCGCGGGGAGCCCCGCTTCATCGCCGT |
| | | | GGGCTACGTGGACGACACGCAGTTCGTGCGGTTCGA |
| | | | CAGCGACGCCGCGAGCCAGAAGATGGAGCCGCGGGC |
| | | | GCCGTGGATAGAGCAGGAGGGGCCGGAGTATTGGGA |
| | | | CCAGGAGACACGGAATATGAAGGCCCACTCACAGAC |
| | | | TGACCGAGCGAACCTGGGGACCCTGCGCGGCTACTA |
| | | | CAACCAGAGCGAGGACGGTGAGTGACCCCGGCCCGG |
| | | | GGCGCAGGTCACGACCCCTCATCCCCCACGGACGGG |
| | | | CCAGGTCGCCCACAGTCTCCGGGTCCGAGATCCACC |
| | | | CCGAAGCCGCGGGACTCCGAGACCCTTGTCCCGGGA |
| | | | GAGGCCCAGGCGCCTTTACCCGGTTTCATTTTCAGT |
| | | | TTAGGCCAAAAATCCCCCGGGTTGGTCGGGGCGGG |
| | | | GCGGGGCTCGGGGACTGGGCTGACCGCGGGGTCGG |
| | | | GGCCAGGTTCTCACACCATCCAGATAATGTATGGCT |
| | | | GCGACGTGGGGCCGGACGGGCGCTTCCTCCGCGGGT |
| | | | ACCGGCAGGACGCCTACGACGGCAAGGATTACATCG |
| | | | CCCTGAACGAGGACCTGCGCTCTTGGACCGCGGCGG |
| | | | ACATGGCAGCTCAGATCACCAAGCGCAAGTGGGAGG |
| | | | CGGTCCATGCGGCGGAGCAGCGGAGAGTCTACCTGG |
| | | | AGGGCCGGTGCGTGGACGGGCTCCGCAGATACCTGG |
| | | | AGAACGGGAAGGAGACGCTGCAGCGCACGGGTACCA |
| | | | GGGGCCACGGGCGCCTCCCTGATCGCCTATAGATC |
| | | | TCCCGGGCTGGCCTCCCACAAGGAGGGGAGACAATT |
| | | | GGGACCAACACTAGAATATCACCCTCCCTCTGGTCC |
| | | | TGAGGGAGAGGAATCCTCCTGGGTTTCCAGATCCTG |
| | | | TACCAGAGAGTGACTCTGAGGTTCCGCCCTGCTCTC |
| | | | TGACACAATTAAGGGATAAAATCTCTGAAGGAGTGA |
| | | | CGGGAAGACGATCCCTCGAATACTGATGAGTGGTTC |
| | | | CCTTTGACACCGGCAGCAGCCTTGGGCCCGTGACTT |
| | | | TTCCTCTCAGGCCTTGTTCTCTGCTTCACACTCAAT |
| | | | GTGTGTGGGGGTCTGAGTCCAGCACTTCTGAGTCTC |
| | | | TCAGCCTCCACTCAGGTCAGGACCAGAAGTCGCTGT |
| | | | TCCCTTCTCAGGGAATAGAAGATTATCCCAGGTGCC |
| | | | TGTGTCCAGGCTGGTGTCTGGGTTCTGTGCTCTCTT |
| | | | CCCCATCCCGGGTGTCCIGTCCATTCTCAAGATGGC |
| | | | CACATGCGTGCTGGTGGAGTGTCCCATGACAGATGC |
| | | | AAAATGCCTGAATTTTCTGACTCTTCCCGTCAGACC |
| | | | CCCCCAAGACACATATGACCCACCACCCCATCTCTG |
| | | | ACCATGAGGCCACCCTGAGGTGCTGGGCCCTGGGCT |
| | | | TCTACCCTGCGGAGATCACACTGACCTGGCAGCGGG |
| | | | ATGGGGAGGACCAGACCCAGGACACGGAGCTCGTGG |
| | | | AGACCAGGCCTGCAGGGGATGGAACCTTCCAGAAGT |
| | | | GGGCGGCTGTGGTGGTGCCTTCGGAGAGGAGCAGA |
| | | | GATACACCTGCCATGTGCAGCATGAGGGTCTGCCCA |
| | | | AGCCCCTCACCCTGAGATGGGTAAGGAGGGAGATG |
| | | | GGGGTGTCATGTCTCTTAGGGAAAGCAGGAGCCTCT |
| | | | CTGGAGACCTTTAGCAGGGTCAGGGCCCCTCACCTT |
| | | | CCCCTCTTTTCCCAGAGCTGTCTTCCCAGCCCACCA |
| | | | TCCCCATCGTGGGCATCATTGCTGGCCTGGTTCTCC |
| | | | TTGGAGCTGTGATCACTGGAGCTGTGGTCGCTGCCG |
| | | | TGATGTGGAGGAGGAAGAGCTCAGGTGGAGAAGGGG |
| | | | TGAAGGGTGGGGTCTGAGATTTCTTGTCTCACTGAG |
| | | | GGTTCCAAGCCCCAGCTAGAAATGTGCCCTGTCTCA |
| | | | TTACTGGGAAGCACCTTCCACAATCATGGGCCGACC |
| | | | CAGCCTGGGCCCTGTGTGCCAGCACTTACTCTTTTG |
| | | | TAAAGCACCTGTTAAAATGAAGGACAGATTTATCAC |
| | | | CTTGATTACGGCGGTGATGGGACCTGATCCCAGCAG |
| | | | TCACAAGTCACAGGGGAAGGTCCCTGAGGACAGACC |
| | | | TCAGGAGGGCTATTGGTCCAGGACCCACACCTGCTT |
| | | | TCTTCATGTTTCCTGATCCCGCCCGGGTCTGCAGT |
| | | | CACACATTTCTGGAAACTTCTCTGGGGTCCAAGACT |
| | | | AGGAGGTTCCTCTAGGACCTTAAGGCCCTGGCTCCT |
| | | | TTCTGGTATCTCACAGGACATTTTCTTCCCACAGAT |
| | | | AGAAAAGGAGGGAGTTACACTCAGGCTGCAAGTAAG |
| | | | TATGAAGGAGGCTGATGCCTGAGGTCCTTGGGATAT |
| | | | TGTGTTTGGGAGCCCATGGGGGAGCTCACCCACCCC |
| | | | ACAATTCCTCCTCTAGCCACATCTTCTGTGGGATCT |
| | | | GACCAGGTTCTGTTTTTGTTCTACCCCAGGCAGTGA |
| | | | CAGTGCCCAGGGCTCTGATGTGTCTCTCACAGCTTG |
| | | | TAAAGGTGAGAGCTTGGAGGGCCTGATGTGTGTTGG |
| | | | GTGTTGGGTGGAACAGTGGACACAGCTGTGCTATGG |
| | | | GGTTTCTTTGCGTTGGATGTATTGAGCATGCGATGG |
| | | | GCTGTTTAAGGTGTGACCCCTCACTGTGATGGATAT |
| | | | GAATTTGTTCATGAATATTTTTTTCTATAGTGTGAG |

TABLE 1-continued

HLA-A

| SEQ ID NO: | Abbrev. Name | NCBI No: GRCh38.p7 | Genomic sequence |
|---|---|---|---|
| | | | ACAGCTGCCTTGTGTGGGACTGAGAGGCAAGAGTTG |
| | | | TTCCTGCCCTTCCCTTTGTGACTTGAAGAACCCTGA |
| | | | CTTTGTTTCTGCAAAGGCACCTGCATGTGTCTGTGT |
| | | | TCGTGTAGGCATAATGTGAGGAGGTGGGGAGAGCAC |
| | | | CCCACCCCCATGTCCACCATGACCCTCTTCCCACGC |
| | | | TGACCTGTGCTCCCTCTCCAATCATCTTTCCTGTTC |
| | | | CAGAGAGGTGGGGCTGAGGTGTCTCCATCTCTGTCT |
| | | | CAACTTCATGGTGCACTGAGCTGTAACTTCTTCCTT |
| | | | CCCTATTAAAATTAGAACCTGAGTATAAATTTACTT |
| | | | TCTCAAATTCTTGCCATGAGAGGTTGATGAGTTAAT |
| | | | TAAAGGAGAAGATTCCTAAAATTTGAGAGACAAAAT |
| | | | TAATGGAACGCATGAGAACCTTCCAGAGTCCA |

Provided herein is a polypeptide construct comprising a γδ TCR or fragment or variant thereof that can bind HLA-A*24:02. In some cases, a γδ TCR or fragment or variant thereof described herein can be expressed in an engineered αβ T cell. In some cases, a polypeptide construct comprising a γδ TCR or fragment or variant thereof that is HLA-restricted may only bind HLA expressed on a cancer and not on a healthy tissue. A healthy or normal tissue that can express HLA-A can be an adrenal, appendix, bone marrow, brain, colon, duodenum, endometrium, esophagus, fat, gall bladder, heart, kidney, liver, lung, lymph node, ovary, pancreas, placenta, prostate, salivary gland, skin, small intestine, spleen, stomach, testis, thyroid, urinary bladder, or any combination thereof. In some cases, an HLA-A protein can be differentially expressed on a cancer relative to its expression on a healthy tissue. In some cases, HLA-A expression on a cancer can be an aberrant expression of HLA-A. An aberrant expression can include aberrations in terms of mobility, flexibility, folding, and/or compartimentalization as compared to HLA expressed on a comparable cell. For example, a cancer cell can have aberrant expression of HLA-A as compared to a non-cancerous comparable cell. An aberrant expression can include differences in mobility of an HLA-A on a cancer cell surface that can influence binding of a TCR. Similarly an aberrant expression can influence flexibility of an HLA protein, such as HLA-A, on a cancer cell. Aberrant expressions of HLA-A on target cells can create unique binding sites or unique binding comformations that may not be present on comparable cells. Compositions disclosed herein can include polypeptide constructs engineered to harness aberrant HLA-A expressions, or engineered cells expressing such polypeptide constructs, to provide tumor-targeted therapies with reduced off-target binding.

In some cases, a polypeptide construct disclosed herein can comprise a γδ TCR or fragment or variant thereof that can be specific to HLA-A and/or one or more of its polymorphisms expressed on a tumor and not on a healthy tissue. In some cases, a polypeptide construct disclosed herein can comprise a γδ TCR or fragment or variant thereof that can be specific to HLA-A*24:02 and any of its alleles expressed on a tumor and not on a healthy tissue. In some cases, a polypeptide construct described herein can be specific to one or more HLA-A configurations expressed on a tumor and not on a healthy tissue. In some cases, a polypeptide construct may be specific to HLA-A*24:02 expressed on a tumor and not on a healthy tissue. A polypeptide construct can recognize and bind a malignant transformed cell. In some cases, a malignant transformed cell can be HLA-A*24:02 positive. In some cases, a γδ TCR binds a CD8 binding site of an HLA-A*24 protein. In some cases, a residue that can be bound can be W107, A185, S207, and any combination thereof. In some cases, a residue that can be bound can be G, P and G, and any combination thereof. In some cases, a C-terminal residue of an HLA-A*24 protein can be bound. In other cases, an N-terminus residue of an HLA-A*24 protein can be bound. In some cases, a γδ TCR can bind a peptide binding cleft of an HLA-A*24 protein. In some cases, a γδ TCR can bind an "A" pocket of a peptide binding cleft.

A polypeptide construct described herein can comprise at least one receptor chain comprising or consisting of, or being derived from, a sequence disclosed in any one of Table 2, Table 4, Table 5, and Table 6 or a portion thereof. Disclosed herein can be an antigen binding unit, such as a γδ TCR or portion thereof, comprising at least one CDR. In some aspects, an antigen binding unit can comprise a light chain CDR. A light chain CDR can be a complementarity determining region of a light chain of an antigen binding unit. A light chain CDR can comprise a continuous sequence of amino acid residues, or two or more contiguous sequences of amino acid residues separated by, and optionally flanked by, non-complementarity determining regions, such as framework regions. In some examples, a light chain CDR comprises two or more light chain CDRs, which can be referred to as light chain CDR-1, CDR-2, and so on. In some aspects, an antigen binding unit can comprise a heavy chain CDR. A heavy chain CDR can be a complementarity determining region of a heavy chain of an antigen binding unit. A heavy chain CDR can comprise a continuous sequence of amino acid residues, or two or more contiguous sequences of amino acid residues separated by, and optionally flanked by, non-complementarity determining regions, such as framework regions. In some examples, a heavy chain CDR comprises two or more heavy chain CDRs, which can be referred to as heavy chain CDR-1, CDR-2, and so on. In some cases, a CDR3 sequence may be utilized. Disclosed herein can also be methods of generating CDR sequences, such as CDR3 sequences that can bind a target. For example, an FE11-like CDR3 sequence can be generated. An FE11 or FE11-like CDR3 sequence can be an antibody or binding portion thereof that can bind an HLA-A*24. An FE11-like CDR3 sequence can be an antibody or binding portion thereof that shares at least a portion of homology with an FE11 polypeptide or encoding nucleic acid molecule. In some cases, an FE11-like CDR3 sequence may have a difference in comformation, binding, amino acid sequence, or a difference in a portion of a sequence. An activity of a reference FE11 is retained to at least some extent in said FE11 or FE11-like CDR3 sequence. An activity of a reference FE11 may be the binding to HLA-A*24. Such a binding can be assessed using techniques known to a skilled person. Within this context "at least some extent" may mean at least 50%, at least 60%, at least 70%, at least 80%, at least 90% or at least 100% or more. Another activity of an FE11 or FE11-like CDR3 sequence can an anti-tumor or anti-cancer or anti-infectious activity or response.

An anti-tumor response may be assessed by contacting T cells expressing a gamma and/or delta sequence as identified herein with tumor cells (i.e. so-called engineered T cells). It is clear to a skilled person that said T cells used should also express a γT cell receptor chain in order to assess the biological relevance of a δT cell receptor chain. In other words a γδTCR is preferably expressed in said T cells, the δTCR being the one identified herein. Alternatively a γδTCR is preferably expressed in said T cells, the γTCR being the one identified herein. Alternatively, a γδTCR is preferably expressed in said T cells, each of the TCR chains being the ones identified herein. In a preferred embodiment, the nucleic acid molecule encoding the δT-cell (or γT-cell) receptor chain or part thereof is provided in an expression vector or in a retroviral or lentiviral vector in a T cell. The T cells may be expanded before or after the transfer of the nucleic acids encoding the δT-and/or γT-cell receptor chain. Preferably, the expansion is after the transfer such that the amount of nucleic acids that needs to be transferred is as low as possible. This expansion of said T cells may be performed by stimulation with anti-CD3/CD28 Dynabeads in the presence of IL-2. The expanded cells comprising the engineered γδ T-cell receptor, may be selected e.g. via a selectable marker and may be further selected for the presence of the CD4 antigen and the CD8 antigen, e.g. using the MACS separating system as described in the examples. The engineered T-cells may be subsequently further expanded using the REP protocol as described by Riddel and Greenberg, 1990 J Immunol Methods. 128(2): 189-201, which is incorporated herein by reference, or using similar further expansion methods thereto. Briefly, the expansion method involves using antibodies directed against T cell activation molecules, such as TCR, CD3 and CD28 and/or feeder cells and/or stimulating cytokines.

The anti-tumor response of said T-cell expressing a δT-cell (or γT-cell) receptor chain may be assessed using any technique known to the skilled person. A δT-cell receptor chain may be a δ2-T cell receptor chain. A γT-cell receptor chain may be a γ9-T cell receptor chain. The step of determining an anti-tumor activity may include any assay in which an anti-tumor effect may be determined, such as having an effect on tumor cell division rate, i.e. the speed with which the tumor cells divide, cell death, binding to the tumor cells, induction of the production of a cytokine such as IFNγ, IL-2 or TNFα. Tumor cells may be any kind of tumor cells. For example, primary tumor cells from a patient. The tumor cells may be tumor cells from cell lines, such as the cell lines listed in the examples named Daudi, RPMI8226/S, OPM2, LME1, K562, Saos2, MZ1851 RC, SCC9, Fadu, MDA-MB231, MCF7, BT549, SW480, which are well known in the art. Tumor cell lines may easily be obtained from the American Type Culture Collection (ATCC, Manassas, Va.) and the like.

In a preferred embodiment, determining the anti-tumor responses includes contacting said engineered T cell with a tumor cell and measuring its ability to lyse the tumor cell and/or induce the production of a cytokine such as IFN-γ, IL-2 or TNFα. This contacting, culturing or incubation step may have a duration from 10 hours to 1, 2, 3, 4, 5 days. The ability to lyse the tumor cells include providing a fixed amount of tumor cells with which said T cell is contacted and after an incubation period the number of viable tumor cells is counted. An anti-tumor response may have been identified or determined when the number of viable tumor cells at the end of the incubation step is less than 90%, less than 80%, less than 70%, less than 60%, less than 50%, less than 40%, less than 30%, less than 20%, less than 10% of the number of initial tumor cells at the onset of the incubation step. Alternatively, an anti-tumor response may have been identified or determined when the number of viable tumor cells at the end of the incubation step with the engineered T cells is lower than the number of tumor cells at the end of a similar incubation step with control T cells not engineered with sequences identified as shared. Lower in this context may mean at least 10% lower, at least 20% lower, at least 30% lower, at least 40% lower, at least 50% lower, at least 60% lower, at least 70% lower, at least 80% lower, at least 90% lower.

In addition or as alternative to the counting of the number of viable tumor cells at the end of the incubation step, one may also perform a $^{51}$Chromium-release assay which is known to the skilled person. The amount of $^{51}$Chromium release is a measure of the number of cells that have been lysed. Similarly, the production of a cytokine such as IFN-γ, IL-2 or TNFα or the secretion or the expression of activation markers may also be determined, e.g. via antibody staining, ELISA and/or quantitative PCR for the expressed mRNA. Assays for determining the production of a cytokine such as IFN-γ, IL-2 or TNFα are commercially widely available. When the production of a cytokine such as IL-2, TNFα or IFNγ is detected, said T cell is said to exhibit an anti-tumor response. Alternatively and preferably, when the amount of IFNγ, IL-2 or TNFα produced at the end of the contacting step with engineered T cells is higher (preferably at least 10%, at least 20%, at least 30%, at least 40%, at least 50%, at least 60%, at least 70%, at least 80%, at least 90%, at least 100% or more) than the amount of IFNγ IL-2 or TNFα produced when tumor cells are contacted with control T cells, the T cells is said to exhibit an anti-tumor response. Control T cells do not express a defined nucleic acid molecule encoding an amino acid comprising a δT-cell (or γT-cell) receptor chain identified herein. An anti-tumor response may also be determined by assessing the binding of the engineered T cells to the tumor cell at the end of the incubation step. When binding of the engineered T cell to the tumor cell is detected at the end of the contacting step, the T cell is said to exhibit an anti-tumor response. Alternatively and preferably, when the binding of the T cell at the end of the contacting step is higher (preferably at least 10%, at least 20%, at least 30%, at least 40%, at least 50%, at least 60%, at least 70%, at least 80%, at least 90%, at least 100% or more) than the binding of control T cells (see earlier definition) to the same tumor cell, the T cells is said to exhibit an anti-tumor response. The contacting step may be carried out in the presence of a phosphoantigen, such as pamidronate.

Methods of generating CDR sequences that can bind a target can include mutations, subsitutions, deletions, insertions, among other techniques. For example, an FE11-like CDR3 sequence can be generated by amino acid substitution. Any number of amino acids can be substituted. Amino acid subsitutations can include from about 1 to about 1000. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, or up to about 1000 amino acids can be substituted. A number of amino acid substitutions may also be defined in one of the following ways: as having at least 1 substituted amino acid per 10, 15, 20, 25 amino acids present in the molecule considered, as having at least 1%, at least 5%, at least 10%, at least 15% of substituted amino acids.

Amino acid subsitutions can have various effects on a CDR region. In some cases, a subsitutions or mutation can affect a stability of a domain. In other cases, a subsitutions or mutation can affect a level of expression. A substitution or mutation of a CDR region, such as CDR3, can affect a structure. Changes to a CDR3 region can include a variable domain, a constant domain, or a combination thereof. In some cases, a substitution or mutation can affect ligand binding. A substitution, mutation, deletion, or insertion can be performed on at least a portion of a Jγ1 and/or Jδ1 segment. In some cases, a substitution or mutation can affect ligand binding. A substitution, mutation, deletion, or insertion can be performed on on a C terminus, N terminus, or both termini of an amino acid sequence. In some cases, a mutated polypeptide or a polypeptide with at least one substitution by comparison to a reference polypeptide, said mutated polypeptide can include any one of SEQ ID NO: 2 to SEQ ID NO: 428. In a preferred embodiment, there is provided a polypeptide which is represented by an amino acid sequence, said amino acid sequence comprising at least 60% sequence identity or similarity with any of amino acid sequence SEQ ID NO: 2, SEQ ID NO: 3, amino acids 19-309 of SEQ ID NO: 4, amino acids 21-293 of SEQ ID NO: 5, SEQ ID NO: 4, SEQ ID NO: 5 and SEQ ID NO: 6 to SEQ ID NO: 428. Preferably, the identity is of at least 65%, 70%, 75%, 80%, 85%, 90%, 95%, 97%, 98%, 99% or 100%.

In some cases, an engineered cell can comprise at least a portion or a part of a receptor that is encoded by a sequence that is at least 50%, 55%, 60%, 65%, 70%, 75%, 80%, 85%, 90%, 95%, 96%, 97%, 98%, or 99% identical to at least one of SEQ ID NO: 6 to SEQ ID NO: 428. Preferably the identity is assessed over the whole length. In some cases, a mutant sequence can be found within a gamma or delta chain of a TCR.

In certain methods disclosed herein, a CDR3 region of a γ9T-cell receptor or γ9 negative γT-cell receptor chain and the δ2T-cell receptor or δ2 negative δT-cell receptor chain can be modified and combined to form a novel γ9δ2TCR that selectively binds an HLA conformation disclosed herein. In a more preferred embodiment, there is provided a δT-cell receptor chain or part thereof comprising a CDR3 region, said δT-cell receptor chain or part thereof being represented by an amino acid sequence, said amino acid sequence comprising at least 60% sequence identity or similarity with any one of amino acid sequence SEQ ID NO: 6 to 237. Preferably, the identity is of at least 65%, 70%, 75%, 80%, 85%, 90%, 95%, 97%, 98%, 99% or 100%. In another more preferred embodiment, there is provided a γT-cell receptor chain or part thereof comprising a CDR3 region, said γT-cell receptor chain or part thereof being represented by an amino acid sequence, said amino acid sequence comprising at least 60% sequence identity or similarity with any one of amino acid sequence SEQ ID NO: 238 to 428. Preferably, the identity is of at least 65%, 70%, 75%, 80%, 85%, 90%, 95%, 97%, 98%, 99% or 100%.

In certain embodiments, are polypeptide constructs comprising a γ9 negative γT-cell receptor chain, a δ2T-cell receptor, and/or, a δ2 negative δT-cell receptor chain. The designed γδTCR can be provided and preferably integrated into T-cells, which can subsequently express a γδTCR at the cell surface. Accordingly the anti-tumor response of the CTE-engineered T-cells is determined. In this way multiple combinations can be tested, and for each combination the anti-tumor response can be determined. After determining an anti-tumor response, γ9δ2T-cell receptors that mediate highly active anti-tumor responses can be identified. In certain methods disclosed herein, a CDR3 region of a γ5T-cell receptor chain and the δ1T-cell receptor chain can be modified and combined to form a novel γ5δ1TCR that selectively binds an HLA conformation disclosed herein. In certain embodiments, are polypeptide constructs comprising γ5T-cell receptor chains and/or MT-cell receptor chains disclosed in one or more of Tables 2, 4 and 5. The designed γ5δ1TCR can be provided and preferably integrated into T-cells, which subsequently express a γ5δ1TCR at the cell surface. Accordingly the anti-tumor response of the CTE-engineered T-cells is determined. In this way multiple combinations can be tested, and for each combination the anti-tumor response can be determined. After determining an anti-tumor response, γ5δ1T-cell receptors that mediate highly active anti-tumor responses can be identified. Accordingly, there is provided a TCR, preferably an engineered TCR comprising: a δT-cell receptor chain or part thereof comprising a CDR3 region, said δT-cell receptor chain or part thereof being represented by an amino acid sequence, said amino acid sequence comprising at least 60% sequence identity or similarity with any one of amino acid sequence SEQ ID NO: 3, and 6 to 237 and a γT-cell receptor chain or part thereof comprising a CDR3 region, said γT-cell receptor chain or part thereof being represented by an amino acid sequence, said amino acid sequence comprising at least 60% sequence identity or similarity with any one of amino acid sequence SEQ ID NO: 2, and 238 to 428. Preferably, the identity is of at least 65%, 70%, 75%, 80%, 85%, 90%, 95%, 97%, 98%, 99% or 100%. In some aspects of any of the embodiments disclosed herein, a subject antigen binding unit specifically binds to at least a portion of HLA-A*24:02. HLA-A*24:02 as used herein can also refer to orthologues, homologues, codon-optimized forms, truncated forms, fragmented forms, mutated forms, or any other known derivative form of a known HLA-A*24:02 sequence. For example, HLA-A*24:02 can be human HLA-A*24:02. HLA-A*24:02 can be murine HLA-A*24:02. In some cases, an MHC can be from a mammal such as a chimpanzee, pig, gorilla, chicken, cow, goat, to name a few.

In some cases a γδ TCR can comprise homology to SEQ ID NO: 2, amino acids 19-309 of SEQ ID NO: 4, SEQ ID NO:4 or SEQ ID NOs: 238-428 from Table 6, from about or from 10%, 15%, 20%, 25%, 30%, 35%, 40%, 45%, 50%, 55%, 60%, 65%, 70%, 75%, 80%, 85% 90%, 91%, 92%, 93%, 94%, 95%, 96%, 97%, 98%, 99% or up to 100%. In some cases a γδ TCR can comprise homology to SEQ ID NO: 3, amino acids 21-293 of SEQ ID NO: 5, SEQ ID NO: 5 or SEQ ID NOs: 6-237 from Table 5, from about 10%, 15%, 20%, 25%, 30%, 35%, 40%, 45%, 50%, 55%, 60%, 65%, 70%, 75%, 80%, 85% 90%, 91%, 92%, 93%, 94%, 95%, 96%, 97%, 98%, 99% or up to 100%. In some cases, a γδ TCR can comprise both amino acids 19-309 of SEQ ID NO: 4 and amino acids 21-293 of SEQ ID NO: 5. In some cases, a γδ TCR can comprise sequences from Table 5 and Table 6.

A polypeptide described herein can be utilized to selectively bind a conformationally constrained HLA molecule. For example, a conformationally constrained HLA molecule can include an HLA with an aberrant conformation, an HLA expressed on a tumor cell, as compared to a normal HLA molecule on a comparable cell. In specific embodiments, a polypeptide construct described herein can bind an HLA molecule expressed on a cancer cell selectively as compared to corresponding HLA molecule on non-cancer cells. In some cases, an HLA expressed by a cancer can be conformationally different as compared to a HLA expressed on a healthy tissue. For example, a malignancy may cause HLA to form clustering on a tumor cell surface that may be recognized by a γδ TCR. Clustering on a tumor cell can induce a conformational change in an HLA that may make it detectable by a γδ TCR. Clustering on a cell surface may include contact of at least two HLA proteins. In some cases, clustering can include at least two HLA proteins that are adjacent to one another. In some cases, clustering can be measured by density of proteins on a cell surface.

A conformational change can create new binding sites on a HLA that may not be present when unclustered. In some cases, from 1 to 100 new binding sites may be present on a clustered HLA protein as compared to an unclustered protein. In some cases, 1, 5, 10, 15, 20, 25, 30, 35, 40, 45, 50, 55, 60, 65, 70, 75, 80, 85, 90, 95, 100 new binding sites may be present. In some cases, a γδ TCR can bind a new binding site on a clustered HLA protein. In some cases, a γδ TCR can bind a clustered HLA-A. In some cases, a γδ TCR can bind a clustered HLA-A*24. In some cases, a γδ TCR can bind a clustered HLA-A*24:02.

In some cases, HLA clustering can be displayed at the surfaces of tumor cells characterized by interreceptor distances in a micrometer range as detected by scanning force microscopy of immunogold-labeled antigens. In some cases, electron microscopy can be used to detect and measure HLA clustering on a cellular surface. In some cases, scanning force microscopy can be used to detect and measure clustering. In some cases, 30- and 15-nm immunogold beads can be utilized in a microscopy technique to measure and detect clustering. A bead of any size can be used such as from about 5 nm, 10 nm, 15 nm, 20 nm, 25 nm, 30 nm, 35 nm, 40 nm, 50 nm, 55 nm, 60 nm, 65 nm, 70 nm, 75 nm, 80 nm, 85 nm, 90 nm, 95 nm, or up to 100 nm in diameter. A bead can be substantially spherical in some cases. In some cases, clusterization of HLA can be detected by a distribution of antigens, beads, or peptides displayed therein as detected by a deviation of their spatial distribution from a Poissonian distribution representing a random case. Fluorescence resonance energy transfer (FRET) measurements can also be used to show clustering of HLA molecules at another hierarchical level. For example FRET characterized by from about 2- to 10-nm Förster distance range can provide fine details of a molecular organization of receptors. In other cases, a Förster distance range that can be used to detect an HLA cluster can be from about 0.5 nm, 1 nm, 1.5 nm, 2 nm, 2.5 nm, 3 nm, 3.5 nm, 4 nm, 4.5 nm, 5 nm, 5.5 nm, 6 nm, 6.5 nm, 7 nm, 7.5 nm, 8 nm, 8.5 nm, 9 nm, 9.5 nm, 10 nm, 10.5 nm, 11 nm, 11.5 nm, 12 nm, 12.5 nm, 13 nm, 13.5 nm, 14 nm, 14.5 nm, 15 nm, 15.5 nm, 16 nm, 16.5 nm, 17 nm, 17.5 nm, 18 nm, 18.5 nm, 19 nm, 19.5 nm, or up to about 20 nm.

Cellular Engineering

As part of a cellular engineering process or method a source of immune cells can be obtained from a subject. Immune cells can be from a myeloid or lymphoid origin. In some cases, T cells, B cells, or natural killer (NK) cells can be used. T cells may also be cell lines, such as SupT-1, Jurkat, or Raji cells or any other widely available cell line. Any cell type, being a primary cell or any other cell line can be utilized. In some cases, a cell that expresses a T cell receptor, i.e. such as being positive for an αβTCR in a FACS sorting may be contemplated. Also, any cell or cell population may be contemplated that, when provided with a γδTCR can be capable of forming a functional TCR complex and exerting e.g. a functional cytoxic response and/or cytokine production. A cell that can be provided may also be a progenitor cell, preferably a blood progenitor cell such as a thymocyte or a blood stem cell, which after it has been provided with the right stimuli can develop into T cells or engineered T cells. Hence it can be understood that providing a cell with a γδTCR may comprise providing progenitor cells, providing these with a γδTCR and stimulating these progenitor cells such that these develop into engineered T cells.

T cells can be obtained from a number of sources, including peripheral blood mononuclear cells (PBMCs), bone marrow, lymph node tissue, cord blood, thymus tissue, tissue from a site of infection, ascites, pleural effusion, spleen tissue, and tumors. Any number of T cell lines available in the art, may be used. T cells can be obtained from a unit of blood collected from a subject using any number of techniques known to the skilled artisan, such as Ficoll™ separation. In some cases, cells from the circulating blood of an individual are obtained by apheresis. A apheresis product typically contains lymphocytes, including T cells, monocytes, granulocytes, B cells, other nucleated white blood cells, red blood cells, and platelets, in one embodiment, the cells collected by apheresis may be washed to remove the plasma fraction and to place the cells in an appropriate buffer or media for subsequent processing steps. In some cases, cells are washed with phosphate buffered saline (PBS). In some cases, a wash solution may lack calcium and may lack magnesium or may lack many if not all divalent cations. A washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, isolated cells may be resuspended in a variety of biocompatible buffers, such as, for example, $Ca^{2+}$-free, $Mg^{2+}$-free PBS, PlasmaLyte A, or other saline solution with or without buffer. Alternatively, any undesirable components of a apheresis sample may be removed and the cells directly resuspended in culture media. In some cases, T cells can be isolated from peripheral blood lymphocytes by lysing the red blood cells and depleting the monocytes, for example, by centrifugation through a PERCOLL™ gradient or by counterflow centrifugal elutriation. A specific subpopulation of T cells, such as $CD3^+$, $CD28^+$, $CD4^+$, $CD8^+$, $CD45RA^+$, and $CD45RO^+$T cells, can be further isolated by positive or negative selection techniques. For example, in one embodiment, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In one embodiment, a time period is about 30 minutes. In some cases, a time period ranges from about 30 minutes to 36 hours or longer and all integer values there between. In a further embodiment, a time period is at least 1, 2, 3, 4, 5, or 6 hours. In another case, a time period is from about 10 hours to about 24 hours. In some cases, a time period can be 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immune-compromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process, Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention.

In some cases, enrichment of a T cell population by negative selection can be accomplished with a combination of antibodies directed to surface markers unique to the negatively selected cells. One method can be cell sorting and/or selection via negative magnetic immunoadherence or flow cytometry that may use a cocktail of monoclonal antibodies directed to cell surface markers present on the cells negatively selected. For example, to enrich for CD4+ cells by negative selection, a monoclonal antibody cocktail typically includes antibodies to CD 14, CD20, CD11b, CD 16, HLA-DR, and CD8, In certain embodiments, it may be desirable to enrich for or positively select for regulatory T cells which typically express $CD4^+$, $CD25^+$, CD62L+, $GITR^+$, and $FoxP3^+$. Alternatively, in certain embodiments, T regulatory cells can be depleted by anti-CD25 conjugated beads or other similar methods of selection.

For isolation of a desired population of cells by positive or negative selection, a concentration of cells and surface (e.g., particles such as beads) can be varied. In certain embodiments, it may be desirable to significantly decrease a volume in which beads and cells are mixed together (i.e., increase the concentration of cells), to ensure maximum contact of cells and beads. For example, in one embodiment, a concentration of 2 billion cells/ml can be used. In one embodiment, a concentration of 1 billion cells/ml can be used. In a further embodiment, greater than 100 million cells/ml can be used. In a further embodiment, a concentration of cells of 10, 15, 20, 25, 30, 35, 40, 45, or 50 million cells/ml can be used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. T cells for stimulation can also be frozen after a washing step.

A freeze and subsequent thaw step can provide a more uniform product by removing granulocytes and to some extent monocytes in a cell population. After a washing step that may remove plasma and platelets, cells may be suspended in a freezing solution, While many freezing solutions and parameters are known in the art and may be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmaiyte-A, 3 1.25% Dextrose 5%, 0.45% NaCl, 10% Dextran 40 and 5% Dextrose, 20% Human Serum Albumin, and 7.5% DMSO or other suitable ceil freezing media containing for example, Hespan and PlasmaLyte A, cells may then be frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen. In certain embodiments, cryopreserved cells may be thawed and washed as described herein and allowed to rest for one hour at room temperature prior to activation.

Also contemplated can be collection of blood samples or apheresis product from a subject at a time period prior to when the expanded cells as described herein might be needed. In one embodiment a blood sample or an apheresis can be taken from a generally healthy subject. In certain embodiments, a blood sample or an apheresis can be taken from a generally healthy subject who may be at risk of developing a disease, but who has not yet developed a disease and cells of interest can be isolated and frozen for later use. In some cases, T cells may be expanded, frozen, and used at a later time. In some cases, samples are collected from a patient shortly after diagnosis of a particular disease as described herein but prior to any treatments. In some cases, cells may be isolated from a blood sample or an apheresis from a subject prior to any number of relevant treatment modalities, including but not limited to treatment with agents such as natal izumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, Cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin).

In some cases, cells can be isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, cells can be isolated prior to and can be frozen for later use for treatment following B-cell ablative therapy such as agents that react with CD20, e.g., Rituxan.

In some cases, T cells can be obtained from a patient directly following treatment. In this regard, it has been observed that following certain cancer treatments, in particular treatments with drugs that damage the immune system, shortly after treatment during the period when patients would normally be recovering from the treatment, a quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types can be favored, especially during a defined window of time following therapy. Illustrative cell types include T cells, B cells, dendritic cells, and other cells of the immune system.

Following isolation of cells, immune cells, for instance T cells can be expanded by contact with a surface having attached thereto an agent that stimulates a CD3 TCR complex associated signal and a ligand that stimulates a co-stimulatory molecule on a surface of T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore, For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4$^+$ T cells or CD8$^+$ T cells, an anti-CD3 antibody and an anti-CD28 antibody. Examples of an anti-CD28 antibody include 9.3, B-T3, XR-CD28 (Diacione, Besancon, France) can be used as can other methods commonly known in the art (Berg et al., Transplant Proc. 30(8):3975-3977, 1998; Haanen et al., J. Exp. Med. 190(9): 13191328, 1999; Garland et al., J. Immunol Meth. 227(1-2):53-63, 1999).

In certain embodiments, a primary stimulatory signal and a co-stimulatory signal for T cells may be provided by different protocols. For example, agents providing each signal may be in solution or coupled to a surface. When coupled to a surface, agents may be coupled to the same surface (i.e., in "cis" formation) or to separate surfaces (i.e., in "trans" formation). Alternatively, one agent may be coupled to a surface and the other agent in solution. In one embodiment, an agent providing a co-stimulatory signal can be bound to a cell surface and an agent providing a primary activation signal may be in solution or coupled to a surface. In certain embodiments, both agents can be in solution. In another embodiment, an agent may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In some cases, a culture media that can be used to grow cells described herein can include a number of addivites. In some instances, an additive can include chemokines, interferons, interleukins, colony-stimulating factors or tumor necrosis factors. In some cases, chemokines play a role as a chemoattractant to guide the migration of cells, and is classified into four subfamilies: CXC, CC, CX3C, and XC. Exemplary chemokines include chemokines from the CC subfamily: CCL1, CCL2 (MCP-1), CCL3, CCL4, CCL5 (RANTES), CCL6, CCL7, CCL8, CCL9 (or CCL10), CCL11, CCL12, CCL13, CCL14, CCL15, CCL16, CCL17, CCL18, CCL19, CCL20, CCL21, CCL22, CCL23, CCL24, CCL25, CCL26, CCL27, and CCL28; the CXC subfamily: CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, and CXCL17; the XC subfamily: XCL1 and XCL2; and the CX3C subfamily CX3CL1. Interferons (IFNs) can comprise interferon type I (e.g. IFN-α, IFN-β, IFN-ε, IFN-κ, and IFN-ω), interferon type II (e.g. IFN-γ), and interferon type III. In some embodiments, IFN-α is further classified into about 13 subtypes including IFNA1, IFNA2, IFNA4, IFNA5, IFNA6, IFNA7, IFNA8, IFNA10, IFNA13, IFNA14, IFNA16, IFNA17, and IFNA21. Interleukins can be expressed by leukocytes or white blood cells and they promote the development and differentiation of T and B lymphocytes and hematopoietic cells. Exemplary interleukines include IL-1, IL-2, IL-3, IL-4, IL-5, IL-6, IL-7, IL-8 (CXCL8), IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-35, and IL-36. In some cases, a tumor necrosis factors (TNFs) can be introduced to a culture media. TNFs can be a group of cytokines that modulate apoptosis. In some instances, there are about 19 members within the TNF family, including, not limited to, TNFα, lymphotoxin-alpha (LT-alpha), lymphotoxin-beta (LT-beta), T cell antigen gp39 (CD40L), CD27L, CD30L, FASL, 4-1BBL, OX40L, and TNF-related apoptosis inducing ligand (TRAIL).Colony-stimulating factors (CSFs) can be secreted glycoproteins that interact with receptor proteins on the surface of hemopoietic stem cells, which subsequently modulates cell proliferation and differentiation into specific kind of blood cells. In some instances, a CSF comprises macrophage colony-stimulating factor, granulocyte macrophage colony-stimulating factor (GM-CSF), granulocyte colony-stimulating factor (G-CSF) or promegapoietin.

In some cases, a polypeptide encoding a gamma-delta TCR can be introduced into an immune cell. Immune cells expressing exogenous gamma-delta TCRs can be expanded. In some cases, a method of engineering an immune cell can comprise providing a cell and expressing at the surface of a cell at least one exogenous gamma-delta TCR. Polynucleotides encoding a gamma-delta TCR may be introduced into a cell by for example, recombinant viral vectors (e.g. retroviruses, lentivimses, adenoviruses), liposome and the like. For example, transient transformation methods can include for example microinjection, electroporation or particle bombardment. A polynucleotide encoding a gamma-delta TCR can be introduced virally or nonvirally. Viral introductions can utilize retroviral vectors, lentiviral vectors, adenoviral vectors, or a combination thereof.

Provided herein can also be vectors in which a polynucleic acid can be inserted. Vectors derived from retroviruses such as the lentivirus are suitable tools to achieve long-term gene transfer since they can allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

A polynucleotide vector useful for the methods and compositions described herein can be a good manufacturing practices (GMP) compatible vector. For example, a GMP vector can be purer than a non-GMP vector. In some cases, purity can be measured by bioburden. For example, bioburden can be the presence or absence of aerobes, anaerobes, sporeformers, fungi, or combinations thereof in a vector composition. In some cases, a pure vector can be endotoxin low or endotoxin free. Purity can also be measured by double-stranded primer-walking sequencing. Plasmid identity can be a source of determining purity of a vector. A GMP vector of the invention can be from 10% to 99% more pure than a non-GMP vector. A GMP vector can be from 10%, 15%, 20%, 25%, 30%, 35%, 40%, 45%, 50%, 55%, 60%, 65%, 70%, 75%, 80%, 85%, 90%, 95%, 96%, 97%, 98%, or 99% more pure than a non-GMP vector as measured by the presence of bioburden, endotoxin, sequencing, or combinations thereof.

Provided can also be a nucleic acid sequence encoding a γδ TCR. A nucleic acid can be an isolated nucleic acid. A nucleic acid that can encode a γδ TCR can be in DNA or RNA form. For example, provided herein can be a DNA vector encoding a γδ TCR. Provided herein can also be a DNA minicircle encoding a γδ TCR. In some cases a γδ TCR can be in the form of mRNA. For example, cells can be electroporated with an mRNA encoding for a γδ TCR. A nucleic acid can be double stranded or single stranded. A single stranded nucleic acid can be short linear DNA (doggy bone) vector.

A nucleic acid can be cloned into a number of types of vectors. For example, a nucleic acid can be cloned into a vector including, but not limited to a plasmid, a phagemid, a phage derivative, an animal virus, and a cosmid. Vectors of can also include expression vectors, replication vectors, probe generation vectors, and sequencing vectors. Further, an expression vector may be provided to a cell in the form of a viral vector. Viral vector technology is well known in the art and is described, for example, in Sambrook et al, (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of a subject either in vivo or ex vivo. A number of retroviral systems are known in the art. In some embodiments, adenovirus vectors are used. A number of adenovirus vectors are known in the art. In one embodiment, lentivirus vectors are used. Additional promoter elements, e.g., enhancers, can regulate a frequency of transcriptional initiation. Typically, these are located in the region 30-110 bp upstream of a start site, although a number of promoters have recently been shown to contain functional elements downstream of a start site as well. The spacing between promoter elements frequently is flexible, so that promoter function can be preserved when elements are inverted or moved relative to one another. Depending on a promoter, individual elements can function either cooperatively or independently to activate transcription. One example of a suitable promoter can be the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1 a (EF-1 a). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, inducible promoters are also contemplated. An inducible promoter can provide a molecular switch capable of turning on expression of a polynucleotide sequence which it can operatively link when such expression is desired, or turning off the expression when expression is not desired. Examples of inducible promoters include, but are not limited to a metalothionine promoter, a glucocorticoid promoter, a progesterone promoter, and a tetracycline promoter. In order to assess the expression of a gamma-delta polypeptide or portions thereof, an expression vector to be introduced into a cell can also contain either a selectable marker gene or a reporter gene or both to facilitate identification and selection of expressing cells from the population of cells sought to be transfected or infected through viral vectors, in other aspects, a selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neomycin, green fluorescent protein (GFP), eGFP, luciferase, GUS, and the like.

Reporter genes are also used for identifying potentially transfected cells and for evaluating the functionality of regulatory sequences. Suitable reporter genes may include genes encoding luciferase, beta-galactosidase, chloramphenicol acetyl transferase, secreted alkaline phosphatase, or the green fluorescent protein gene. Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to mod late promoter-driven transcription. Methods of introducing and expressing genes into a cell are known in the art. In the context of an expression vector, the vector can be readily introduced into a host cell, e.g., mammalian, bacterial, yeast, or insect cell by any method in the art. For example, an expression vector can be transferred into a host cell by physical, chemical, or biological means. Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). A method for the introduction of a polynucleotide into a host cell can be calcium phosphate transfection. Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

In some cases, a terminator sequence at the end of a first gene program can be used. A terminator sequence can ensure that a transcript is terminating prior to initiating a second gene program. For example, an expression vectors can contain sequences necessary for the termination of transcription and for stabilizing an mRNA. Such sequences are commonly available from the 5' and, occasionally 3', untranslated regions of eukaryotic or viral DNAs or cDNAs. These regions can contain nucleotide segments transcribed as polyadenylated fragments in the untranslated portion of the mRNA. Cells comprising the expression vector are grown under conditions that provide for expression of the desired polypeptide, either in vivo or in vitro.

In some cases, a spacer sequence can be used at the end of a first polypeptide encoded by a polynucleotide in a vector. In other cases, a spacer sequence can be used at the end of a second gene in a vector. A spacer sequence can also be used following a first gene and a second gene in a vector.

These vectors can be used to express a polypeptide encoded by a gene, or portion of a gene of interest. A gene of portion or a gene can be inserted by using any method, viral or non-viral. For example; a method can be a non-viral based technique.

Regardless of the method used to introduce exogenous nucleic acids into a host cell or otherwise expose a cell to a polypeptide construct described herein, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

In some cases, an exogenous receptor, such as a gamma-delta TCR, can be expressed in a percentage of a population of cells. For example, from about 10%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5%, 99.9%, or 100% of cells in a population may express a gamma-delta TCR. A measurement of expression of an exogenous receptor, such as a gamma-delta TCR, may be taken by flow cytometric analysis.

In some cases, a gamma-delta TCR can be introduced non-virally. Polynucleotides encoding a gamma-delta TCR can be introduced as DNA or RNA. In some cases, a gamma-delta TCR can be introduced as DNA. In other cases, a gamma-delta TCR can be introduced as RNA. A gamma-delta TCR can be introduced as mRNA. mRNA can be introduced directly into a cell, for example by electroporation. CytoPulse technology can be utilized for electroporation. CytoPulse technology can use pulsed electric fields, to transiently permeabilize living cells for delivery of material, such as a gamma-delta TCR. The technology can allow for control of pulse duration, intensity as well as the interval between pulses. All these parameters can be modified in order to reach ideal conditions for high transfection efficiency with minimal mortality. In some cases, an electroporation pulse voltage may be varied to optimize transfection efficiency and/or cell viability. In some cases, the number of electroporation pulses may be varied to optimize transfection efficiency and/or cell viability. In some cases, the starting cell density for electroporation may be varied to optimize transfection efficiency and/or cell viability.

Accordingly, a cell, preferably a T cell, more preferably an engineered T cell is provided comprising or expressing a TCR, preferably an engineered TCR said TCR or engineered TCR comprising:
- a δT-cell receptor chain or part thereof comprising a CDR3 region, said δT-cell receptor chain or part thereof being represented by an amino acid sequence, said amino acid sequence comprising at least 60% sequence identity or similarity with any one of amino acid sequence SEQ ID NO: 3 and 6 to 237 and/or
- a γT-cell receptor chain or part thereof comprising a CDR3 region, said δT-cell receptor chain or part thereof being represented by an amino acid sequence, said amino acid sequence comprising at least 60% sequence identity or similarity with any one of amino acid sequence SEQ ID NO: 2 and 238 to 428. Preferably, the identity is of at least 65%, 70%, 75%, 80%, 85%, 90%, 95%, 97%, 98%, 99% or 100%.

Treatment

Effective adoptive cell transfer-based immunotherapies (ACT) can be useful to treat cancer (e.g., metastatic cancer) patients. In some cases, ACT can also be utilized to treat viral infections. Described herein can be a method of treating a disease (e.g., cancer or viral infection) in a recipient comprising transplanting to the recipient one or more engineered T cells that express an exogenous TCR, such as a gamma-delta TCR. In some cases, a viral infection can lead to cancer, such as an human papilloma virus (HPV), cytomegalovirus (CMV), Epstein-barr virus (EBV), hepatis B (HBV) and hepatitis C (HCV), Kaposi sarcoma-associated herpes virus (KSHV), Human T-lymphotrophic virus-1 (HTLV), Merkel cellpolyoma virus (MCV), human immunodeficiency virus (HIV), to name a few. Compositions disclosed herein can be utilized to treat a subjected infected with any one of the aforementioned viral infections.

Subject anti-HLA-A*24:02 engineered T cells can be formulated into a pharmaceutical medicament and be used to treat a human or mammal, in need thereof, diagnosed with a disease, e.g., cancer. Subject anti-HLA-A*24 engineered T cells can be formulated into a pharmaceutical medicament and be used to treat a human or mammal, in need thereof, diagnosed with a viral infection. These pharmaceutical medicaments can be co-administered to a human or mammal, together with one or more chemotherapeutic agent or chemotherapeutic compound. The term "pharmaceutical medicament" could be replaced by the term "pharmaceutical composition" or "medicament".

Populations of engineered T cells, such as αβ T cells engineered to express an HLA-A*24:02 specific γδ TCR, may be formulated for administration to a subject using techniques known to the skilled artisan. Formulations comprising populations of engineered cells may include pharmaceutically acceptable excipient(s). Excipients included in the formulations will have different purposes depending, for example, on the subpopulation of T cells used and the mode of administration. Examples of generally used excipients included, without limitation: saline, buffered saline, dextrose, water-for-injection, glycerol, ethanol, and combinations thereof, stabilizing agents, solubilizing agents and surfactants, buffers and preservatives, tonicity agents, bulking agents, and lubricating agents. The formulations comprising populations of engineered cells may be prepared and cultured in the absence of any non-human components, such as animal serum. A formulation may include one population of engineered cells, or more than one, such as two, three, four, five, six or more populations of engineered cells. For example, a formulation may include one population of engineered cells, or more than one, such as two, three, four, five, six or more populations of engineered cells. For example, more than one exogenous receptor may be expressed in a cell. In other cases, two populations of cells each expressing a different exogenous receptor are combined into a single formulation.

Formulations described herein may benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

In some cases, a binder may be used. Binders can impart cohesive qualities and include, e.g., alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crospovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, and the like.

A "carrier" or "carrier materials" include any commonly used excipients in pharmaceutics and should be selected on the basis of compatibility with compounds disclosed herein, such as, compounds of ibrutinib and An anticancer agent, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" can include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins1999).

"Dispersing agents," and/or "viscosity modulating agents" include materials that control the diffusion and homogeneity of a drug through liquid media or a granulation method or blend method. In some embodiments, these agents also facilitate the effectiveness of a coating or eroding matrix. Exemplary diffusion facilitators/dispersing agents include, e.g., hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), non-crystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizers such as cellulose or triethyl cellulose can also be used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

Formulations comprising population(s) of engineered cells may be administered to a subject using modes and techniques known to the skilled artisan. Exemplary modes include, but are not limited to, intravenous injection. Other modes include, without limitation, intratumoral, intradermal, subcutaneous (S.C., s.q., sub-Q, Hypo), intramuscular (i.m.), intraperitoneal (i.p.), intra-arterial, intramedullary, intracardiac, intra-articular (joint), intrasynovial (joint fluid area), intracranial, intraspinal, and intrathecal (spinal fluids). Any known device useful for parenteral injection of infusion of the formulations can be used to effect such administration.

In some cases, about $5\times10^{10}$ engineered T cells can be administered to a subject. In some embodiments, about $5\times10^{10}$ cells can represent a median amount of cells administered to a subject. In some embodiments, about $5\times10^{10}$ cells are necessary to affect a therapeutic response in a subject. In some embodiments, at least about $1\times10^6$ cells, at least about $2\times10^6$ cells, at least about $3\times10^6$ cells, at least about $4\times10^6$ cells, at least about $5\times10^6$ cells, at least about $6\times10^6$ cells, at least about $6\times10^6$ cells, at least about $8\times10^6$ cells, at least about $9\times10^6$ cells, at least about $1\times10^7$ cells, at least about $2\times10^7$ cells, at least about $3\times10^7$ cells, at least about $4\times10^7$ cells, at least about $5\times10^7$ cells, at least about $6\times10^8$ cells, at least about $6\times10^7$ cells, at least about $8\times10^8$ cells, at least about $9\times10^8$ cells, at least about $1\times10^8$ cells, at least about $2\times10^8$ cells, at least about $3\times10^8$ cells, at least about $4\times10^8$ cells, at least about $5\times10^8$ cells, at least about $6\times10^8$ cells, at least about $6\times10^8$ cells, at least about $8\times10^8$ cells, at least about $9\times10^8$ cells, at least about $1\times10^9$ cells, at least about $2\times10^9$ cells, at least about $3\times10^9$ cells, at least about $4\times10^9$ cells, at least about $5\times10^9$ cells, at least about $6\times10^9$ cells, at least about $6\times10^9$ cells, at least about $8\times10^9$ cells, at least about $9\times10^9$ cells, at least about $1\times10^{10}$ cells, at least about $2\times10^{10}$ cells, at least about $3\times10^{10}$ cells, at least about $4\times10^{10}$ cells, at least about $5\times10^{10}$ cells, at least about $6\times10^{10}$ cells, at least about $6\times10^{10}$ cells, at least about $8\times10^{10}$ cells, at least about $9\times10^{10}$ cells, at least about $1\times10^{11}$ cells, at least about $2\times10^{11}$ cells, at least about $3\times10^{11}$ cells, at least about $4\times10^{11}$ cells, at least about 5×10¹¹ cells, at least about 6×10¹¹ cells, at least about 6×10¹¹ cells, at least about 8×10¹¹ cells, at least about 9×10¹¹ cells, or at least about 1×10¹² cells. For example, about 5×10¹⁰ cells may be administered to a subject. In another example, starting with 3×10⁶ cells, the cells may be expanded to about 5×10¹⁰ cells and administered to a subject. In some cases, cells are expanded to sufficient numbers for therapy. For example, 5×10⁷ cells can undergo rapid expansion to generate sufficient numbers for therapeutic use. In some cases, sufficient numbers for therapeutic use can be 5×10¹⁰. Any number of cells can be infused for therapeutic use. For example, a subject may be infused with a number of cells between 1×10⁶ to 5×10¹² inclusive. In some embodiments, calculating the amount of engineered cells necessary to affect a therapeutic response comprises the viability of the cells and/or the efficiency with which a gamma-delta TCR has been integrated into the genome of a cell, such as an alpha-beta T cell. In some embodiments, in order to affect a therapeutic response in a subject, cells administered to a subject may be viable cells. In some embodiments, in order to effect a therapeutic response in a subject, at least about 95%, at least about 90%, at least about 85%, at least about 80%, at least about 75%, at least about 70%, at least about 65%, at least about 60%, at least about 55%, at least about 50%, at least about 45%, at least about 40%, at least about 35%, at least about 30%, at least about 25%, at least about 20%, at least about 15%, at least about 10% of the cells are viable cells. In some embodiments, in order to affect a therapeutic response in a subject, the cells administered to a subject may be cells that have had one or more transgenes successfully integrated into the genome of the cell. In some embodiments, in order to effect a therapeutic response in a subject, at least about 95%, at least about 90%, at least about 85%, at least about 80%, at least about 75%, at least about 70%, at least about 65%, at least about 60%, at least about 55%, at least about 50%, at least about 45%, at least about 40%, at least about 35%, at least about 30%, at least about 25%, at least about 20%, at least about 15%, at least about 10% of the cells have had one or more TCRs successfully integrated into a genome of a cell.

In some cases, a subject can be administered engineered T cells that express an exogenous gamma-delta TCR, wherein engineered T cells that express an exogenous gamma-delta TCR that can be administered may be about 1 to about 35 days old. For example, administered cells may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or up to about 40 days old. An age of an engineered T cell can be considered from a time of stimulation. An age of an engineered cell can be considered from a time of apheresis. An age of an engineered cell can be considered from a time of transduction. In some embodiments, engineered cells that can be administered to a subject are about 10 to about 14 or about 20 days old. In some cases, an "age" of an engineered cell can be determined by a length of a telomere. For example, a "young" cell can have a longer telomere length than an "exhausted" or "old" cell. Without being bound to a particular theory, it can be believed that immunoresponsive cells lose an estimated telomere length of about 0.8 kb per week in culture, and that young cell cultures can have telomeres that are about 1.4 kb longer than immunoresponsive cells that are about 44 days old. Without being bound to a particular theory, it is believed that longer telomere lengths can be associated with positive objective clinical responses in patients and persistence of the cells in vivo.

In some cases, cells are isolated from the subject organism, transfected with a nucleic acid (e.g., gene or cDNA), and re-infused back into a subject.

The methods disclosed herein can comprise transplanting. Transplantation can refer to adoptive transplantation of a cellular product including T cells expressing an exogenous γδ TCR. Transplanting can be autotransplanting, allotransplanting, xenotransplanting, or any other transplanting. For example, transplanting can be xenotransplanting. Transplanting can also be allotransplanting.

Cells (e.g., engineered cells or engineered primary T cells) before, after, and/or during transplantation can be functional. For example, transplanted cells can be functional for at least or at least about 1, 2, 3, 4, 5, 6, 7, 8, 9, 10, 11, 12, 13, 14, 15, 16, 17, 18, 19, 20, 21, 22, 23, 24, 25, 6, 27, 28, 29, 30, 40, 50, 60, 70, 80, 90, or 100 days after transplantation. Transplanted cells can be functional for at least or at least about 1, 2, 3, 4, 5, 6, 7, 8, 9, 10, 11, or 12 months after transplantation. Transplanted cells can be functional for at least or at least about 1, 2, 3, 4, 5, 6, 7, 8, 9, 10, 15, 20, 25, or 30 years after transplantation. In some cases, transplanted cells can be functional for up to the lifetime of a recipient.

Further, transplanted cells can function at 100% of their normal intended function. A normal intended function can be measured by comparing engineered cells to non-engineered control cells. For example, a level of a cytokine, such as IL-2, can be detected by ELISA assay and compared between an engineered population and a non-engineered population Transplanted cells can function 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or up to about 100% of their normal intended function. Transplanted cells can also function over 100% of their normal intended function. For example, transplanted cells can function 110, 120, 130, 140, 150, 160, 170, 180, 190, 200, 250, 300, 400, 500, 600, 700, 800, 900, 1000, or up to about 5000% of their normal intended function. Transplanted cells that function over a normal intended function may have supraphysiological levels of cytokine production in some cases. In other cases, transplanted cells that function over a normal cell may have increased persistence or expansion.

Transplanting can be by any type of transplanting. Sites can include, but not limited to, liver subcapsular space, splenic subcapsular space, renal subcapsular space, omentum, gastric or intestinal submucosa, vascular segment of small intestine, venous sac, testis, brain, spleen, or cornea. For example, transplanting can be subcapsular transplanting. Transplanting can also be intramuscular transplanting. Transplanting can be intraportal transplanting. In some cases, engineered cells are directly injected into a tumor.

In some cases, a subject may receive immunosuppressive therapy. Immunosuppressive therapy may accompany an allogenic infusion of a cellular product. In other cases, immunosuppression may be performed to improve performance of a cellular product, such as engineered T cells.

In some cases, host lymphopenia can facilitate expansion of engineered cells. On the one hand, lymphopenia can create "space" for oncoming adoptively transferred cells and, on the other, it can induce their homeostatic expansion. The latter effect can be likely mediated through chemotherapeutic ablation of endogenous regulatory T cells, which can normally secrete inhibitory cytokines (e.g. TGF-β and IL-10) that can limit effector cell expansion, such as engineered T cells. In some cases, a lymphocyte reduction treatment can improve expansion of engineered T cells in vivo by about 1 fold, 2 fold, 3 fold, 4 fold, 5 fold, 6 fold, 7 fold, 8 fold, 9 fold, 10 fold, 11 fold, 12 fold, 13 fold, 14 fold, 15 fold, 16 fold, 17 fold, 18 fold, 19 fold, or up to 20 fold over treatment with engineered cells without a lymphocyte reduction treatment.

Additionally, T-cell growth homeostatic cytokines, such as IL-7 and IL-15, which may ordinarily exist in limiting amounts, may become readily available due to less competition and increased production by lymphopoietic stromal cells. Thus, induction of lymphocyte reduction prior to infusion of an engineered cellular product may be performed to increase efficacy of engineered cells in treating a subject. In some cases, a lymphocyte reduction treatment may improve anti-tumor efficacy as measured by tumor reduction or control by about 10% to about 100% over treatment without a lymphocyte reduction treatment. For example a lymphocyte reduction treatment may improve anti-tumor efficacy from about 10%, 15%, 20%, 25%, 30%, 35%, 40%, 45%, 50%, 55%, 60%, 65%, 70%, 75%, 80%, 85%, 90%, 95%, or up to 100% over treatment without a lymphocyte reduction treatment.

Anti-HLA-A*24 cells can be administered in combination with other anti-tumor agents, including cytotoxic/antineoplastic agents and anti-angiogenic agents.

In some cases, interfering with an interaction between γδT cells and their cellular ligands can be used to diagnose and modulate inflammatory demyelinating disease (see Chien et al., 2005, US2005/0255105). A cellular ligand can include both non-classical and classical MHC molecules, non-protein ligands, and the like. Described herein can be a method of disrupting an interaction between a γδT cell and a target, such as an HLA-A*24-expressing cell to reduce a treatment associated toxicity. In some cases, a subject treated with a composition described herein may develop a toxicity. There are multiple modalities for abrogating and eliminating engineered cells that have been administred to a subject. For example, in some cases, an antibody may be introduced to bind to engineered cells. An antibody can inhibit binding of a polypeptide construct after an administration. For example, an antibody given to reduce treatment-related toxicity may be a neutralizing or blocking antibody. In other cases, nonspecific immune suppression or selective depletion of modified cells through "suicide" or "elimination" genes can be performed to abrogate treatment-related toxicity. For example, a polynucleic acid encoding an anti-HLA-A*24 may also encode for a suicide gene such as inducible Fas or caspase 9. A method of reducing toxicity can comprise administering an antibody or portion thereof. In other cases, an antibody may bind a γδ TCR on a cell and inhibit binding of that cell to a target. For example, a disease or infection can be treated by administration of an antibody or portion thereof that can bind a cellular receptor such as an FE11 or FE11-like receptor. In some cases, a binding of an antibody to a receptor can neutralize or block a receptor and may prevent toxicity associated with the binding of a receptor to it's ligand. In some cases, a toxicity in a subject can be at least one of cytokine release syndrome (CRS) B-Cell Aplasia, and Tumor Lysis Syndrome (TLS). CRS can be detected by a level of inflammatory symptoms resulting from cytokine elevations, such as IL-10, IL-6, and IFN-γ, associated with T cell engagement and proliferation. In most subjects, CRS symptoms are mild and flulike, with fevers and myalgias. However, some subjects can experience a severe inflammatory syndrome, including vascular leak, hypotension, pulmonary edema, and coagulopathy, resulting in multiorgan system failure, and death. In some cases, a subject with CRS may also have elevated IL-6. In some cases, an anti-IL-6 treatment may be administered.

Efficacy of adoptive immunotherapy, such as administration of engineered T cells expressing exogenous γδ TCRs can be evaluated using multiple modalities. Efficacy can refer to anti-tumor efficacy that can be the extent to which a tumor, such as an HLA-A*24-positive tumor, is controlled, reduced, or eliminated. Treatment efficacy can also refer to engineered cell expansion, persistence, tumor-targeting, and any combination thereof.

A subject that can be administered an adoptive cell therapy, such as anti-HLA-A*24 T cell therapy, can be evaluated during an infusion, immediately after an infusion, or up to years following an infusion. For example, a treated subject can return to a clinic for evaluation for a period of about 1 day to the length of the subject's life. A treated subject can be evaluated from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, or up to 90 years after an initial administration of an engineered cellular product. In some cases, an evaluation schedule can include daily monitoring, weekly monitoring, monthly monitoring, or yearly monitoring. In some cases, a subject can be seen more frequently as clinically indicated. An evaluation can include a physical exam, chemistry evaluation, complete blood count, thyroid panel, toxicity assessment, computerized tomography (CT) scan of a bodily area, apheresis, and any combination thereof.

In some cases, apheresis may be performed prior to and from about 1 to about 10 weeks following administration of an engineered cell infusion. At other time points, a subject's peripheral blood lymphocytes (PBL) can be obtained from whole blood by purification using centrifugation on a Ficoll gradiant. Aliquots of peripheral blood mononuclear cells (PBMCs) can be cryopreserved for immunological monitoring of cell function. In some cases, a variety of tests can include evaluation of specific lysis and cytokine release, metabolomic and bioenergetic studies (using Seahorse), intracellular FACS of cytokine production, ELISA-spot assays, and lymphocyte subset analysis may be used to evaluate the immunological correlates of an engineered cellular product. In general, differences of about 2 to about 3 fold in these assays may be indicative of true biologic differences. In some cases, differences of about 1, 1.5, 2, 2.5, 3, 3.5, 4, 4.5, up to about 5 fold of in vitro assay activity, may be indicative of treatment efficacy when engineered cells are compared to non-engineered cells.

In some cases, an adoptive immunotherapy utilized engineered T cells, may reduce tumor size by at least 30% as measured by computerized tomography (CT) scan or an MRI. An engineered cellular treatment may reduce tumor size by at least about 5%, 10%, 15%, 20%, 25%, 30%, 35%, 40%, 45%, 50%, 55%, 60%, 65%, 70%, 75%, 80%, 85%, 90%, 95%, or up to about 100%. An engineered cellular treatment may eliminate a tumor as measured by CT scan. In some cases, an anti-HLA-A*24:02 immunoresponsive cell treatment may stabilize a tumor size as measured by a less than 10% change in a baseline measurement of a diameter of a tumor lesion as measured by computerized tomography (CT) scan. For example, a tumor may not expand in size after administration of anti-HLA-A24:02 immunoresponsive cells. In some cases, stabilization may be considered a less than 10%, 9%, 8%, 7%, 6%, 5%, 4%, 3%, 2%, or 1% change in tumor size as compared to a pre-treatment measurement.

In some cases, anti-HLA-A*24:02 immunoresponsive cell efficacy can be considered in terms of subject survival time. For example, a subject that is treated with anti-HLA-A24 immunoresponsive cells, such as an anti-HLA-A24:02 T cells, can survive longer than an untreated subject or a subject treated with a different therapy.

Treatment response can be evaluated using the international criteria proposed by the revised Response Evaluation Criteria in Solid Tumors (RECIST) guideline (Version 1.1). Changes in the largest diameter (unidimensional measurement) of a tumor lesion and the shortest diameter in the case of malignant lymph nodes can be used in the RECIST criteria. For example, measurable lesions can be those defined as those that can be accurately measured in at least one dimension (longest diameter to be recorded) as >20 mm by chest x-ray, as >10 mm with CT scan, or >10 mm with calipers by clinical exam. To be considered pathologically enlarged and measurable, a lymph node can be >15 mm in short axis when assessed by CT scan. All other lesions (or sites of disease), including small lesions (longest diameter <10 mm or pathological lymph nodes with >10 to <15 mm short axis), can be considered non-measurable disease. Bone lesions, leptomeningeal disease, ascites, pleural/pericardial effusions, lymphangitis cutis/pulmonitis, inflammatory breast disease, can be considered as non-measurable.

All measurable lesions up to a maximum of 2 lesions per organ and 5 lesions in total, representative of all involved organs, can be identified as target lesions and recorded and measured at baseline. Target lesions can be selected on the basis of their size (lesions with the longest diameter), be representative of all involved organs, but in addition should be those that lend themselves to reproducible repeated measurements. It may be the case that, on occasion, the largest lesion does not lend itself to reproducible measurement in which circumstance the next largest lesion which can be measured reproducibly should be selected. A sum of the diameters (longest for non-nodal lesions, short axis for nodal lesions) for all target lesions can be calculated and reported as the baseline sum diameters. If lymph nodes are to be included in the sum, then only the short axis can be added into the sum. A baseline sum diameter will be used as reference to further characterize any objective tumor regression in the measurable dimension of the disease.

In some cases, a clinical lesion can be considered measurable when it can be superficial (e.g., skin nodules and palpable lymph nodes) and about 10 mm diameter as assessed using calipers (e.g., skin nodules). In cases, where a caliper cannot be used to measure a lesion, a CT scan or MRI can also be used. In some cases, a CT scan can yield slices of tissue from about 5 mm or less. A CT scan can have 5 mm, 4 mm, 3 mm, 2 mm, 1 mm or 0.5 mm scan thickness in some cases. If a CT scan has a slice thickness greater than 5 mm, a minimum size for a measurable lesion can be twice the slice thickness. In some cases, an MRI can also be performed to evaluate a subject. Ideally, the same type of scanner should be used and the image acquisition protocol should be followed as closely as possible to prior scans when determining treatment efficacy. Body scans should be performed with breath-hold scanning techniques, if possible. In some cases, a fluorodeoxyglucose (FDG)-positron emission tomography (PET) can be used to measure treatment efficacy.

Once a subject has been evaluated, target lesions can be grouped into stable disease (SD), progressive disease (PD), partial response (PR), and/or a complete response (CR). A SD can be considered neither sufficient shrinkage to qualify for PR nor sufficient increase to qualify for PD, taking as reference the smallest sum of diameters. A PD can be considered at least a 20% increase in the sum of the diameters of target lesions, taking as reference the smallest sum (this can include the baseline sum if that may be the smallest). In some cases, in addition to a relative increase of about 20%, a sum must also demonstrate an absolute increase of at least about 5 mm. A PR can be at least about 30% decrease in a sum of the diameters of target lesions, taking as reference the baseline sum of diameters. A CR can be elimination of target lesions.

Kits

Disclosed herein can be kits comprising compositions of polypeptide constructs described herein. Disclosed herein can also be kits for the treatment or prevention of a cancer, pathogen infection, immune disorder. A kit comprising a composition described herein can be used to treat a subject that has undergone a stem cell or solid organ transplantation. In one embodiment, a kit can include a therapeutic or prophylactic composition containing an effective amount of a composition of gamma-delta T cells in unit dosage form. In some embodiments, a kit comprises a sterile container which may contain a therapeutic composition of gamma-delta T cells; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments. In some cases, gamma-delta T cells, can be provided together with instructions for administering the cells to a subject having or at risk of developing a cancer, pathogen infection, immune disorder or allogeneic transplant. Instructions may generally include information about the use of the composition for the treatment or prevention of cancer, pathogen infection, immune disorder. In some cases, a kit can include from about $1\times10^4$ cells to about $1\times10^{12}$ cells. In some cases a kit can include at least about $1\times10^5$ cells, at least about $1\times10^6$ cells, at least about $1\times10^7$ cells, at least about $4\times10^8$ cells, at least about $5\times10^7$ cells, at least about $6\times10^7$ cells, at least about $6\times10^7$ cells, at least about $8\times10^7$ cells, at least about $9\times10^7$ cells, at least about $1\times10^8$ cells, at least about $2\times10^8$ cells, at least about $3\times10^8$ cells, at least about $4\times10^8$ cells, at least about $5\times10^8$ cells, at least about $6\times10^8$ cells, at least about $6\times10^8$ cells, at least about $8\times10^8$ cells, at least about $9\times10^8$ cells, at least about $1\times10^9$ cells, at least about $2\times10^9$ cells, at least about $3\times10^9$ cells, at least about $4\times10^9$ cells, at least about $5\times10^9$ cells, at least about $6\times10^9$ cells, at least about $6\times10^9$ cells, at least about $8\times10^9$ cells, at least about $9\times10^9$ cells, at least about $1\times10^{10}$ cells, at least about $2\times10^{10}$ cells, at least about $3\times10^{10}$ cells, at least about $4\times10^{10}$ cells, at least about $5\times10^{10}$ cells, at least about $6\times10^{10}$ cells, at least about $6\times10^{10}$ cells, at least about $8\times10^{10}$ cells, at least about $9\times10^{10}$ cells, at least about $1\times10^{11}$ cells, at least about $2\times10^{11}$ cells, at least about $3\times10^{11}$ cells, at least about $4\times10^{11}$ cells, at least about $5\times10^{11}$ cells, at least about $6\times10^{11}$ cells, at least about $6\times10^{11}$ cells, at least about $8\times10^{11}$ cells, at least about $9\times10^{11}$ cells, or at least about $1\times10^{12}$ cells. For example, about $5\times10^{10}$ cells may be included in a kit. In another example, a kit may include $3\times10^6$ cells; the cells may be expanded to about $5\times10^{10}$ cells and administered to a subject.

In some cases, a kit may include allogenic cells. In some cases, a kit may include cells that may comprise a genomic modification. In some cases, a kit may comprise "off-the-shelf" cells. In some cases, a kit may include cells that may be expanded for clinical use. In some cases, a kit may contain contents for a research purpose.

In some cases, the instructions include at least one of the following: description of the therapeutic agent; dosage schedule and administration for treatment or prevention of a neoplasia, pathogen infection, immune disorder or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container. In some cases, instructions provide procedures for administering gamma-delta T cells at least about 1, 2, 3, 4, 5, 6, 7, 8, 9,10, 11, 12, 13, 14, 15, 16, 17, 18, 19, 20, 21, 22, 23, 24, 25, 26, 27, 28, 29, 30, or up to 2 days, 3 days, 4 days, 5 days, 6 days, or 7 days after administering a chemotherapeutic agent. In some cases, instructions provide procedures for administering gamma-delta T cells at least 24 hours after administering a chemotherapeutic agent. Engineered T cells can be formulated for intravenous injection. Engineered T cells can be formulated for infusion. In some cases a kit may contain products at a pediatric dosage.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1

Generation and Validation of Retroviral Supernatant

Phoenix Eco cell line (American Type Culture Collection SD3444) with a vector encoding a γδTCR transgene to generate a pseudotyped transient supernatant, which is used to transduce PG13 cells (gibbon ape leukemia virus pseudotyping packaging cell line; American Type Culture Collection CRL-10686). The γδTCR transgene is detected by FACS analysis on the transduced PG13 cells with an idiotypic antibody. After single-cell cloning, the highest-titer clone for each vector is used to establish a master cell bank. Clones for clinical use are released only after safety testing and vector sequencing; to ensure none produce replication-competent retrovirus. Final viral supernatant is stored at −80° C. and tested before clinical release. Virus titers range from $6 \times 10^5$ to $1.6 \times 10^6$ virus particles per ml.

Example 2

Transduction of Cells to Express an Exogenous γδTCR

Isolation of Peripheral Blood Mononuclear Cells (PBMCs) from a LeukoPak

LeukoPaks collected from normal peripheral blood were used herein. Blood cells were diluted 3 to 1 with chilled 1× PBS. The diluted blood was added dropwise over 15 mLs of LYMPHOPREP (Stem Cell Technologies) in a 50 ml conical. Cells were spun at 400× G for 25 minutes with no brake. The buffy coat was slowly removed and placed into a sterile conical. The cells were washed with chilled 1× PBS and spun for 400× G for 10 minutes. The supernatant was removed, cells resuspended in media, counted and viably frozen in freezing media (45 mLs heat inactivated FBS and 5 mLs DMSO).

Isolation of CD3+ T Cells

PBMCs were thawed and plated for 1-2 hours in culturing media (RPMI-1640 (with no Phenol red), 20% FBS (heat inactivated), and 1× Gluta-MAX). Cells were collected and counted; the cell density was adjusted to $5 \times 10^7$ cells/mL and transferred to sterile 14 mL polystyrene round-bottom tube. Using the EasySep Human CD3 cell Isolation Kit (Stem Cell Technologies), 50 uL/mL of the Isolation Cocktail was added to the cells. The mixture was mixed by pipetting and incubated for 5 minutes at room temperature. After incubation, the RapidSpheres were vortexed for 30 seconds and added at 50 uL/mL to the sample; mixed by pipetting. Mixture was topped off to 5 mLs for samples less than 4 mLs or topped off to 10 mLs for samples more than 4 mLs. The sterile polystyrene tube was added to the "Big Easy" magnet; incubated at room temperature for 3 minutes. The magnet and tube, in one continuous motion, were inverted, pouring off the enriched cell suspension into a new sterile tube.

Activation and Stimulation of CD3+ T Cells

Isolated CD3+ T cells were counted and plated out at a density of $2 \times 10^6$ cells/mL in a 24 well plate. Dynabeads Human T-Activator CD3/CD28 beads (Gibco, Life Technologies) were added 3:1 (beads: cells) to the cells after being washed with 1× PBS with 0.2% BSA using a dynamagnet. IL-2 (Peprotech) was added at a concentration of 300 IU/mL. Cells were incubated for 48 hours and then the beads were removed using a dynamagnet. Cells were cultured for an additional 6-12 hours before electroporation or nucleofection.

Retroviral Transduction of CD3+ T Cells

Stimulated T cells are transduced by day 3 in 24-well plates precoated with a recombinant fibronectin fragment (FN CH-296, Retronectin Takara). After retroviral transduction, T cells are expanded ex vivo in the presence of rhIL-2 (50-100 U/ml) added twice weekly, without any additional stimulation with OKT3 antibody.

TABLE 2

Sequences described herein

| SEQ ID NO | Construct | Sequence |
|---|---|---|
| 2 | γ-TCR CDR | CATWDRPEIYYKKL F |
| 3 | δ-TCR CDR | CALGDSYGGGPLYTDKLIF |

TABLE 2-continued

Sequences described herein

| SEQ ID NO | Construct | Sequence |
|---|---|---|
| 4 | FE11 γ-TCR including signal peptide. The signal peptide is represented by amino acids 1-18. The functional protein as expressed on the cell surface comprises amino acids 19-309 | M G W A L L V L L A F L S P A S Q K S S N<br>L E G G T K S V T R P T R S S A E I T C D L<br>T V I N A F Y I H W Y L H Q E G K A P Q R<br>L L Y Y D V S N S K D V L E S G L S P G K Y<br>Y T H T P R R W S W I L I L R N L T E N D S<br>G V Y Y C A T W D R P E I Y Y K K L F G S<br>G T T L V V T D K Q L D A D V S P K P T I<br>F L P S I A E T K L Q K A G T Y L C L L E K<br>F F P D V I K I H W E E K K S N T I L G S Q<br>E G N T M K T N D T Y M K F S W L T V P E<br>K S L D K E H R C I V R H E N N K N G V D<br>Q E I I P P P I K T D V I T M D P K D N C S K<br>D A N D T L L L Q L T N T S A Y Y M Y L L<br>L L L K S V V Y F A I I T C C L L R R T A F<br>C C N G E K S |
| 5 | FE11 δ-TCR including signal peptide. The signal peptide is represented by amino acids 1-20. The functional protein as expressed on the cell surface comprises amino acids 21-293 | M V F S S L L C V F V A F S Y S G S S V A<br>Q K V T Q A Q S S V S M P V R K A V T L N<br>C L Y E T S W W S Y Y I F W Y K Q L P S K<br>E M F L I R Q G S D E Q N A K S G R Y S V<br>N F K K A A K S V A L T I S A L Q L E D S A<br>K Y F C A L G D S Y G G G P L Y T D K L I<br>F G K G T R V T V E P R S Q P H T K P S V F<br>V M K N G T N V A C L V K E F Y P K D I R<br>I N L V S S K K I T E F D P A I V I S P S G K<br>Y N A V K L G K Y E D S N S V T C S V Q H<br>N D K T V H S T D F E V K T D S T D H V K<br>P K E T E N T K Q P S K S C H K P K A I V H<br>T E K V N M M S L T V L G L R M L F A K T<br>V A V N F L L T A K L F F L |

Example 3

Immunophenotyping

γδ-modified T lymphocytes are stained with monoclonal antibodies to CD3, CD4, CD8, CD62L, CD45RA, CD45RO, CCR7, and CD28 (Becton Dickinson). We analyzed the cells using a FACScan Flow Cytometer (Becton Dickinson) equipped with a filter set for 4 fluorescence signals.

Example 4

Cytotoxicity Assay

Target tumor cells are harvested, labeled with 50 μCi $Na_2^{51}CrO_4$ for 60 min at 37° C., washed three times, and added to various numbers of effector anti-FE11 γδ-modified T lymphocytes in a final volume of 150 μl IMDM supplemented with 10% FBS in 96-well U-bottomed microtiter plates. Tumor tumor cells expressing FE11-K562 (positive control) and K562 (negative control) are used. After 4 or 18 h of incubation of target and effector cells at 37° C. and 5% $CO_2$, 25 μl supernatant is harvested and measured in a luminescence counter (Topcount-NXT; Packard Instrument Co.). The mean percentage of specific lysis of triplicate wells was calculated as follows: specific lysis=[(experimental release−spontaneous release)/(maximal release−spontaneous release)]×100.

Example 5

Proliferation Assay

Proliferation of anti-FE11 T cells after exposure to target cells (FE11-K562, FE11+) or control cells (K562, FE11−) is determined by carboxyfluorescein succinimidyl ester dilution assays.

One week post-transduction, control T lymphocytes and anti-FE11αβ T cells are labeled with 1.5 μmol/L carboxyfluorescein diacetate succinimidyl ester (CFSE; Invitrogen) and plated with irradiated tumor targets (FE11-K562 and K562) at an effector-to-target (E:T) ratio of 5:1. CFSE dilution is measured on $CD4^+$ and $CD8^+$ T cells by flow cytometry on day 4 of co-culture.

Example 6

Generation of T Cell Clone Comprising a Polypeptide Construct that Binds HLA Conformation Described Herein Bulk γδT cells were isolated from healthy donor PBMCs using the TCRγ/δ+ T Cell Isolation MACS Kit (Miltenyi Biotec), and expanded using a previously described rapid expansion protocol (Riddell S R, Greenberg P D. The use of anti-CD3 and anti-CD28 monoclonal antibodies to clone and expand human antigen-specific T cells. J Immunol Methods. 1990; 128(2):189-201). Briefly, γδT cells were stimulated for two weeks with 1 μg/ml PHA-L (Sigma-Aldrich), 50 U/ml IL-2 (Novartis Pharma), 5 ng/ml IL-15 (R&D Systems), and irradiated allogeneic PBMCs, Daudi and EBV-LCLs. Fresh IL-2 was added twice per week. The γδT cell clone was generated from bulk γδT cells by limiting dilution, and expanded biweekly using the rapid expansion protocol.

Cloning of γδTCR Described Herein

Total RNA of desired γδT cell clone was isolated using the Nucleospin RNA-II kit (Macherey-Nagel) and reverse-transcribed using SuperScript-II reverse transcriptase (Invitrogen). TCR γ and δ chains were amplified by PCR using Vδ1 (5'-GATCAAGTGTGGCCCAGAAG-3') (SEQ ID NO. 429) and Vγ2-5 (5'-CTGCCAGTCAGAAATCTTCC-3') (SEQ ID NO. 430) sense primers, and Cδ (5'-TTCACCA- GACAAGCGACA-3') (SEQ ID NO. 431) and Cγ (5'-GGG-GAAACATCTGCATCA-3') (SEQ ID NO. 432) antisense primers. PCR products were sequenced, and codon-optimized sequences of the desired γδTCR were subsequently synthesized by Geneart® (Life Technologies) and subcloned into the retroviral pBullet vector.

Retroviral Transduction of TCRs and HLA

The Vγ5Vδ1-TCR clone described herein and an HLA-A*0201-restricted WT1 126-134-specific αβTCR were transduced into αβT cells. In brief Phoenix-Ampho packaging cells were transfected with gag-pol (pHIT60), env (pCOLT-GALV) and pBullet retroviral constructs containing TCRγ/β-chain-IRES-neomycine or TCRδ/α-chain-IRES-puromycin, using Fugene-HD (Promega). PBMCs preactivated with α-CD3 (30 ng/ml) (clone OKT3, Janssen-Cilag) and IL-2 (50 U/ml) were transduced twice with viral supernatant within 48 hours in the presence of 50 U/ml IL-2 and 4 µg/ml polybrene (Sigma-Aldrich). Transduced T cells were expanded by stimulation with α-CD3/CD28 Dynabeads ($0.5 \times 10^6$ beads/$10^6$ cells) (Invitrogen) and IL-2 (50 U/ml) and selected with 800 µg/ml geneticin (Gibco) and 5 µg/ml puromycin (Sigma-Aldrich) for one week. CD4+ TCR-transduced T cells were isolated by MACS-sorting using CD4-microbeads (Miltenyi Biotec). Following transduction, transduced T cells were stimulated biweekly with 1 µg/ml PHA-L (Sigma-Aldrich), 50 U/ml IL-2 (Novartis Pharma), 5 ng/ml IL-15 (R&D Systems), and irradiated allogeneic PBMCs, Daudi and LCL-TM cells. Fresh IL-2 was added twice per week. Where indicated, CD4+, CD8+, CD4+CD8αα+ and CD4+CD8αβ+ TCR-transduced T-cells were sorted using a FACSAria II (BD) flow cytometry to >99% purity. Following selection, TCR-transduced T-cells were stimulated biweekly using the rapid expansion protocol. Expression levels of CD8α mutants were measured by flow cytometry using two different anti-CD8α antibody clones (clones RPA-T8 and G42-8). Transgenic TCR expression and purity of CD4+ populations were routinely assessed by flow cytometry.

Flow Cytometry

Antibodies used for flow cytometry included: γδTCR-PE (clone IMMU510, Beckman Coulter), CD4-PE-Cy7 (clone RPA-T4, BD), CD8α-APC (clone RPA-T8, BD), CD8α-PerCP-Cy5.5 (clone RPA-T8, Biolegend), CD8α-FITC (clone G42-8, BD), and CD8αβ-PE (clone 2ST8.5H7, BD). NY-ESO1 (HLA-A*02:0 SLLMWITQV) (SEQ ID NO: 433) R-PE labelled Pro5 MHC Pentamer (Proimmune) and CMV (HLA-A*24:02 QYDPVAALF) (SEQ ID NO: 434) R-PE labelled ProS MHC Pentamer (Proimmune) were used according to the manufacturer's instructions. Samples were measured with FACSCanto-II and LSRFortessa cytometers (BD) and analyzed with FACSDiva software (BD).

Example 7

Generation of HLA Monoclonal Antibodies

Monoclonal antibodies (mAbs) were generated by immunization of C57BL/6 mice with SW480 and LCL-TM after which standard fusion of spleen cells was performed to generate hybridomas. Monoclonality was achieved by cloning by limiting dilution twice after which isotype determination was determined by flow cytometry using α-mIgG1 APC (Pierce), α-mIgG2b RPE (Jackson), α-mIgG2c dylight 405 (Jackson), and α-mIgG3 PerCP (Jackson). For mAb production, hybridoma's were cultured from about $5 \times 10^5$ to about $8 \times 10^5$ cells/mL for 1 week in serum-free hybridoma medium. mAbs were purified using protein G HP SpinTrap columns (GE healthcare) following the manufacturer's instructions.

Protein Separation and Digestion

Samples were run on a 4-12% Bis-Tris 1D SDS-PAGE gel (BioRad) for 2.5 h and stained with colloidal coomassie dye G-250 (Gel Code Blue Stain Reagent, Thermo Scientific). The lane was cut as three bands, which were treated with 6.5 mM dithiothreitol (DTT) for 1 h at 60° C. for reduction and 54 mM iodoacetamide for 30 min for alkylation. The proteins were digested overnight with trypsin (Promega) at 37° C. The peptides were extracted with 100% acetonitrile and dried in a vacuum concentrator.

Mass Spectrometry: RP-nanoLC-MS/MS

Samples were reconstituted in 10% formic acid and analyzed by nano-LC-MS/MS on a Orbitrap Q-Exactive Plus (ThermoFisher Scientific, Bremen) coupled to an Agilent 1290 Infinity System (Agilent Technologies) operating in reverse phase (C18) equipped with a Reprosil pur C18 trap column (100 µm×2 cm, 3 µm) and a Poroshell 120 EC C18 (Agilent Technologies) analytical column (75 µm×50 cm, 2.7 µm). After trapping with 100% solvent A (0.1% FA in H2O) for 10 min, peptides were eluted with an step gradient consisting of 35 min from 13% to 40% and, 3 min from 40% to 100% solvent B (0.1% FA, 80% ACN). The Q-Exactive Plus was operated in data-dependent acquisition mode using the following settings: full-scan automatic gain control (AGC) target 3e6 at 35 000 resolution; scan range 375-1600 m/z; Orbitrap full-scan maximum injection time 10 ms; MS2 scan AGC target 5e4 at 17 500 resolution; maximum injection 120 ms; normalized collision energy 25; dynamic exclusion time 10 s; isolation window 1.5 m/z; 10 MS2 scans per full scan.

Mass Spectrometry Data Analysis

Raw files were processed using Proteome Discoverer 1.4 (version 1.4.1.14, Thermo Scientific, Bremen, Germany). Raw files of the 3 bands per sample were combined in one search against a Uniprot database (*Homo Sapiens*, April 2015). The following parameters were used: carbamidomethylation of cysteines was set as a fixed modification and oxidation of methionine was set as a variable modification. Trypsin was specified as enzyme and up to two miss cleavages were allowed. A false discovery rate of 0.01 was used. Datasets processed by Proteome Discoverer were submitted to the Contaminant Repository for Affinity Purification (CRAPome) and proteins identified were sorted by Significance Analysis of INTeractome (SAINT) score, and the fold change scores FC-A or FC-B. The controls used were taken from the control immunoprecipitations performed with unspecific antibodies in each cell line. Proteins with SAINT probability greater than 0.9 were considered high-scoring interactions. Final selection of best interactors was based on known response of cell lines to the specific antibodies (Mellacheruvu D, Wright Z, Couzens A L, Lambert J P, St-Denis N A, Li T, et al. The CRAPome: a contaminant repository for affinity purification-mass spectrometry data. Nat Methods. 2013; 10(8):730-6.).

Example 8

Clinical Expansion of Anti-HLA-A*24:02 Engineered αβ T Cells

In order to generate a large number of transduced T cells, the cells are induced to proliferate using a rapid expansion protocol (REP). Prior to being used in REPs, T cells are started in culture with anti-CD3, anti-CD28 and IL-2 and transduced on the second day after the initiation of culture as detailed above. The cells are cultured in a 75 cm² flask at 37° C. and 5% $CO_2$. The cells are counted and suspended at a concentration of $0.5 \times 10^6$ cells/mL in fresh T cell medium with 300 IU/mL of IL-2 every two days for the remainder of the time they will be kept in culture.

Example 9

ELISPOT Assays

Introduction of γδTCR Described Herein in αβ T Cells Re-Established Tumor Cell Recognition To analyze the antigen-specific response specifically triggered by tumor cells, γδTCR engineered T cells or mock transduced T cells were initially tested for specific IFN-γ release against DAUDI, SW480, EBV-LCL, or PBMC cells by ELISPOT assay. Briefly, 15,000 FE11 TCR-transduced or mock-transduced T cells and 50,000 target cells (ratio 0.3:1) were cocultured for 18 hours in nitrocellulose-bottomed 96-well plates (Millipore) precoated with α-IFNγ antibody (clone 1-D1K) (Mabtech). Plates were washed and incubated with a second biotinylated anti-IFNγ antibody (clone 7-B6-1) (Mabtech) followed by streptavidin-HRP (Mabtech). IFNγ spots were visualized with TMB substrate (Sanquin) and the number of spots was quantified using ELISPOT Analysis Software (Aelvis). After incubation with tumor cells, γδTCR engineered T cells secreted large amount of IFN-γ cytokine in an antigen-specific manner, FIG. 1A and FIG. 1B. Results suggest that γδTCR engineered T cells are capable of killing tumor cells in a specific manner.

For testing stimulation of WT1 αβTCR-transduced T cells, the HLA-A2+ cell lines T2, SW480 and K562 HLA-A*02:01 were pulsed with 10 µM WT1 126-134 (RMFPNAPYL) (SEQ ID NO: 435) peptide.

HLA-A*24:02 Dependent Tumor Cell Recognition

Figure 2:
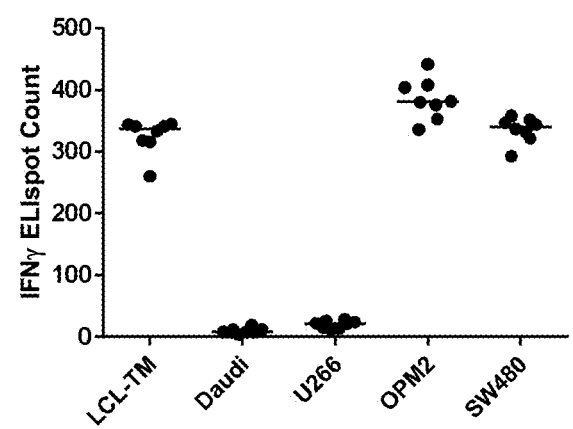
FIG. 2 shows results of an ELISPOT assay where γδ-TCR cells described herein were cocultured with LCL-TM, DAUD1, U266, OPM2, and SW480 tumor cell lines. IFNγ ELIspot count is shown.

To analyze the HLA-A*24:02-specific response specifically triggered by tumor cells, γδTCR engineered T cells were tested for specific IFN-y release against LCL-TM, DAUDI, U266 OPM2 or SW480 by ELISPOT assay. After incubation with tumor cells, γδTCR engineered T cells secreted large amount of IFN-γ cytokine in an HLA-A*24:02-specific manner, FIG. 2 and Table 3. Results suggest that γδTCR engineered T cells are capable of killing HLA-A*24:02 positive tumor cells.

TABLE 3

HLA-A expression on various cell lines

| Cell line | IFNγ | Killing | HLA-A | HLA-A |
|---|---|---|---|---|
| LCL-18 | No | ND | A*0201 | A*24:03 |
| LCL-22 | Yes | ND | A*2402 | A*0101 |
| LCL-48 | No | ND | A*2902 | A*0201 |
| LCL-66 | No | ND | A*0201 | A*0201 |
| LCL-68 | No | ND | A*0201 | A*0201 |
| LCL-69 | Yes | ND | A*2402 | A*0201 |
| LCL-71 | No | ND | A*2501 | A*1101 |
| LCL-82 | Yes | ND | A*0301 | A*2402 |
| LCL-86 | No | ND | A*0301 | A*0301 |
| LCL-87 | Yes | ND | A*0101 | A*2402 |
| LCL-89 | Yes | ND | A*2402 | A*2402 |
| LCL-93 | Yes | Yes | A*2402 | A*2501 |
| LCL-TM | Yes | Yes | A*24:02:01:01 | A*03:01:01:01 |
| SW480 | Yes | Yes | A*02:01:01:01 | A*24:02:01:01 |
| Daudi | No | No | — | — |
| K562 | No | ND | — | — |
| Hep-2 | No | No | A*68:02:01:01 | |
| HepG2 | Yes | Yes | A*24 | A*02 |
| MZ1851RC | No | No | | |
| HeLa | No | ND | | |
| Cal27 | No | No | | |
| T2 | ND | No | | |
| HEK293FT | ND | No | A*03:01 | A*02:01 |
| COS-7 Trans. | Yes | ND | A*24:02 | |
| COS-7 Trans. | No | ND | A*02 | |
| K562 Trans. | Yes | ND | A*24:02 | |
| K562 Trans. | No | ND | A*02 | |
| OPM2 | Yes | ND | A*24:02:01:01 | A*24:02:01:01 |
| U266 | No | ND | A*02+ | A*24− |

Example 10

ELISA Assay

Blocking Actin Polymerization Blocks COS7 HLA-A*24:02 Target Cell Recognition

Figure 3:
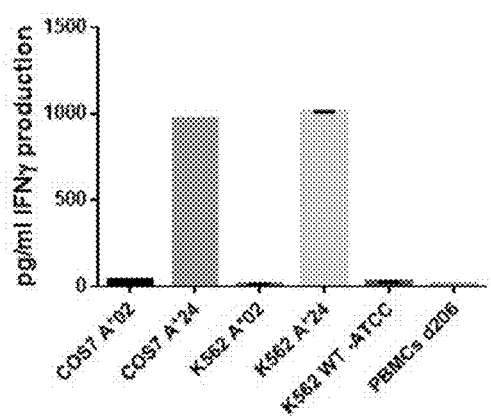
FIG. 3A shows results of an IFNγ ELISA assay where γδ-TCR described herein are co-cultured with COS7-A*02, COS7-A*24, K562-A*02, K562-A*24, K562-WT ATCC, and PBMCs d206.
FIG. 3B shows results of an IFNγ ELISA assay where Cyto D pre-treated γδ-TCR described herein are co-cultured with COS7-A*02, COS7-A*24, K562-A*02, K562-A*24, K562-WT ATCC, and PBMCs d206.
Figure 3:
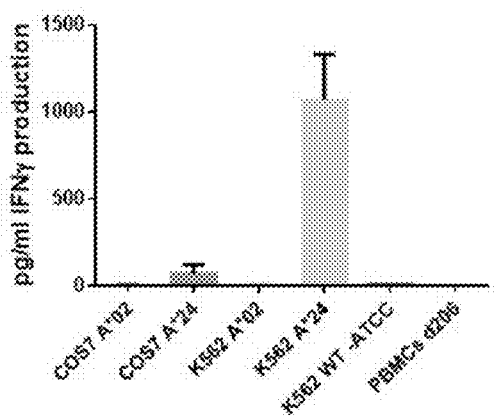

To evaluate whether recognition of target tumor cells is mediated via clustering of HLA-A*24:02 on the tumor cell surface a blocking actin polymerization assay was performed. Tumor cells COS7-A*02, COS7-A*24, K562-A*02, K562-A*24, K562-WT and PBMC were treated with cytochalasin D (CytoD), a widely used inhibitor of actin dynamics, prior to incubation with γδTCR-FE11. Results show that blocking actin polymerization blocks COS7 recognition by γδTCR-FE11, FIG. 3A and FIG. 3B.

Paraformaldehyde Fixing of Target Cells Inhibits Recognition

Figure 4:
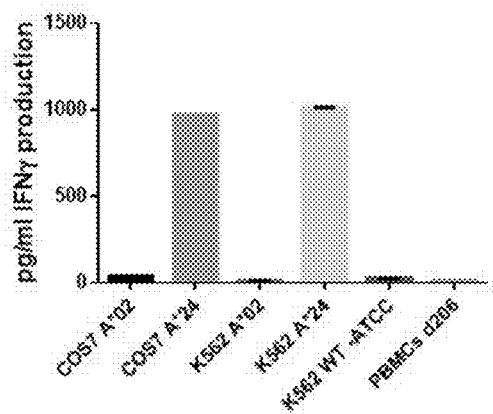
FIG. 4A shows results of an IFNγ ELISA assay where γδ-TCR described herein are co-cultured with COS7-A*02, COS7-A*24, K562-A*02, K562-A*24, K562-WT ATCC, and PBMCs d206.
FIG. 4B shows results of an IFNγ ELISA assay where γδ-TCR described herein are co-cultured with fixed targets: COS7-A*02, COS7-A*24, K562-A*02, K562-A*24, K562-WT ATCC, and PBMCs d206.
Figure 4:
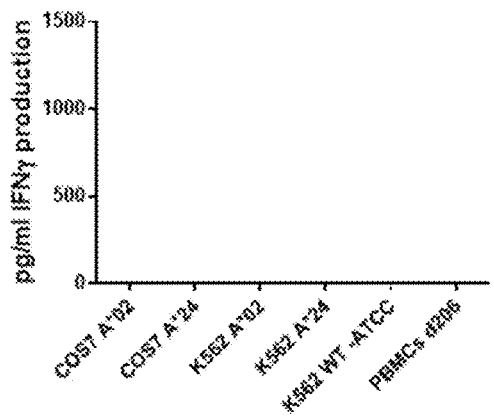
Figure 6:
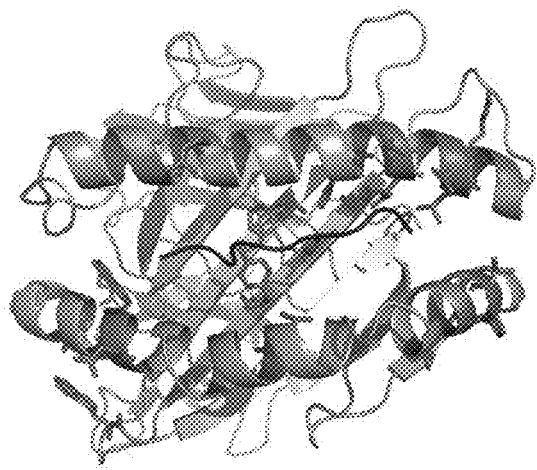
FIG. 6A shows a structure of HLA-A*02. HLA-A*02 is shown in gray. β2M is shown in yellow, peptide is shown in black, and polymorphisms are shown in red.
FIG. 6B shows a structure of HLA-A*02. HLA-A*02 is shown in gray. β2M is shown in yellow, peptide is shown in black, and polymorphisms are shown in red.
Figure 6:
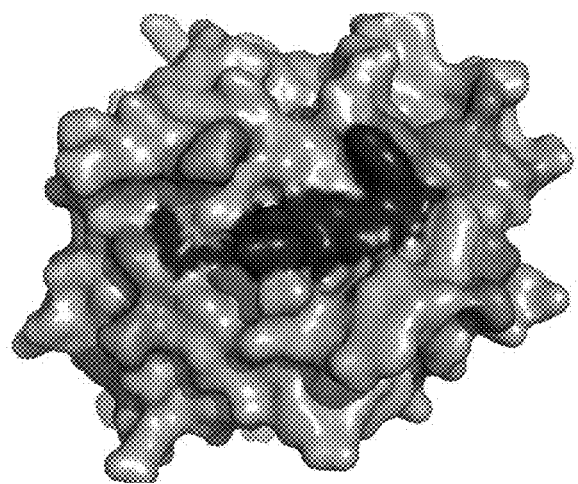
Figure 7A:
FIG. 7A shows a structure of HLA-A*02.
Figure 7:
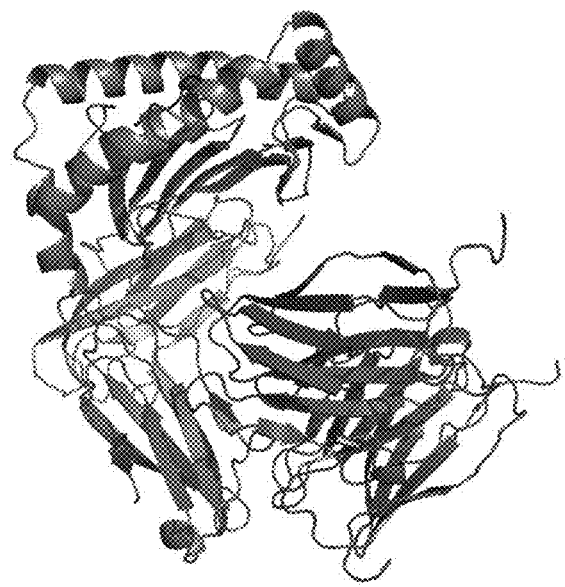
FIG. 7B shows a structure of HLA-A*02.

To evaluate whether recognition of target tumor cells is mediated via clustering of HLA-A*24:02 on the tumor cell surface a paraformaldehyde fixing of tumor cells was performed prior to a cocultured assay. Tumor cells COS7-A*02, COS7-A*24, K562-A*02, K562-A*24, K562-WT and PBMC were treated with paraformaldehyde prior to incubation with γδTCR-FE11. Results show that fixing tumor cells prior to coculture with γδTCR-FE11 inhibits recognition by γδTCR-FE11, FIG. 4A and FIG. 4B.

Example 11

Clinical Administration and Evaluation of Engineered Cells Expressing Polypeptide Constructs Described Herein Patients with evaluable cancer undergo apheresis to isolate peripheral blood mononuclear cells. Lymphocytes are isolated, virally transduced with a polypeptide construct comprising a TCR described herein, expanded, and aliquots taken for immunologic testing. On days −7 and −6 before T cell administration, patients undergo a preparative regime of cyclophosphamide at 60 mg/kg/day×2 days IV over 1 hr. On days −7 and −3 before cellular administration, patients undergo a preparative regime of fludarabine 25 mg/m²/day IVPB daily over 30 minutes for 5 days. During the preparative regimen, patients undergo daily complete blood count (CBC) testing.

In the first part of a phase I study a dose escalation is initiated utilizing one patient per group starting at $10^9$ engineered T cells per patient. Individual patients are treated at half log increments. Thus the following doses will be utilized: $10^9$, $3 \times 10^9$ cells, $10^{10}$ cells, $3 \times 10^{10}$ cells, and up to 1×10¹¹ cells. Autologous T cells expressing a polypeptide construct described herein are administered intravenously over 20 to 30 minutes via non-filtered tubing.

All patients return to the clinic for evaluation 6 weeks following administration of the cellular product.

Example 12

Quantitative PCR

Q-PCR is used to quantify retroviral integrants for γδ-modified T lymphocytes by detecting the γδTCR transgene in PBMCs collected before and at different time points after T cell infusion. After DNA extraction with the QIAamp DNA Blood Mini Kit (Qiagen), DNA is amplified in triplicate with primers and TaqMan probes (Applied Biosystems) specific for the γδTCR transgene, using the ABI PRISM 7900HT Sequence Detection System (Applied Biosystems). The baseline range is set at cycles 6 to 15, with the threshold at 10 SDs above the baseline fluorescence. To generate DNA standards, serial dilution of DNA plasmids encoding γδTCR transgene cassettes are used.

Example 13

Tumor Clustering Detection

Freshly harvested tumor cells are labeled before or after gentle fixation with 0.5% paraformaldehyde for 1 hr at 4° C. After washing the cell suspension twice in phosphate-buffered saline (PBS, pH 7.4), the cell pellet is resuspended in 100 μl of PBS and incubated with 100 μg/ml of FITC- or TRITC-conjugated mAb for 40 min at 4° C. Using FITC-conjugated antibodies as first antibodies before immunogold labeling is useful for checking antibody binding. Labeled cells are washed twice in cold PBS and fixed at this point of preparation. For scanning force microscopic (SFM) and transmission electron microscopic (TEM) measurements the cell suspension is further incubated with 10 μl of Aurogamig G-30 (Amersham; diameter, 30±3 nm) or 10 μl of gold-labeled goat-anti-mouse-Ig (Sigma Aldrich; diameter, 15 μm±2 nm) carrying polyclonal goat anti-mouse antibodies directed against IgG Fc and the whole molecule, respectively. In some experiments Aurogamig G-15 (Amersham; diameter, 15±1 nm) against IgG Fc can also be used. After 40 min incubation on ice, the cells are washed and stored at 4° C. The excess valences of gold beads are neutralized by adding mouse IgG in large quantity before applying the second mAb and the second gold beads. The possibility of artefactual clustering of receptors by the labeling procedure with bivalent antibodies is excluded by testing Fab fragments of every applied antibody. Furthermore, fixing the cells in 0.5% paraformaldehyde before or after the labeling does not influence the results.

Example 14

Flow Cytometric Energy Transfer Measurements

To study dimerization of HLA, cells were labelled with Alexa594-conjugated α-HLA-A (donor) and Alexa647-conjugated α-HLA-A (acceptor), respectively. The donor fluorescence was measured using a FACS LSRFortessa flow cytometer (BD) where donor fluorescence of the double-labeled healthy samples was compared with that of the double-labeled malignant samples. FRET efficiency was calculated from the fractional decrease of the donor fluorescence in the presence of the acceptor. FRET efficiency was calculated with equations according to Sebestyen and colleagues (Sebestyen Z, Nagy P, Horvath G, Vamosi G, Debets R, Gratama J W, et al. Long wavelength fluorophores and cell-by-cell correction for autofluorescence significantly improves the accuracy of flow cytometric energy transfer measurements on a dual-laser benchtop flow cytometer. Cytometry. 2002; 48(3):124-35.) where donor fluorescence was excited at 488 nm and detected at 576±26 nm, acceptor fluorescence was excited at 635 nm and detected at 780±60 nm, whereas FRET intensity was excited at 488 nm and detected at 780±60 nm. Correction factors for the spectral overlap between the different fluorescence channels were obtained from data measured on unlabeled and single-labeled cells.

Example 15

CRISPR Genome Editing

HEK293FT cells were transfected using Fugene-HD (Promega) with lentiviral constructs containing β2m (Sigma-Aldrich) together with lentiviral helper constructs VSVG and pspax2. LCL-TM cells were transduced with viral supernatants, knockdown was confirmed by flow cytometry. The β2m gene-specific regions of the gRNA sequence (GAGTAGCGCGAGCACAGCTA) (SEQ ID NO: 436) was designed by the CRISPR design tool from the Zhang lab (http://crispr.mit.edu/). As control gRNA, the eGFP gene (GGAGCGCACCATCTTCTTCA) (SEQ ID NO: 437) was targeted.

Example 16

Role of γδTCR-Like Antibodies and Classical HLA Molecules

Figure 8A:
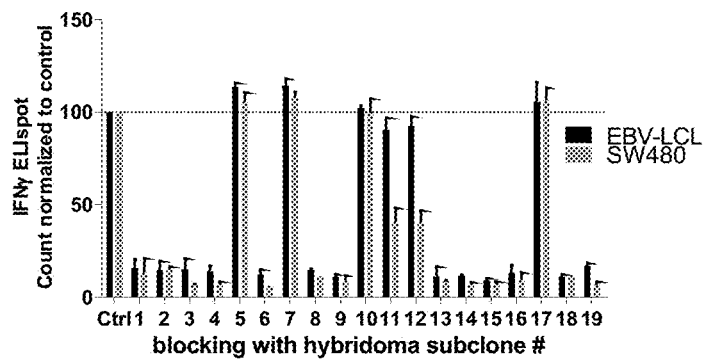
FIG. 8A shows the effect of blocking with FE-11 like hybridoma supernatant on the recognition of SW480 and LCL-TM by γδTCR described herein transduced T cells.
Figure 8:
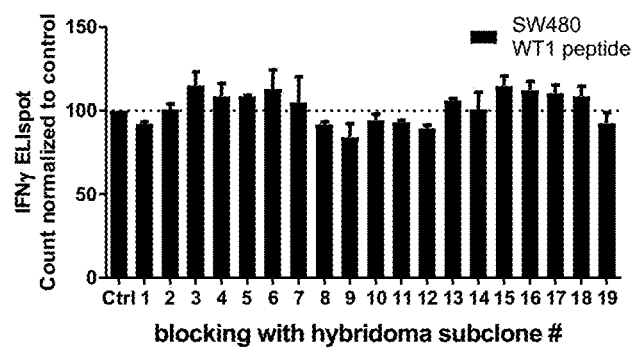
FIG. 8B shows the effect of blocking with FE-11 like hybridoma supernatant on the recognition of SW480 loaded with WT1 peptide by αβTCR WT1 transduced T cells.
FIG. 8C shows LABScreen Single Antigen HLA class I beads were incubated with antibodies that bind HLA, wherein said antibodies were purified from hybridomas, and bound HLA fully or partially and secondary α-mIgG-PE and measured using Luminex.
Figure 8:
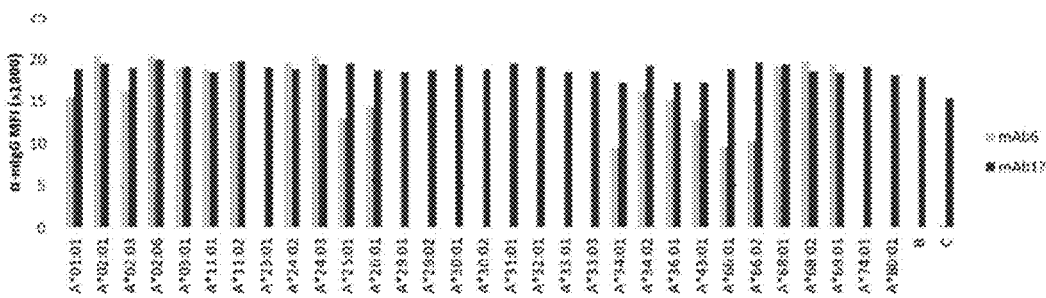
Figure 9:
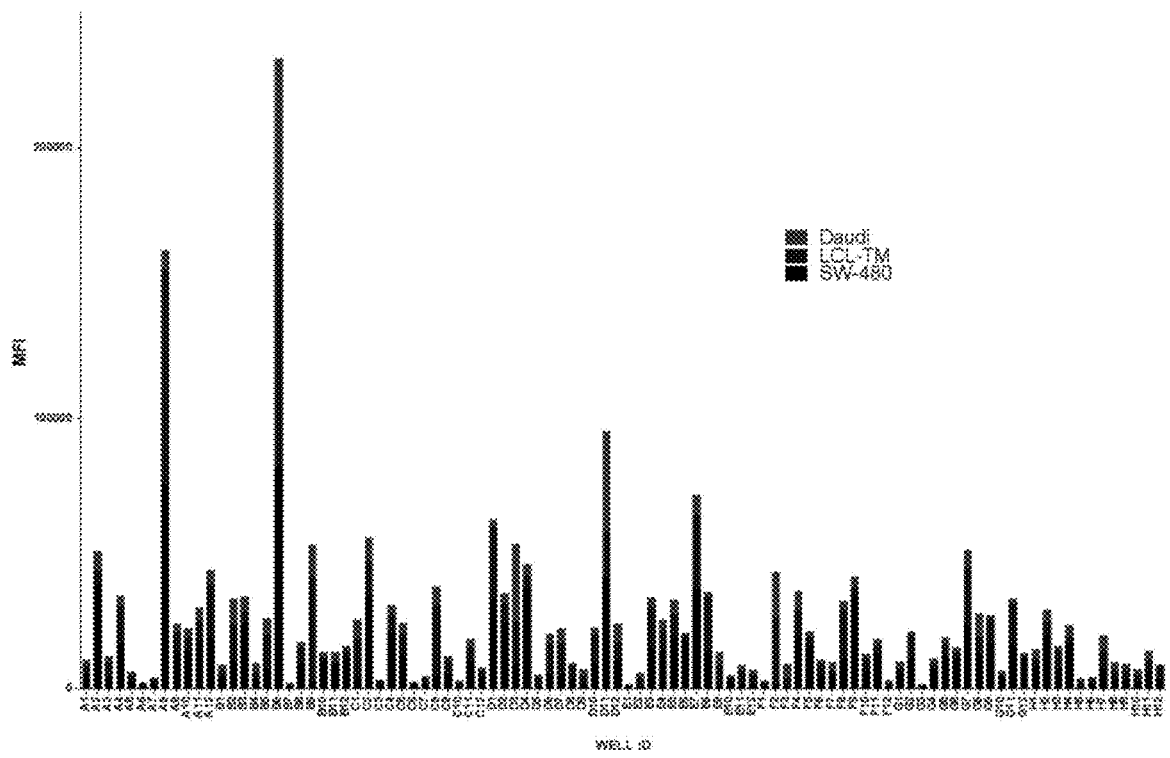
FIG. 9 shows an exemplary screening method in which isolated clones produce antibodies that specifically bound γδTCR reactive tumor cells or a Daudi negative control.

To identify a TCR ligand, TCR-like antibodies, i.e. antibodies recognizing the same epitope as the γδTCR, were generated and were used identify a ligand by immunoprecipitation and mass spectrometry. To raise these antibodies, C57BL/6 mice were immunized with complete cell lines SW480 and LCL-TM that were recognized by the γδTCR, after which hybridomas were produced by fusing mice B-cells to myeloma cells. These hybridomas were cloned by limiting dilution from which clones were isolated that produced antibodies that specifically bound γδTCR reactive tumor cells in an antibody binding screen (FIG. 8A). To further determine the ligand specificity of the antibodies, the γδTCR-targets SW480 and LCL-TM were pre-incubated with hybridoma supernatant and subsequently used in co-cultures to stimulate TEG011. 13 antibodies (or hybridoma supernatants) blocked the activation of the TEG011 substantially, while at least two clones partly inhibited recognition of SW480 without inhibiting the recognition of LCL-TM, as measured by IFNγ ELISpot (FIG. 8A). These data suggest that multiple raised antibodies were able to partially or completely prevent the binding of the γδTCR to its ligand. In contrast, none of the hybridomas produced an antibody that could block the recognition of WT1 RMFPNAPYL (SEQ ID NO: 435) (0201) peptide loaded SW480 by WT1 TCR transduced αβT cells (FIG. 8B), indicating that the blocking was not induced via binding to e.g. adhesion molecules generally needed for T cell activation. From the hybridomas, one antibody completely blocking activity and one partially blocking activity were selected for antibody production and purification. These purified antibodies were coupled to streptavidin beads and subsequently used for ligand-immunoprecipitation in cell lysates of either SW480 or LCL-TM cells. Mass spectrometry analysis resulted with both antibodies in the identification of a panel of mostly MHC class-I molecules (Table 4) suggesting that, in contrast to the general assumption, classical HLA molecules are involved in recognition of tumor cells for this particular γδTCR. To confirm that raised antibodies are specific for classical HLA we incubated LABScreen Single Antigen HLA class I beads with the selected antibodies and measured the beads on Luminex to determine HLA-specificity. FIG. 8C shows that an antibody that completely blocks the binding of a polypeptide described herein has a reactivity limited to a subgroup HLA-A alleles while a partial blocking antibody has a broader specificity towards all HLA class I present on the LABScreen beads.

TABLE 4

Immunoprecipitation with antibodies indicates that HLA molecules are part of the ligand.

| Sample | Accession ID | Gene |
| --- | --- | --- |
| LCL-12 | P30498 | HLA-B |
| LCL-12 | Q29963 | HLA-C |
| LCL-12 | P04439 | HLA-A |
| LCL-12 | P30508 | HLA-C |
| LCL-12 | Q95604 | HLA-C |
| LCL-12 | P30499 | HLA-C |
| LCL-12 | P05534 | HLA-A |
| LCL-12 | P18463 | HLA-B |
| LCL-12 | P04222 | HLA-C |
| LCL-12 | P01892 | HLA-A |
| LCL-12 | P61769 | B2M |
| LCL-12 | P30511 | HLA-F |
| LCL-6 | P05534 | HLA-A |
| LCL-6 | P01892 | HLA-A |
| LCL-6 | P04439 | HLA-A |
| LCL-6 | Q95604 | HLA-C |
| LCL-6 | P30508 | HLA-C |
| LCL-6 | Q29963 | HLA-C |
| SW-12 | P05534 | HLA-A |
| SW-12 | P01892 | HLA-A |
| SW-12 | P10321 | HLA-C |
| SW-12 | P01889 | HLA-B |
| SW-12 | P18464 | HLA-B |
| SW-12 | Q95604 | HLA-C |
| SW-12 | P04222 | HLA-C |
| SW-12 | P17693 | HLA-G |
| SW-12 | P30511 | HLA-F |
| SW-12 | P16403 | HIST1H1C |
| SW-12 | P10412 | HIST1H1E |
| SW-6 | P05534 | HLA-A |

Target Cell Recognition by a Polypeptide Construct Described Herein Comprising a γδTCR Depends on HLA-A*24:02.

Figure 10A:
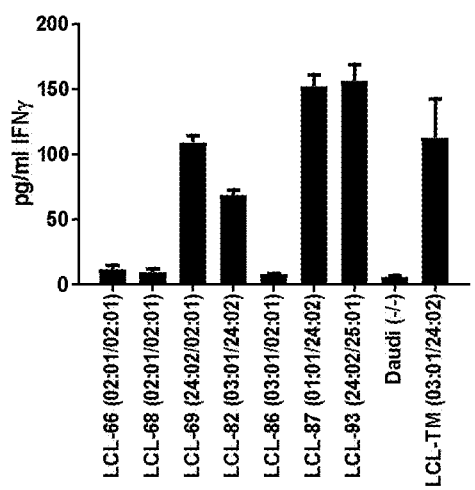
FIG. 10A shows activation of T cells, transduced with the γδTCR described herein by EBV-LCLs with different HLA genotypes and Daudi as a negative control.
Figure 10B:
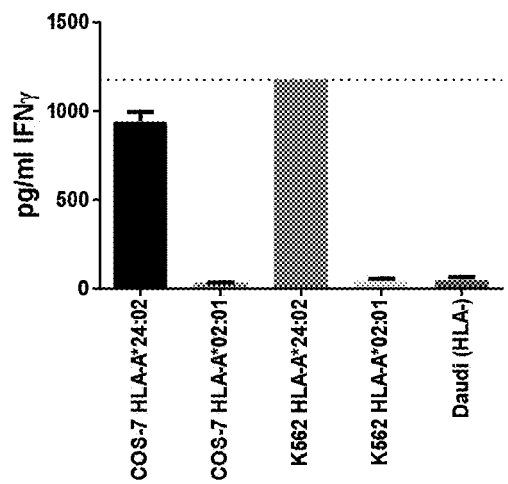
FIG. 10B shows activation of T cells, transduced with the γδTCR FE11 by HLA-A*24:02 or HLA-A*02:01 target cells.
Figure 10C:
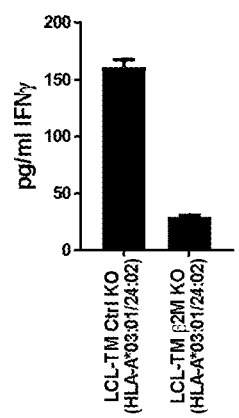
FIG. 10C shows the effect of β2m KO of HLA-A*24:02 positive target cells on the activation of γδTCR FE11 transduced T cells.
Figure 11:
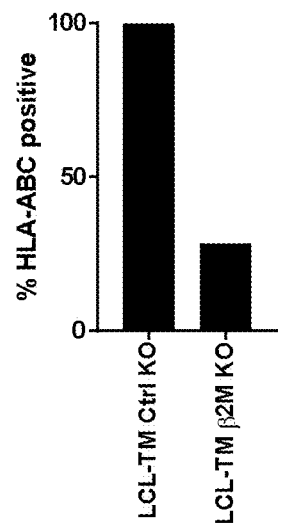
FIG. 11 shows that a decrease in recognition is comparable to the percentage of β2-microglobulin (β2m) KO. CRISPR/Cas9 KO of (β2m) within recognized LCLs reduced recognition of TEG011 as compared to control.

To further narrow down the type of HLA recognized by γδTCR described herein, a large collection of EBV-transformed B cell lines (EBV-LCLs) were obtained from several family pedigrees with a large variety of HLA haplotypes. TEG011 were co-incubated with 7 different CEPH EBV-LCLs, covering multiple possible HLA molecules as suggested by the LABScreen beads (FIG. 8C), Daudi and LCL-TM, and reactivity was assessed by measuring IFNγ-release. Correlating reactivity of TEG011 to the different HLA types, suggested that HLA-A*24:02 haplotype but not HLA-A*02:01 or HLA-A*03:01 (FIG. 10A) was involved in the recognition. To formally confirm HLA-A*24:02 mediated recognition we retrovirally introduced either HLA-A*24:02 or HLA-A*02:01 (control) into the HLA negative cell lines COS-7 (African green monkey kidney fibroblast-like) and K562 (lymphoblast chronic myelogenous leukemia). In both cell lines, introduction of HLA-A*24:02 but not HLA-A*02:01, resulted in significant activation of TEG011 (FIG. 10B). Vice versa, a partial CRISPR/Cas9 KO of β2-microglobulin (β2m) within recognized LCLs (FIG. 11) reduced activation of TEG011 (FIG. 10C) as expected. Re-introducing β2m lead to the reestablishment of target cell recognition, confirming that the observed effect was not caused by an off-target CRISPR/Cas9 KO.

Figure 10D:
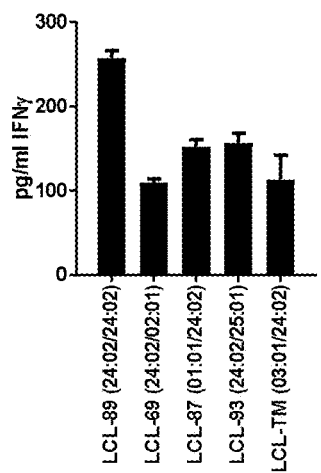
FIG. 10D shows activation of T cells, transduced with the γδTCR FE11 by EBV-LCLs with different either homozygous or heterozygous HLA-A*24:02 expression.
Figure 10E:
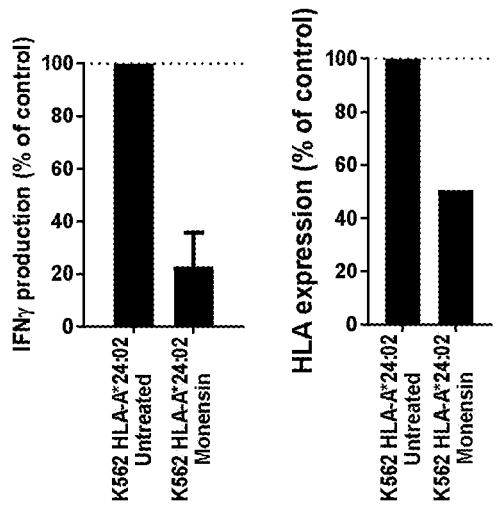
FIG. 10E shows activation of T cells, transduced with the γδTCR described herein by K562 HLA-A*24:02 cells untreated or treated overnight with monensin.
Figure 10F:
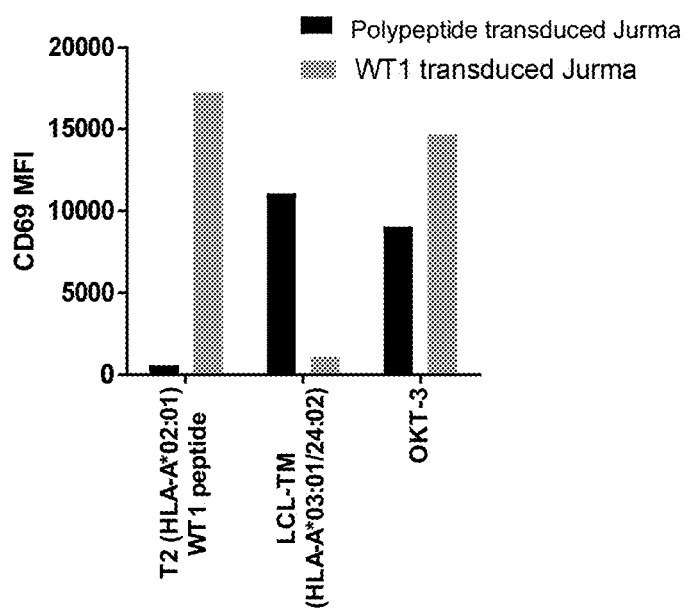
FIG. 10F shows activation of Jurma cells, transduced with γδTCR described herein or αβTCR WT1 (control) by LCL-TM or A2 restricted WT1 peptide loaded T2 cells. CD3 crosslinking by plate-bound α-CD3 mAb clone OKT-3 served as positive control.

In order to test whether density of the ligand is important of the recognition of a target by a γδTCR described herein, we compared activity of TEG011 against LCL cell lines homozygous or heterozygous for HLA-A*24:02. In line with the assumption that density of ligand at a cell surface enhances functional avidity, indeed a higher reactivity of TEG001 was observed against cell lines homozygous for HLA-A*24:02 (FIG. 10D). In addition, reduction of HLA expression by monesin reduced HLA expression and recognition of targets (FIG. 10E). TEGs have been reported to lose allo-reactivity due the down regulation of the endogenous αβTCR due to dominance of the introduced γδTCR. However, in order to formally exclude any activity of endogenous αβTCR within the TEG format, we introduced either γδTCR described herein, or WT1 αβTCR (control) into the TCRβ negative Jurma cell line. The transduced Jurma cells were then co-incubated with WT1 peptide loaded T2 or LCL-TM tumor cell lines, where target-specific activation of T cells was determined by measuring the activation marker CD69 on T cells by flow cytometry. As anticipated, γδTCR transduced Jurmas were only activated by the HLA-A*24:02 expressing LCL-TM, while the WT1 αβTCR transduced Jurmas were only activated by the WT1 loaded T2 cells (FIG. 10F). In conclusion, target cell recognition by the γδTCR FE11 is critically dependent on HLA-A*24:02.

Example 17

Figure 12A:
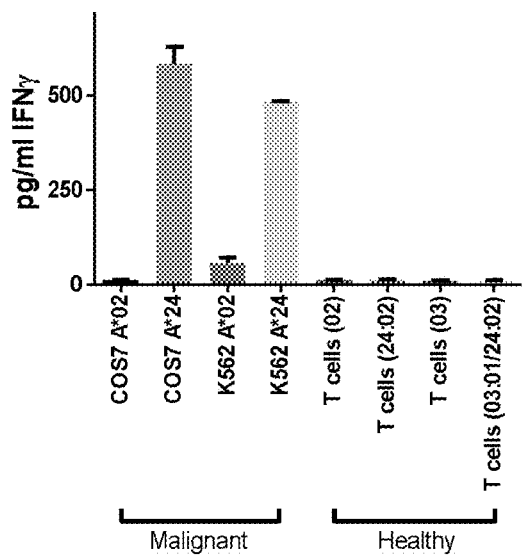
FIG. 12A shows activation of γδTCR described herein transduced T cells on malignant cells and healthy T cells.
Figure 12B:
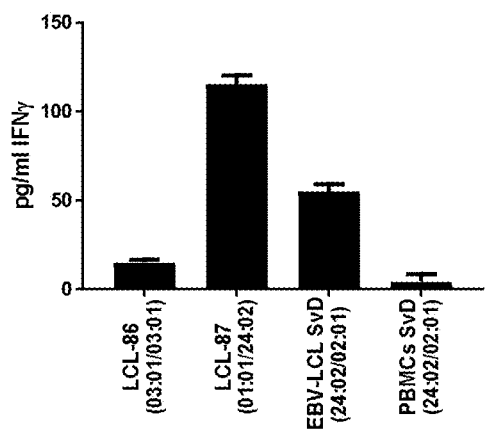
FIG. 12B shows healthy donor B cells that were EBV transformed and co-cultured with γδTCR described herein or mock transduced T cells. Recognition was assessed by measuring IFNγ secretion using ELISA.

Polypeptide Constructs Comprising γδTCR Described Herein Selectively Recognizes HLA-A*24:02 Expressed in Malignant but Not Healthy Cells To assess if recognition is limited to HLA-A*24:02 positive transformed cells TEG011 were co-incubated with healthy primary T cells which were either positive or negative for HLA-A*24:02. In contrast to HLA-A*24:02 positive COS-7 or K562 tumor cells, healthy primary cells were not recognized by TEG011 even when they were positive for HLA-A*24:02 (FIG. 12A). Additionally, HLA-A*24:02 positive B cells immortalized by using EBV transformation significantly activated TEG011, while non-transformed PBMCs of the same donor were not recognized, indicating that in addition to the expression of HLA-A*24:02 allele, malignant transformation is essential for the activation of γδTCR described herein (FIG. 12B).

Binding-Site of Polypeptide Constructs Comprising γδTCR Described Herein

Figures 13A, 13B:
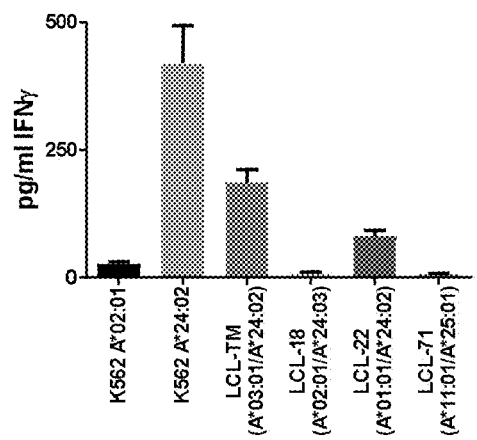
FIG. 13A shows activation, via Interferon-gamma expression, of T cells transduced with the γδTCR described herein by HLA-A*24:03 positive or negative target cells.
FIG. 13B shows alignment of HLA-A*24:02 (SEQ ID NO: 441), 02:01 (SEQ ID NO: 442), 24:03 (SEQ ID NO: 443), and 25:01 (SEQ ID NO: 444) with the two non-homologous amino acids in red.
Figure 14A:
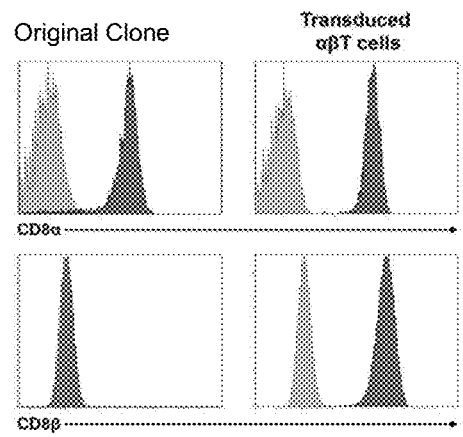
FIG. 14A shows CD8α or CD8β expression on clone FE11 and γδTCR transduced αβ T cells.
Figure 14B:
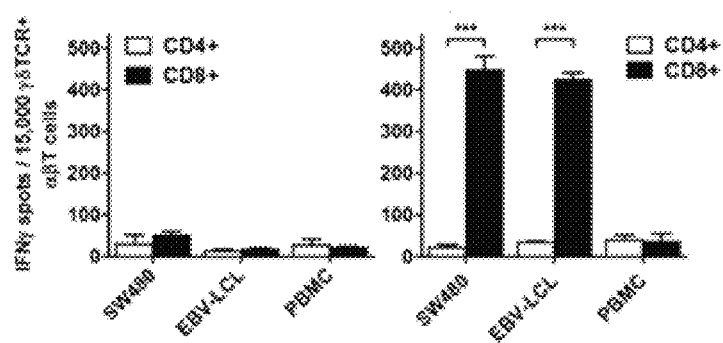
FIG. 14B shows CD4+ and CD8+ αβT cells transduced with the γδTCR described herein were sorted and co-cultured with indicated target cells. T cell activation was assessed by IFNγ ELISPOT.
Figure 14C:
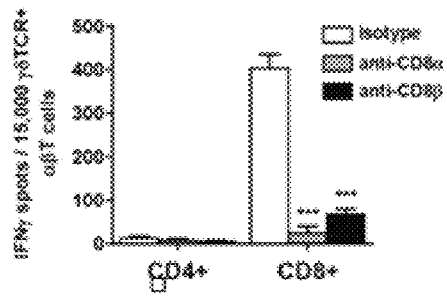
FIG. 14C shows CD4+ and CD8+ αβT cells expressing the γδTCR described herein were co-incubated with SW480 target cells as in (A) but now in the presence of a control antibody or blocking antibodies against CD8α or CD8β.

To further map the putative binding site of polypeptide structural non-homologies between HLA-A*24:02 and HLA-A*02:01, which are classified within different HLA-supertypes as well as HLA-types with more homology to HLA-A*24:02 and functional activity of TEG011 against a range of EBV-LCLs from the CEPH library covering these different HLA-types (FIG. 13A) were used. Reactivity was observed towards the HLA-A*24:02 positive cells, and not towards the strong homologous HLA-A*24:03 EBV-LCL- 71. Sequence alignment (FIG. 14B) revealed that the two amino acids on the α2 helix at position 168 and 169 (asparagine and glycine respectively) are used for recognition of HLA-A*24:02 by TEG011. Structural analyses of the putative binding sites at position 168 and 169 indicated a very close proximity to the peptide binding groove (FIG. 14C). A sequence alignment between HLA-A*24:02 and HLA-A*02:01 is shown in FIG. 5.

Figure 13C:
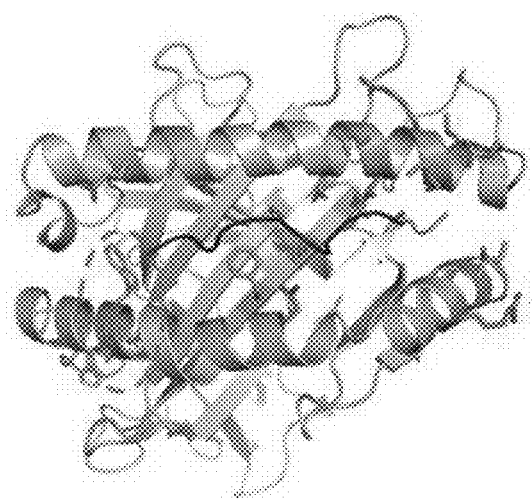
FIG. 13C shows differences between HLA-A*02:01 and HLA-A24:02 mapped on the structure of HLA-A24:02 (pdb: 3wl9), the two non-homologous amino acids between HLA-A*24:02 and HLA-A*24:03 are show in the red circle.
Figure 13D:
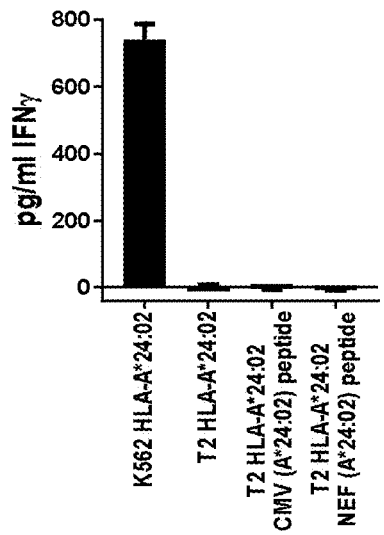
FIG. 13D shows activation of T cells, transduced with the γδTCR described herein, by HLA-A*24:02 transduced TAP deficient T2 cells non-loaded or loaded with the A*24 restricted viral peptides NEF (134-10) or CMV (pp65 341-349).
Figure 13E:
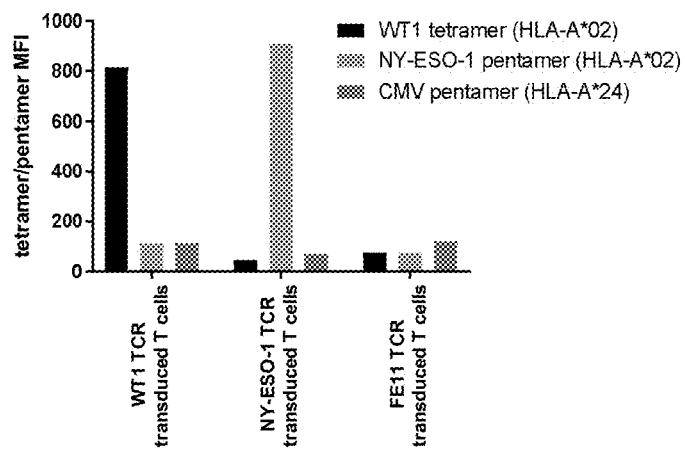
FIG. 13E shows WT1 tetramer, NY-ESO1 pentamer and CMV pentamer binding to WT1 TCR, NY-ESO1 TCR and TCR transduced T cells.
Figure 14D:
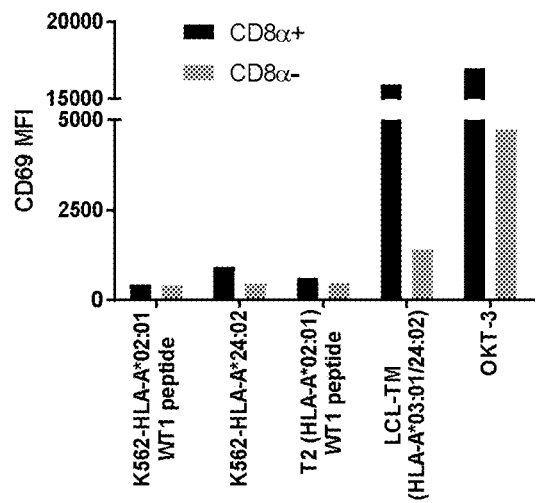
FIG. 14D shows activation of γδTCR described herein transduced Jurma cells by HLA-A*24:02 positive and negative target cells as measured by CD69 upregulation.

Involvement of a Peptide in HLA-A*24:02 Recognition by Polypeptide Constructs Comprising γδTCR Described Herein Due to the close proximity of the putative binding site to the peptide binding groove (FIG. 13C) the role of a peptide in the recognition of HLA-A*24:02 by γδTCR described herein was evaluated. The TAP-deficient cell line T2 was transduced with HLA-A*24:02 and HLA-A*02:01 (control) loaded or not loaded with RYPLTFGWCF (SEQ ID NO: 438) (24:02) and RMFPNAPYL (SEQ ID NO: 435) (02:01) peptide. To confirm the successful loading of HLAs with peptide, stabilization of HLA on the surface of T2 cells was assessed and loaded or unloaded T2 transfectants and co-incubated with TEG011. Despite the fact that the viral peptides were able to stabilize HLA, as indicated by an increased HLA MFI, FE11 TCR T cells did not react towards the unloaded or loaded HLA-A*24:02 transduced T2 cells (FIG. 14D), indicating that the presence of HLA-A*24:02 alone is not sufficient, but that the presentation of an endogenously presented peptide or group of peptide could be key to establish reactivity. In order to confirm the hypothesis that HLA-A*24:02 binding of the γδTCR described herein can be accentuated by additional peptides, TEG011 was co-incubated with a CMV pp65 HLA-A*24:02 restricted pentamer. Whereas the controls, WT1 αβTCR- and NY-ESO-1 αβTCR-transduced T cells with their respective tetramer or pentamer stained positive (FIG. 13E), the TEG011 was not stained by the HLA-A*24:02 restricted pentamer alone.

Figure 13F:
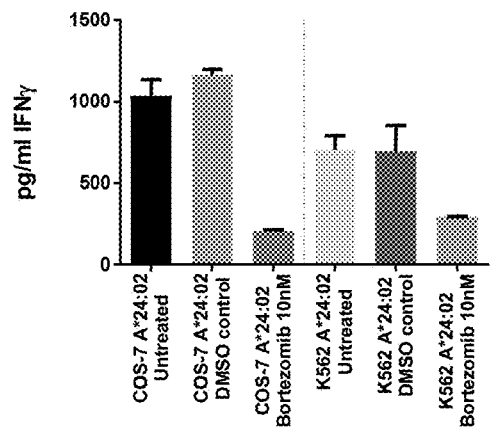
FIG. 13F shows the effect of bortezomib treatment of HLA-A*24:02 transduced target cells on the activation of γδTCR transduced T cells.

To further show that endogenously processed peptides are utilized for reactivity of the cellular peptide processing machinery, the machinery was impeded by inhibiting the proteasome. To achieve this we pre-treated recognized cells with the proteasome inhibitor Bortezomib and assessed the influence on TCR T cell reactivity. Bortezomib treatment lead to a significant decrease in recognition of both HLA-A*24:02 transduced COS-7 and K562 (FIG. 13F), which is not caused by a decrease in HLA expression, as measured by HLA-ABC MFI.

Compartmentalization as a Factor for Recognition

Figure 13G:
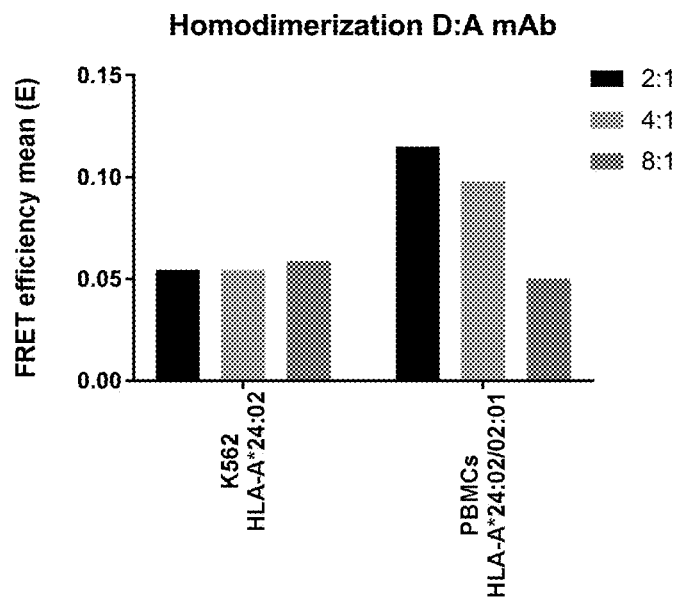
FIG. 13G shows homodimerization was assessed on HLA-A*24:02 positive recognized and non-recognized cells by flow cytometry FRET.
Figure 13H:
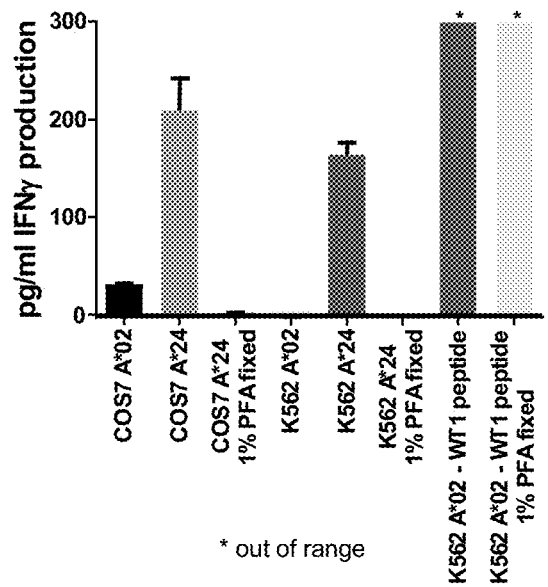
FIG. 13H shows activation of T cells, transduced with the γδTCR described herein or αβTCR WT1 (control), by HLA-A*24:02 transduced COS-7 and K562 or HLA-A*02:01 (control). Where indicated target cells were fixed before coincubation. Where indicated target cells were coincubated with WT1 peptide.

Förster resonance energy transfer (FRET) using flow cytometry as previously described. The FRET data indicate that HLA homodimerizes on non-recognized cells like PBMCs while no homo-dimerization can be observed on HLA-A24:02 positive K562 (FIG. 13G). In order to formally test that membrane mobility of HLA-A24:02 is key for recognition by γδTCR-HLA but not αβTCR-HLA we assessed the effect of paraformaldehyde fixation of target cells. Whereas the recognition of WT1 αβTCR transduced T cells and WT1 peptide loaded target cells was not affected by fixation, the interaction by TEG011 cells and HLA-A*24:02 transduced target cells was completely abolished, indicating that there are differences in compartmentalization (FIG. 13H).

Example 18

γδTCR Described Herein Selectively Recognizes HLA-A*24:02 Expressed in Malignant but Not Healthy Cells In order to show that the γδTCR-HLA interaction differs substantially from classical HLA αβTCR interactions the potential role of co-receptors were evaluated. One candidate due to HLA-I restriction was CD8αα. First, CD8 expression of the original clone in line with previous reports (FIG. 14A) was determined. γδTCR transduced T cells depend on the co-expression of CD8, like the original clone, by sorting γδTCR transduced αβT cells on CD4 and CD8 expression before co-culturing with SW480, LCL-TM or PBMCs (control) (FIG. 14B). In contrast to the FE11 γδT cell clone, most αβT cells express CD8 as a heterodimer of CD8α and CD8β for providing co-stimulation. The role of the CD8αβ heterodimer on γδTCR transduced T cells was assessed by using blocking antibodies for either the CD8α or CD8β chain. Not only CD8α, but also CD8β blocking antibodies completely inhibit recognition of SW480 (FIG. 14C), indicating that either CD8αα or CD8αβ were highly beneficial for recognition.

Figure 14E:
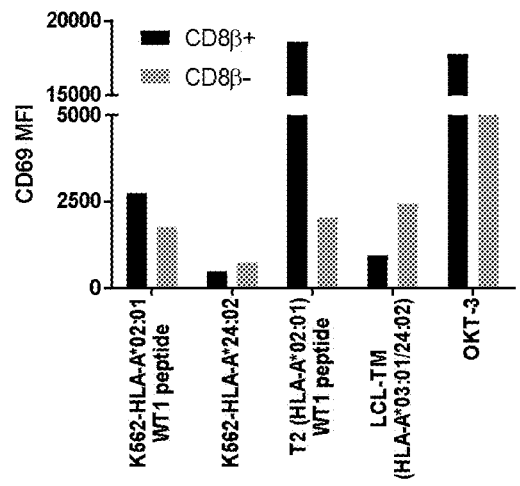
FIG. 14E shows activation of αβTCR WT1 transduced Jurma cells by HLA-A*02:01 positive target cells loaded with HLA-A*02 restricted WT1 peptide. CD3 crosslinking by plate bound α-CD3 mAb clone OKT-3 served as positive control (D+E)
Figure 14F:
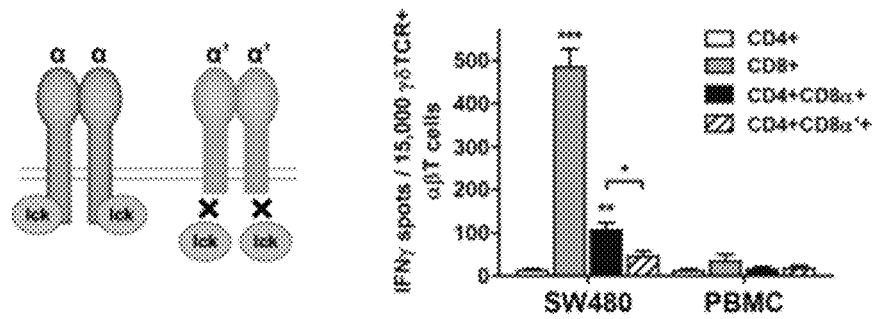
FIG. 14F shows αβT cells were transduced with wildtype CD8α or a truncated, signaling-deficient CD8α variant (CD8α'); alongside the FE11 γδTCR, after which CD4+, CD8+, CD4+CD8α+ and CD4+CD8α'+ T cells populations were sorted. Recognition of healthy PBMCs and SW480 and EBV-LCLs tumor targets was assessed by measuring IFNγ secretion using ELISPOT.

These data have also been confirmed by comparing CD8 positive and CD8 negative Jurma cells expressing γδTCR described herein (FIG. 14D) or αβTCR WT1 (control, FIG. 14E). For co-stimulation of MHC class I-restricted αβTCRs, CD8αβ can play two different roles; it serves as an adhesion molecule that stabilizes the TCR-MHC interaction and it can play an activating role by signaling via LCK. To investigate the role of CD8αα for γδTCR FE11 transduced T cells a truncated variant of CD8α which is signaling deficient due to its inability to bind LCK was generated. After introducing both γδTCR described herein and truncated CD8α (CD8α') in αβT cells we co-cultured them with SW480. A decrease in the amount of IFNγ spots of the CD8α' variant compared to the CD8α wild type variant can be observed (FIG. 14F), indicating that CD8αα indeed plays a co-stimulatory role.

Example 19

Related Sequences for Polypeptides Described Herein

To generate additional sequences that can be useful for polypeptides described herein that selectively bind a desired HLA conformation, site-directed mutagenesis is performed by overlap extension PCR, Ho, S. N., et al., Site-directed mutagenesis by overlap extension using the polymerase chain reaction. Gene, 1989. 77(1): p. 51-9., or whole-plasmid mutagenesis, Miyazaki, K., MEGAWHOP cloning: a method of creating random mutagenesis libraries via megaprimer PCR of whole plasmids. Methods Enzymol, 2011. 498: p. 399-406, using a proofreading polymerase (Phusion; Woke). Mutations are preformed on both the CDR3γ and CDR3δ regions including the entire Jγ1 and Jδ1 segments. Mutated γ- or δ-TCR chains are ligated into the retroviral vector pBullet and sequenced.

TABLE 5

Delta TCR functional region sequences for use in polypeptides described herein

| SEQ ID NO: | Polypeptide Sequence |
|---|---|
| 6 | CALGDSYGGGPLYTDKLIF |
| 7 | CALGESYGGGPLYTDKLIF |
| 8 | CALGNSYGGGPLYTDKLIF |
| 9 | CALGQSYGGGPLYTDKLIF |
| 10 | CALGDTYGGGPLYTDKLIF |

TABLE 5-continued

Delta TCR functional region sequences for use in polypeptides described herein

| SEQ ID NO: | Polypeptide Sequence |
|---|---|
| 11 | CALGETYGGGPLYTDKLIF |
| 12 | CALGNTYGGGPLYTDKLIF |
| 13 | CALGQTYGGGPLYTDKLIF |
| 14 | CALGDSFGGGPLYTDKLIF |
| 15 | CALGESFGGGPLYTDKLIF |
| 16 | CALGNSFGGGPLYTDKLIF |
| 17 | CALGQSFGGGPLYTDKLIF |
| 18 | CALGDTFGGGPLYTDKLIF |
| 19 | CALGETFGGGPLYTDKLIF |
| 20 | CALGNTFGGGPLYTDKLIF |
| 21 | CALGQTFGGGPLYTDKLIF |
| 22 | CALGDSYAGGPLYTDKLIF |
| 23 | CALGESYAGGPLYTDKLIF |
| 24 | CALGNSYAGGPLYTDKLIF |
| 25 | CALGQSYAGGPLYTDKLIF |
| 26 | CALGDTYAGGPLYTDKLIF |
| 27 | CALGETYAGGPLYTDKLIF |
| 28 | CALGNTYAGGPLYTDKLIF |
| 29 | CALGQTYAGGPLYTDKLIF |
| 30 | CALGDSYGAGPLYTDKLIF |
| 31 | CALGESYGAGPLYTDKLIF |
| 32 | CALGNSYGAGPLYTDKLIF |
| 33 | CALGQSYGAGPLYTDKLIF |
| 34 | CALGDTYGAGPLYTDKLIF |
| 35 | CALGETYGAGPLYTDKLIF |
| 36 | CALGNTYGAGPLYTDKLIF |
| 37 | CALGQTYGAGPLYTDKLIF |
| 38 | CALGDSYGGAPLYTDKLIF |
| 39 | CALGESYGGAPLYTDKLIF |
| 40 | CALGNSYGGAPLYTDKLIF |
| 41 | CALGQSYGGAPLYTDKLIF |
| 42 | CALGDTYGGAPLYTDKLIF |
| 43 | CALGETYGGAPLYTDKLIF |
| 44 | CALGNTYGGAPLYTDKLIF |
| 45 | CALGQTYGGAPLYTDKLIF |
| 46 | CALGDSYGGGPIYTDKLIF |
| 47 | CALGESYGGGPIYTDKLIF |
| 48 | CALGNSYGGGPIYTDKLIF |
| 49 | CALGQSYGGGPIYTDKLIF |
| 50 | CALGDTYGGGPIYTDKLIF |
| 51 | CALGETYGGGPIYTDKLIF |
| 52 | CALGNTYGGGPIYTDKLIF |
| 53 | CALGQTYGGGPIYTDKLIF |
| 54 | CALGDSFGGGPIYTDKLIF |
| 55 | CALGESFGGGPIYTDKLIF |
| 56 | CALGNSFGGGPIYTDKLIF |
| 57 | CALGQSFGGGPIYTDKLIF |
| 58 | CALGDSYGGGPLFTDKLIF |
| 59 | CALGESYGGGPLFTDKLIF |
| 60 | CALGNSYGGGPLFTDKLIF |
| 61 | CALGQSYGGGPLFTDKLIF |
| 62 | CALGDTYGGGPLFTDKLIF |
| 63 | CALGETYGGGPLFTDKLIF |
| 64 | CALGNTYGGGPLFTDKLIF |
| 65 | CALGQTYGGGPLFTDKLIF |
| 66 | CALGDSFGGGPLFTDKLIF |
| 67 | CALGESFGGGPLFTDKLIF |
| 68 | CALGNSFGGGPLFTDKLIF |
| 69 | CALGQSFGGGPLFTDKLIF |
| 70 | CALGDSYGGGPIYSDKLIF |
| 71 | CALGESYGGGPIYSDKLIF |
| 72 | CALGNSYGGGPIYSDKLIF |
| 73 | CALGQSYGGGPIYSDKLIF |
| 74 | CALGDTYGGGPIYSDKLIF |
| 75 | CALGETYGGGPIYSDKLIF |
| 76 | CALGNTYGGGPIYSDKLIF |
| 77 | CALGQTYGGGPIYSDKLIF |
| 78 | CALGDSFGGGPIYSDKLIF |
| 79 | CALGESFGGGPIYSDKLIF |
| 80 | CALGNSFGGGPIYSDKLIF |
| 81 | CALGQSFGGGPIYSDKLIF |
| 82 | CALGDSYGGGPLFSDKLIF |
| 83 | CALGESYGGGPLFSDKLIF |
| 84 | CALGNSYGGGPLFSDKLIF |
| 85 | CALGQSYGGGPLFSDKLIF |

TABLE 5-continued

Delta TCR functional region sequences for use in polypeptides described herein

| SEQ ID NO: | Polypeptide Sequence |
|---|---|
| 86 | CALGDTYGGGPLFSDKLIF |
| 87 | CALGETYGGGPLFSDKLIF |
| 88 | CALGNTYGGGPLFSDKLIF |
| 89 | CALGQTYGGGPLFSDKLIF |
| 90 | CALGDSFGGGPLFSDKLIF |
| 91 | CALGESFGGGPLFSDKLIF |
| 92 | CALGNSFGGGPLFSDKLIF |
| 93 | CALGQSFGGGPLFSDKLIF |
| 94 | CALGDSYGGGPIYTEKLIF |
| 95 | CALGESYGGGPIYTEKLIF |
| 96 | CALGNSYGGGPIYTEKLIF |
| 97 | CALGQSYGGGPIYTEKLIF |
| 98 | CALGDTYGGGPIYTEKLIF |
| 99 | CALGETYGGGPIYTEKLIF |
| 100 | CALGNTYGGGPIYTEKLIF |
| 101 | CALGQTYGGGPIYTEKLIF |
| 102 | CALGDSFGGGPIYTEKLIF |
| 103 | CALGESFGGGPIYTEKLIF |
| 104 | CALGNSFGGGPIYTEKLIF |
| 105 | CALGQSFGGGPIYTEKLIF |
| 106 | CALGDSYGGGPLFTEKLIF |
| 107 | CALGESYGGGPLFTEKLIF |
| 108 | CALGNSYGGGPLFTEKLIF |
| 109 | CALGQSYGGGPLFTEKLIF |
| 110 | CALGDTYGGGPLFTEKLIF |
| 111 | CALGETYGGGPLFTEKLIF |
| 112 | CALGNTYGGGPLFTEKLIF |
| 113 | CALGQTYGGGPLFTEKLIF |
| 114 | CALGDSFGGGPLFTEKLIF |
| 115 | CALGESFGGGPLFTEKLIF |
| 116 | CALGNSFGGGPLFTEKLIF |
| 117 | CALGQSFGGGPLFTEKLIF |
| 118 | CALGDSYGGGPIYTNKLIF |
| 119 | CALGESYGGGPIYTNKLIF |
| 120 | CALGNSYGGGPIYTNKLIF |
| 121 | CALGQSYGGGPIYTNKLIF |
| 122 | CALGDTYGGGPIYTNKLIF |
| 123 | CALGETYGGGPIYTNKLIF |
| 124 | CALGNTYGGGPIYTNKLIF |
| 125 | CALGQTYGGGPIYTNKLIF |
| 126 | CALGDSFGGGPIYTNKLIF |
| 127 | CALGESFGGGPIYTNKLIF |
| 128 | CALGNSFGGGPIYTNKLIF |
| 129 | CALGQSFGGGPIYTNKLIF |
| 130 | CALGDSYGGGPLFTNKLIF |
| 131 | CALGESYGGGPLFTNKLIF |
| 132 | CALGNSYGGGPLFTNKLIF |
| 133 | CALGQSYGGGPLFTNKLIF |
| 134 | CALGDTYGGGPLFTNKLIF |
| 135 | CALGETYGGGPLFTNKLIF |
| 136 | CALGNTYGGGPLFTNKLIF |
| 137 | CALGQTYGGGPLFTNKLIF |
| 138 | CALGDSFGGGPLFTNKLIF |
| 139 | CALGESFGGGPLFTNKLIF |
| 140 | CALGNSFGGGPLFTNKLIF |
| 141 | CALGQSFGGGPLFTNKLIF |
| 142 | CALGDSYGGGPIYSEKLIF |
| 143 | CALGESYGGGPIYSEKLIF |
| 144 | CALGNSYGGGPIYSEKLIF |
| 145 | CALGQSYGGGPIYSEKLIF |
| 146 | CALGDTYGGGPIYSEKLIF |
| 147 | CALGETYGGGPIYSEKLIF |
| 148 | CALGNTYGGGPIYSEKLIF |
| 149 | CALGQTYGGGPIYSEKLIF |
| 150 | CALGDSFGGGPIYSEKLIF |
| 151 | CALGESFGGGPIYSEKLIF |
| 152 | CALGNSFGGGPIYSEKLIF |
| 153 | CALGQSFGGGPIYSEKLIF |
| 154 | CALGDSYGGGPLFSEKLIF |
| 155 | CALGESYGGGPLFSEKLIF |
| 156 | CALGNSYGGGPLFSEKLIF |
| 157 | CALGQSYGGGPLFSEKLIF |
| 158 | CALGDTYGGGPLFSEKLIF |
| 159 | CALGETYGGGPLFSEKLIF |
| 160 | CALGNTYGGGPLFSEKLIF |

TABLE 5-continued

Delta TCR functional region sequences for use in polypeptides described herein

| SEQ ID NO: | Polypeptide Sequence |
|---|---|
| 161 | CALGQTYGGGPLFSEKLIF |
| 162 | CALGDSFGGGPLFSEKLIF |
| 163 | CALGESFGGGPLFSEKLIF |
| 164 | CALGNSFGGGPLFSEKLIF |
| 165 | CALGQSFGGGPLFSEKLIF |
| 166 | CALGDSYGGGPIYSNKLIF |
| 167 | CALGESYGGGPIYSNKLIF |
| 168 | CALGNSYGGGPIYSNKLIF |
| 169 | CALGQSYGGGPIYSNKLIF |
| 170 | CALGDTYGGGPIYSNKLIF |
| 171 | CALGETYGGGPIYSNKLIF |
| 172 | CALGNTYGGGPIYSNKLIF |
| 173 | CALGQTYGGGPIYSNKLIF |
| 174 | CALGDSFGGGPIYSNKLIF |
| 175 | CALGESFGGGPIYSNKLIF |
| 176 | CALGNSFGGGPIYSNKLIF |
| 177 | CALGQSFGGGPIYSNKLIF |
| 178 | CALGDSYGGGPLFSNKLIF |
| 179 | CALGESYGGGPLFSNKLIF |
| 180 | CALGNSYGGGPLFSNKLIF |
| 181 | CALGQSYGGGPLFSNKLIF |
| 182 | CALGDTYGGGPLFSNKLIF |
| 183 | CALGETYGGGPLFSNKLIF |
| 184 | CALGNTYGGGPLFSNKLIF |
| 185 | CALGQTYGGGPLFSNKLIF |
| 186 | CALGDSFGGGPLFSNKLIF |
| 187 | CALGESFGGGPLFSNKLIF |
| 188 | CALGNSFGGGPLFSNKLIF |
| 189 | CALGQSFGGGPLFSNKLIF |
| 190 | CALGDSYGGGPIYTDRLIF |
| 191 | CALGESYGGGPIYTDRLIF |
| 192 | CALGNSYGGGPIYTDRLIF |
| 193 | CALGQSYGGGPIYTDRLIF |
| 194 | CALGDTYGGGPIYTDRLIF |
| 195 | CALGETYGGGPIYTDRLIF |
| 196 | CALGNTYGGGPIYTDRLIF |
| 197 | CALGQTYGGGPIYTDRLIF |
| 198 | CALGDSFGGGPIYTDRLIF |

TABLE 5-continued

Delta TCR functional region sequences for use in polypeptides described herein

| SEQ ID NO: | Polypeptide Sequence |
|---|---|
| 199 | CALGESFGGGPIYTDRLIF |
| 200 | CALGNSFGGGPIYTDRLIF |
| 201 | CALGQSFGGGPIYTDRLIF |
| 202 | CALGDSYGGGPLFTDRLIF |
| 203 | CALGESYGGGPLFTDRLIF |
| 204 | CALGNSYGGGPLFTDRLIF |
| 205 | CALGQSYGGGPLFTDRLIF |
| 206 | CALGDTYGGGPLFTDRLIF |
| 207 | CALGETYGGGPLFTDRLIF |
| 208 | CALGNTYGGGPLFTDRLIF |
| 209 | CALGQTYGGGPLFTDRLIF |
| 210 | CALGDSFGGGPLFTDRLIF |
| 211 | CALGESFGGGPLFTDRLIF |
| 212 | CALGNSFGGGPLFTDRLIF |
| 213 | CALGQSFGGGPLFTDRLIF |
| 214 | CALGDSYGGGPIYSDRLIF |
| 215 | CALGESYGGGPIYSDRLIF |
| 216 | CALGNSYGGGPIYSDRLIF |
| 217 | CALGQSYGGGPIYSDRLIF |
| 218 | CALGDTYGGGPIYSDRLIF |
| 219 | CALGETYGGGPIYSDRLIF |
| 220 | CALGNTYGGGPIYSDRLIF |
| 221 | CALGQTYGGGPIYSDRLIF |
| 222 | CALGDSFGGGPIYSDRLIF |
| 223 | CALGESFGGGPIYSDRLIF |
| 224 | CALGNSFGGGPIYSDRLIF |
| 225 | CALGQSFGGGPIYSDRLIF |
| 226 | CALGDSYGGGPLFSDRLIF |
| 227 | CALGESYGGGPLFSDRLIF |
| 228 | CALGNSYGGGPLFSDRLIF |
| 229 | CALGQSYGGGPLFSDRLIF |
| 230 | CALGDTYGGGPLFSDRLIF |
| 231 | CALGETYGGGPLFSDRLIF |
| 232 | CALGNTYGGGPLFSDRLIF |
| 233 | CALGQTYGGGPLFSDRLIF |
| 234 | CALGDSFGGGPLFSDRLIF |
| 235 | CALGESFGGGPLFSDRLIF |

TABLE 5-continued

Delta TCR functional region sequences for use in polypeptides described herein

| SEQ ID NO: | Polypeptide Sequence |
|---|---|
| 236 | CALGNSFGGGPLFSDRLIF |
| 237 | CALGQSFGGGPLFSDRLIF |

TABLE 6

Gamma TCR functional region sequences for use in polypeptides described herein

| SEQ ID NO: | Mutant (FE11 gamma) |
|---|---|
| 238 | CATWDRPEIYYKKLF |
| 239 | CATWERPEIYYKKLF |
| 240 | CATWNRPEIYYKKLF |
| 241 | CATWQRPEIYYKKLF |
| 242 | CATWDKPEIYYKKLF |
| 243 | CATWEKPEIYYKKLF |
| 244 | CATWNKPEIYYKKLF |
| 245 | CATWQKPEIYYKKLF |
| 246 | CATWDRPDIYYKKLF |
| 247 | CATWERPDIYYKKLF |
| 248 | CATWNRPDIYYKKLF |
| 249 | CATWQRPDIYYKKLF |
| 250 | CATWDKPDIYYKKLF |
| 251 | CATWEKPDIYYKKLF |
| 252 | CATWNKPDIYYKKLF |
| 253 | CATWQKPDIYYKKLF |
| 254 | CATWDRPNIYYKKLF |
| 255 | CATWERPNIYYKKLF |
| 256 | CATWNRPNIYYKKLF |
| 257 | CATWQRPNIYYKKLF |
| 258 | CATWDKPNIYYKKLF |
| 259 | CATWEKPNIYYKKLF |
| 260 | CATWNKPNIYYKKLF |
| 261 | CATWQKPNIYYKKLF |
| 262 | CATWDRPQIYYKKLF |
| 263 | CATWERPQIYYKKLF |
| 264 | CATWNRPQIYYKKLF |
| 265 | CATWQRPQIYYKKLF |
| 266 | CATWDKPQIYYKKLF |
| 267 | CATWEKPQIYYKKLF |
| 268 | CATWNKPQIYYKKLF |

TABLE 6-continued

Gamma TCR functional region sequences for use in polypeptides described herein

| SEQ ID NO: | Mutant (FE11 gamma) |
|---|---|
| 269 | CATWQKPQIYYKKLF |
| 270 | CATWDRPELYYKKLF |
| 271 | CATWERPELYYKKLF |
| 272 | CATWNRPELYYKKLF |
| 273 | CATWQRPELYYKKLF |
| 274 | CATWDKPELYYKKLF |
| 275 | CATWEKPELYYKKLF |
| 276 | CATWNKPELYYKKLF |
| 277 | CATWQKPELYYKKLF |
| 278 | CATWDRPDLYYKKLF |
| 279 | CATWERPDLYYKKLF |
| 280 | CATWNRPDLYYKKLF |
| 281 | CATWQRPDLYYKKLF |
| 282 | CATWDKPDLYYKKLF |
| 283 | CATWEKPDLYYKKLF |
| 284 | CATWNKPDLYYKKLF |
| 285 | CATWQKPDLYYKKLF |
| 286 | CATWDRPNLYYKKLF |
| 287 | CATWERPNLYYKKLF |
| 288 | CATWNRPNLYYKKLF |
| 289 | CATWQRPNLYYKKLF |
| 290 | CATWDKPNLYYKKLF |
| 291 | CATWEKPNLYYKKLF |
| 292 | CATWNKPNLYYKKLF |
| 293 | CATWQKPNLYYKKLF |
| 294 | CATWDRPQLYYKKLF |
| 295 | CATWERPQLYYKKLF |
| 296 | CATWNRPQLYYKKLF |
| 297 | CATWQRPQLYYKKLF |
| 298 | CATWDKPQLYYKKLF |
| 299 | CATWEKPQLYYKKLF |
| 300 | CATWNKPQLYYKKLF |
| 301 | CATWQKPQLYYKKLF |
| 302 | CATWDRPEIFYKKLF |
| 303 | CATWERPEIFYKKLF |
| 304 | CATWNRPEIFYKKLF |
| 305 | CATWQRPEIFYKKLF |

TABLE 6-continued

Gamma TCR functional region sequences for use in polypeptides described herein

| SEQ ID NO: | Mutant (FE11 gamma) |
|---|---|
| 306 | CATWDKPEIFYKKLF |
| 307 | CATWEKPEIFYKKLF |
| 308 | CATWNKPEIFYKKLF |
| 309 | CATWQKPEIFYKKLF |
| 310 | CATWDRPDIFYKKLF |
| 311 | CATWERPDIFYKKLF |
| 312 | CATWNRPDIFYKKLF |
| 313 | CATWQRPDIFYKKLF |
| 314 | CATWDKPDIFYKKLF |
| 315 | CATWEKPDIFYKKLF |
| 316 | CATWNKPDIFYKKLF |
| 317 | CATWQKPDIFYKKLF |
| 318 | CATWDRPNIFYKKLF |
| 319 | CATWERPNIFYKKLF |
| 320 | CATWNRPNIFYKKLF |
| 321 | CATWQRPNIFYKKLF |
| 322 | CATWDKPNIFYKKLF |
| 323 | CATWEKPNIFYKKLF |
| 324 | CATWNKPNIFYKKLF |
| 325 | CATWQKPNIFYKKLF |
| 326 | CATWDRPQIFYKKLF |
| 327 | CATWERPQIFYKKLF |
| 328 | CATWNRPQIFYKKLF |
| 329 | CATWQRPQIFYKKLF |
| 330 | CATWDKPQIFYKKLF |
| 331 | CATWEKPQIFYKKLF |
| 332 | CATWNKPQIFYKKLF |
| 333 | CATWQKPQIFYKKLF |
| 334 | CATWDRPELFYKKLF |
| 335 | CATWERPELFYKKLF |
| 336 | CATWNRPELFYKKLF |
| 337 | CATWQRPELFYKKLF |
| 338 | CATWDKPELFYKKLF |
| 339 | CATWEKPELFYKKLF |
| 340 | CATWNKPELFYKKLF |
| 341 | CATWQKPELFYKKLF |
| 342 | CATWDRPDLFYKKLF |
| 343 | CATWERPDLFYKKLF |
| 344 | CATWNRPDLFYKKLF |
| 345 | CATWQRPDLFYKKLF |
| 346 | CATWDKPDLFYKKLF |
| 347 | CATWEKPDLFYKKLF |
| 348 | CATWNKPDLFYKKLF |
| 349 | CATWQKPDLFYKKLF |
| 350 | CATWDRPNLFYKKLF |
| 351 | CATWERPNLFYKKLF |
| 352 | CATWNRPNLFYKKLF |
| 353 | CATWQRPNLFYKKLF |
| 354 | CATWDKPNLFYKKLF |
| 355 | CATWEKPNLFYKKLF |
| 356 | CATWNKPNLFYKKLF |
| 357 | CATWQKPNLFYKKLF |
| 358 | CATWDRPQLFYKKLF |
| 359 | CATWERPQLFYKKLF |
| 360 | CATWNRPQLFYKKLF |
| 361 | CATWQRPQLFYKKLF |
| 362 | CATWDKPQLFYKKLF |
| 363 | CATWEKPQLFYKKLF |
| 364 | CATWNKPQLFYKKLF |
| 365 | CATWQKPQLFYKKLF |
| 366 | CATWERPEVFYKKLF |
| 367 | CATWNRPEVFYKKLF |
| 368 | CATWQRPEVFYKKLF |
| 369 | CATWDKPEVFYKKLF |
| 370 | CATWEKPEVFYKKLF |
| 371 | CATWNKPEVFYKKLF |
| 372 | CATWQKPEVFYKKLF |
| 373 | CATWDRPDVFYKKLF |
| 374 | CATWERPDVFYKKLF |
| 375 | CATWNRPDVFYKKLF |
| 376 | CATWQRPDVFYKKLF |
| 377 | CATWDKPDVFYKKLF |
| 378 | CATWEKPDVFYKKLF |
| 379 | CATWNKPDVFYKKLF |
| 380 | CATWQKPDVFYKKLF |

TABLE 6-continued

Gamma TCR functional region sequences for use in polypeptides described herein

| SEQ ID NO: | Mutant (FE11 gamma) |
|---|---|
| 381 | CATWDRPNVFYKKLF |
| 382 | CATWERPNVFYKKLF |
| 383 | CATWNRPNVFYKKLF |
| 384 | CATWQRPNVFYKKLF |
| 385 | CATWDKPNVFYKKLF |
| 386 | CATWEKPNVFYKKLF |
| 387 | CATWNKPNVFYKKLF |
| 388 | CATWQKPNVFYKKLF |
| 389 | CATWDRPQVFYKKLF |
| 390 | CATWERPQVFYKKLF |
| 391 | CATWNRPQVFYKKLF |
| 392 | CATWQRPQVFYKKLF |
| 393 | CATWDKPQVFYKKLF |
| 394 | CATWEKPQVFYKKLF |
| 395 | CATWNKPQVFYKKLF |
| 396 | CATWQKPQVFYKKLF |
| 397 | CATWERPEVYYKKLF |
| 398 | CATWNRPEVYYKKLF |
| 399 | CATWQRPEVYYKKLF |
| 400 | CATWDKPEVYYKKLF |
| 401 | CATWEKPEVYYKKLF |
| 402 | CATWNKPEVYYKKLF |
| 403 | CATWQKPEVYYKKLF |
| 404 | CATWDRPDVYYKKLF |
| 405 | CATWERPDVYYKKLF |
| 406 | CATWNRPDVYYKKLF |
| 407 | CATWQRPDVYYKKLF |
| 408 | CATWDKPDVYYKKLF |
| 409 | CATWEKPDVYYKKLF |
| 410 | CATWNKPDVYYKKLF |
| 411 | CATWQKPDVYYKKLF |
| 412 | CATWDRPNVYYKKLF |
| 413 | CATWERPNVYYKKLF |
| 414 | CATWNRPNVYYKKLF |
| 415 | CATWQRPNVYYKKLF |
| 416 | CATWDKPNVYYKKLF |
| 417 | CATWEKPNVYYKKLF |
| 418 | CATWNKPNVYYKKLF |
| 419 | CATWQKPNVYYKKLF |
| 420 | CATWDRPQVYYKKLF |
| 421 | CATWERPQVYYKKLF |
| 422 | CATWNRPQVYYKKLF |
| 423 | CATWQRPQVYYKKLF |
| 424 | CATWDKPQVYYKKLF |
| 425 | CATWEKPQVYYKKLF |
| 426 | CATWNKPQVYYKKLF |
| 427 | CATWQKPQVYYKKLF |
| 428 | ATWDRPEIYYKKL |

Example 20

Murine Model of Solid or Hematological Malignancy

The NOD.Cg-Prkcd$^{scid}$ IL2rg$^{tm1Wjt}$/SzJ (NSG) mice were obtained from The Jackson Laboratory (Bar Harbor, Me., USA) and the NOD.Cg-Prkdc Il2rg Tg(HLA-A24)3Dvs/Sz (NSG-A24) mice were kindly provided by Leonard D. Shultz (The Jackson Laboratory). All mice are housed in the specific pathogen-free (SPF) breeding unit of the Central Animal Facility of Utrecht University. Experiments are conducted according to institutional guidelines after acquiring permission from the local ethical committee and in accordance with current Dutch laws on animal experimentation. Mice receive sublethal total body irradiation followed injection of human hematological tumor cells or implantation of human solid tumor cells after which they are treated with TEGs or Mock TCR transduced T cells. Luciferase positive tumors are visualized in vivo by bioluminescent imaging. Mice are anesthetized by isoflurane before they receive an i.p. injection of Luciferin (Promega). Bioluminescence images are acquired by using a third generation cooled GaAs intensified charge-coupled device camera, controlled by the Photo Vision software and analyzed with M³Vision software (all from Photon Imager; Biospace Laboratory, Paris, France). Tumor growth, tumor free survival and overall survival are used to assess TEG anti-tumor activity compared to Mock TCR T cells. TEG persistence in peripheral blood is measured weekly by flow cytometry. Two times a week clinical symptoms are scored including weight measurements. In case the pre-defined human point is reached or the experiment is ended mice are euthanized for a necropsy and pathological screening.

Example 21

Vδ1 γδTCR Library Generation

RNA is extracted from γδT cells obtained by MACS isolation from PBMC of healthy donors using RNeasy kit (Qiagen). Specific cDNA for δTCR and γTCR is synthesized with Superscript® II Reverse Transcriptase (Thermofisher), using a specific primer at the 3' constant region of δTCR or γTCR. Vδ1 TCR DNA is amplified using a Vδ1 gene specific 5' primer and the 3' constant region primer. This DNA is ligated in a retroviral expression plasmid containing a puromycin resistance gene under the same promotor as the δTCR gene. A similar strategy is done for δTCR gene. Gene specific 5' primers for Vγ2/4, Vγ3/5 and Vγ8 and the 3' constant region primer is used to amplify these γTCR genes. The PCR product is ligated in retroviral expression plasmid containing a neomycin resistance gene under the same promotor as the γTCR gene. The ligation mixes are used to transform chemical competent E. coli DH5α cells using a heat shock protocol. The transformed E. coli are used to inoculate an overnight culture for the extraction of plasmid DNA.

Transduction of Jurkat Cells Using the Vδ1-Vγ TCR Library

Phoenix ampho cells are transfected with the retroviral expression plasmids containing Vδ1 TCR genes and the Vγ genes as well as retroviral helper plasmids pHit60 and pColtGalV. 48 hours post transfection the virus containing culture media is used for the transduction of Jurkat cells. This process is repeated once more. Successfully transduced Jurkat cells are selected using 800 µg/ml G418 and 1 µg/ml puromycin. An additional γδTCR MACS isolation is done to include Jurkat cells expressing paired γ and δ TCR chains.

Screening for K562-HLA-A *24:02 Reactive Vδ1 γδTCRs

Jurkat cells transduced with the Vδ1 γδTCR library are incubated overnight with K562 cells at a 1:3 ratio. The cells are stained with anti-CD69-APC and anti-CD3-PE and sorted using flow cytometry. The sorted non-activated Jurkat cells (CD3$^+$CD69$^-$) are rested and expanded for one week before overnight simulation with HLA-A*24:02 transduced K562 cells. The cells are again stained with anti-CD69-APC and anti-CD3-PE and CD3$^+$CD69$^+$ cells are single cell sorted in a 96 well plates. The Vδ1 γδTCR Jurkat clones are again assessed for reactivity for K562-HLA-A*24:02 and non-reactivity for K562 cells. The truly K562-HLA-A*24: 02 reactive Vδ1 γδTCR Jurkat clones are sequenced to determine γ and δ TCR sequences.

Example 22

Stability Testing

A composition or pharmaceutical composition described herein containing at least one polypeptide described herein or a cell, such as an engineered cell expressing a polypeptide described herein is stored in a sealed container at 25° C. or 4° C. and the container is placed in an atmosphere having 30%, 40%, 50%, 60%, 70%, 75%, 80%, 90% or 95% relative humidity. After 1 month, 2 months, 3 months, 6 months, 1 year, 1.5 years, 2 years, 2.5 years or 3 years, at least 50%, 60%, 70%, 80% or 90% of the pharmaceutical composition shall remain as determined by standard protocols.

While specific embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A cell that comprises a polypeptide construct that comprises a γ-TCR polypeptide and a δ-TCR polypeptide, wherein said γ-TCR polypeptide comprises at least 90% identity to residues 19-309 of SEQ ID NO:4, wherein said δ-TCR polypeptide comprises at least 90% identity to residue 21-293 of SEQ ID NO: 5.

2. The cell of claim 1, wherein a CDR3 of said γ-TCR polypeptide comprises at least 90% identity to any one of SEQ ID NO: 2 and SEQ ID NO: 239 to SEQ ID NO: 428.

3. The cell of claim 1, wherein a CDR3 of said δ-TCR polypeptide comprises at least 90% identity to any one of SEQ ID NO: 3 and SEQ ID NO: 7 to SEQ ID NO: 237.

4. The cell of claim 1, wherein said cell is a natural killer (NK) cell, B cell, or T cell, and wherein when said cell is a T cell that is not a γδT cell.

5. A pharmaceutical composition comprising:
   a) said cell of claim 1; and
   b) at least one of: an excipient, a diluent, or a carrier.

6. A method of treating a cancer infection in a subject in need thereof, comprising: administering to said subject an effective amount of a composition comprising the cell of claim 1.

7. The method of claim 6, further comprising: administering a second therapeutic agent to said subject, and wherein said second therapeutic agent is at least one of a cytokine, chemotherapy, radiation, or a combination thereof.

8. The cell of claim 1, wherein said γ-TCR polypeptide is γ5 and said δ-TCR polypeptide is δ1, wherein said γ5 comprises SEQ ID NO:4, and said δ1 comprises SEQ ID NO: 5.

9. A vector comprising a nucleic acid molecule encoding a γ-TCR polypeptide, wherein said γ-TCR polypeptide comprises at least 90% identity to residues 19-309 of SEQ ID NO: 4, and a nucleic acid molecule encoding a δ-TCR polypeptide, wherein said δ-TCR polypeptide comprises at least 90% identity to residues 21-293 of SEQ ID NOS: 5.

* * * * *

SEQUENCE LISTING

```
<160> NUMBER OF SEQ ID NOS: 444

<210> SEQ ID NO 1
<211> LENGTH: 3416
<212> TYPE: DNA
<213> ORGANISM: Homo sapiens

<400> SEQUENCE: 1
gagaagccaa tcagtgtcgt cgcggtcgct gttctaaagt ccgcacgcac ccaccgggac      60
tcagattctc cccagacgcc gaggatggcc gtcatggcgc cccgaaccct cctcctgcta     120
ctctcggggg ccctggccct gacccagacc tgggcgggtg agtgcggggt cgggagggaa     180
accgcctctg cggggagaag caagggggccc tcctggcggg ggcgcaggac cggggagcc     240 gcgccgggag gagggtcggg caggtctcag ccactgctcg cccccaggct cccactccat     300
gaggtatttc ttcacatccg tgtcccggcc cggccgcggg gagccccgct tcatcgccgt     360
gggctacgtg gacgacacgc agttcgtgcg gttcgacagc gacgccgcga gccagaagat     420
ggagccgcgg gcgccgtgga tagagcagga ggggccggag tattgggacc aggagacacg     480
gaatatgaag gcccactcac agactgaccg agcgaacctg gggaccctgc gcggctacta     540
caaccagagc gaggacggtg agtgacccg gcccggggcg caggtcacga ccctcatcc      600 cccacggacg ggccaggtcg cccacagtct ccgggtccga gatccacccc gaagccgcgg     660
gactccgaga cccttgtccc gggagaggcc caggcgcctt tacccggttt cattttcagt     720
ttaggccaaa aatcccccg ggttggtcgg ggcggggcgg ggctcggggg actgggctga     780
```

```
ccgcggggtc ggggccaggt tctcacacca tccagataat gtatggctgc gacgtggggc      840
cggacgggcg cttcctccgc gggtaccggc aggacgccta cgacggcaag gattacatcg      900
ccctgaacga ggacctgcgc tcttggaccg cggcggacat ggcagctcag atcaccaagc      960
gcaagtggga ggcggtccat gcggcggagc agcggagagt ctacctggag gccggtgcg     1020
tggacgggct ccgcagatac ctggagaacg ggaaggagac gctgcagcgc acgggtacca     1080
ggggccacgg ggcgcctccc tgatcgccta tagatctccc gggctggcct cccacaagga     1140
ggggagacaa ttgggaccaa cactagaata tcaccctccc tctggtcctg agggagagga     1200
atcctcctgg gtttccagat cctgtaccag agagtgactc tgaggttccg ccctgctctc     1260
tgacacaatt aagggataaa atctctgaag gagtgacggg aagacgatcc ctcgaatact     1320
gatgagtggt tccctttgac accggcagca gccttgggcc cgtgactttt cctctcaggc     1380
cttgttctct gcttcacact caatgtgtgt gggggtctga gtccagcact tctgagtctc     1440
tcagcctcca ctcaggtcag gaccagaagt cgctgttccc ttctcaggga atagaagatt     1500
atcccaggtg cctgtgtcca ggctggtgtc tgggttctgt gctctcttcc ccatcccggg     1560
tgtcctgtcc attctcaaga tggccacatg cgtgctggtg gagtgtccca tgacagatgc     1620
aaaatgcctg aattttctga ctcttcccgt cagaccccccc caagacacat atgacccacc     1680
accccatctc tgaccatgag gccaccctga ggtgctgggc cctgggcttc taccctgcgg     1740
agatcacact gacctggcag cgggatgggg aggaccagac ccaggacacg gagctcgtgg     1800
agaccaggcc tgcaggggat ggaaccttcc agaagtgggc ggctgtggtg gtgccttctg     1860
gagaggagca gagatacacc tgccatgtgc agcatgaggg tctgcccaag cccctcaccc     1920
tgagatgggg taaggaggga gatgggggtg tcatgtctct tagggaaagc aggagcctct     1980
ctggagacct ttagcagggt cagggccccct caccttcccc tcttttccca gagctgtctt     2040
cccagcccac catccccatc gtgggcatca ttgctggcct ggttctcctt ggagctgtga     2100
tcactggagc tgtggtcgct gccgtgatgt ggaggaggaa gagctcaggt ggagaagggg     2160
tgaagggtgg ggtctgagat ttcttgtctc actgagggtt ccaagcccca gctagaaatg     2220
tgccctgtct cattactggg aagcaccttc cacaatcatg gccgaccca gcctgggccc     2280
tgtgtgccag cacttactct tttgtaaagc acctgttaaa atgaaggaca gatttatcac     2340
cttgattacg gcggtgatgg gacctgatcc cagcagtcac aagtcacagg gaaggtccc     2400
tgaggacaga cctcaggagg gctattggtc caggaccccac acctgctttc ttcatgtttc     2460
ctgatcccgc cctgggtctg cagtcacaca tttctggaaa cttctctggg gtccaagact     2520
aggaggttcc tctaggacct taaggccctg gctccttcct ggtatctcac aggacatttt     2580
cttcccacag atagaaaagg agggagttac actcaggctg caagtaagta tgaaggaggc     2640
tgatgcctga ggtccttggg atattgtgtt tgggagccca tggggagct cacccacccc     2700
acaattcctc ctctagccac atcttctgtg ggatctgacc aggttctgtt tttgttctac     2760
cccaggcagt gacagtgccc agggctctga tgtgtctctc acagcttgta aaggtgagag     2820
cttggagggc ctgatgtgtg ttgggtgttg ggtggaacag tggacacagc tgtgctatgg     2880
ggtttctttg cgttggatgt attgagcatg cgatgggctg tttaaggtgt gacccctcac     2940
tgtgatggat atgaatttgt tcatgaatat tttttctat agtgtgagac agctgccttg     3000
tgtgggactg agaggcaaga gttgttcctg cccttccctt tgtgacttga agaaccctga     3060
cttttgtttct gcaaaggcac ctgcatgtgt ctgtgttcgt gtaggcataa tgtgaggagg     3120
tggggagagc accccacccc catgtccacc atgaccctct tcccacgctg acctgtgctc     3180
```

-continued

```
cctctccaat catctttcct gttccagaga ggtggggctg aggtgtctcc atctctgtct    3240
caacttcatg gtgcactgag ctgtaacttc ttccttccct attaaaatta gaacctgagt    3300
ataaatttac tttctcaaat tcttgccatg agaggttgat gagttaatta aaggagaaga    3360
ttcctaaaat ttgagagaca aaattaatgg aacgcatgag aaccttccag agtcca       3416
```

<210> SEQ ID NO 2
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 2

Cys Ala Thr Trp Asp Arg Pro Glu Ile Tyr Tyr Lys Lys Leu Phe
1               5                   10                  15

<210> SEQ ID NO 3
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 3

Cys Ala Leu Gly Asp Ser Tyr Gly Gly Gly Pro Leu Tyr Thr Asp Lys
1               5                   10                  15

Leu Ile Phe

<210> SEQ ID NO 4
<211> LENGTH: 309
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 4

Met Gly Trp Ala Leu Leu Val Leu Leu Ala Phe Leu Ser Pro Ala Ser
1               5                   10                  15

Gln Lys Ser Ser Asn Leu Glu Gly Gly Thr Lys Ser Val Thr Arg Pro
            20                  25                  30

Thr Arg Ser Ser Ala Glu Ile Thr Cys Asp Leu Thr Val Ile Asn Ala
        35                  40                  45

Phe Tyr Ile His Trp Tyr Leu His Gln Glu Gly Lys Ala Pro Gln Arg
    50                  55                  60

Leu Leu Tyr Tyr Asp Val Ser Asn Ser Lys Asp Val Leu Glu Ser Gly
65                  70                  75                  80

Leu Ser Pro Gly Lys Tyr Tyr Thr His Thr Pro Arg Arg Trp Ser Trp
                85                  90                  95

Ile Leu Ile Leu Arg Asn Leu Ile Glu Asn Asp Ser Gly Val Tyr Tyr
            100                 105                 110

Cys Ala Thr Trp Asp Arg Pro Glu Ile Tyr Tyr Lys Lys Leu Phe Gly
        115                 120                 125

Ser Gly Thr Thr Leu Val Val Thr Asp Lys Gln Leu Asp Ala Asp Val
    130                 135                 140

-continued

Ser Pro Lys Pro Thr Ile Phe Leu Pro Ser Ile Ala Glu Thr Lys Leu
145                 150                 155                 160

Gln Lys Ala Gly Thr Tyr Leu Cys Leu Leu Glu Lys Phe Phe Pro Asp
            165                 170                 175

Val Ile Lys Ile His Trp Glu Glu Lys Ser Asn Thr Ile Leu Gly
        180                 185                 190

Ser Gln Glu Gly Asn Thr Met Lys Thr Asn Asp Thr Tyr Met Lys Phe
        195                 200                 205

Ser Trp Leu Thr Val Pro Glu Lys Ser Leu Asp Lys Glu His Arg Cys
    210                 215                 220

Ile Val Arg His Glu Asn Asn Lys Asn Gly Val Asp Gln Glu Ile Ile
225                 230                 235                 240

Phe Pro Pro Ile Lys Thr Asp Val Ile Thr Met Asp Pro Lys Asp Asn
                245                 250                 255

Cys Ser Lys Asp Ala Asn Asp Thr Leu Leu Leu Gln Leu Thr Asn Thr
            260                 265                 270

Ser Ala Tyr Tyr Met Tyr Leu Leu Leu Leu Lys Ser Val Val Tyr
        275                 280                 285

Phe Ala Ile Ile Thr Cys Cys Leu Leu Arg Arg Thr Ala Phe Cys Cys
        290                 295                 300

Asn Gly Glu Lys Ser
305

<210> SEQ ID NO 5
<211> LENGTH: 293
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Met Val Phe Ser Ser Leu Leu Cys Val Phe Val Ala Phe Ser Tyr Ser
1               5                   10                  15

Gly Ser Ser Val Ala Gln Lys Val Thr Gln Ala Gln Ser Ser Val Ser
            20                  25                  30

Met Pro Val Arg Lys Ala Val Thr Leu Asn Cys Leu Tyr Glu Thr Ser
        35                  40                  45

Trp Trp Ser Tyr Tyr Ile Phe Trp Tyr Lys Gln Leu Pro Ser Lys Glu
    50                  55                  60

Met Ile Phe Leu Ile Arg Gln Gly Ser Asp Glu Gln Asn Ala Lys Ser
65                  70                  75                  80

Gly Arg Tyr Ser Val Asn Phe Lys Lys Ala Lys Ser Val Ala Leu
            85                  90                  95

Thr Ile Ser Ala Leu Gln Leu Glu Asp Ser Ala Lys Tyr Phe Cys Ala
            100                 105                 110

Leu Gly Asp Ser Tyr Gly Gly Pro Leu Tyr Thr Asp Lys Leu Ile
        115                 120                 125

Phe Gly Lys Gly Thr Arg Val Thr Val Glu Pro Arg Ser Gln Pro His
    130                 135                 140

Thr Lys Pro Ser Val Phe Val Met Lys Asn Gly Thr Asn Val Ala Cys
145                 150                 155                 160

Leu Val Lys Glu Phe Tyr Pro Lys Asp Ile Arg Ile Asn Leu Val Ser
                165                 170                 175

```
Ser Lys Lys Ile Thr Glu Phe Asp Pro Ala Ile Val Ile Ser Pro Ser
            180                 185                 190

Gly Lys Tyr Asn Ala Val Lys Leu Gly Lys Tyr Glu Asp Ser Asn Ser
            195                 200             205

Val Thr Cys Ser Val Gln His Asp Asn Lys Thr Val His Ser Thr Asp
        210                 215                 220

Phe Glu Val Lys Thr Asp Ser Thr Asp His Val Lys Pro Lys Glu Thr
225                 230                 235                 240

Glu Asn Thr Lys Gln Pro Ser Lys Ser Cys His Lys Pro Lys Ala Ile
                245                 250                 255

Val His Thr Glu Lys Val Asn Met Met Ser Leu Thr Val Leu Gly Leu
            260                 265                 270

Arg Met Leu Phe Ala Lys Thr Val Ala Val Asn Phe Leu Leu Thr Ala
            275                 280                 285

Lys Leu Phe Phe Leu
        290
```

<210> SEQ ID NO 6
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 6

```
Cys Ala Leu Gly Asp Ser Tyr Gly Gly Gly Pro Leu Tyr Thr Asp Lys
1               5                   10                  15

Leu Ile Phe
```

<210> SEQ ID NO 7
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 7

```
Cys Ala Leu Gly Glu Ser Tyr Gly Gly Gly Pro Leu Tyr Thr Asp Lys
1               5                   10                  15

Leu Ile Phe
```

<210> SEQ ID NO 8
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 8

```
Cys Ala Leu Gly Asn Ser Tyr Gly Gly Gly Pro Leu Tyr Thr Asp Lys
1               5                   10                  15

Leu Ile Phe
```

<210> SEQ ID NO 9
<211> LENGTH: 19
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Cys Ala Leu Gly Gln Ser Tyr Gly Gly Gly Pro Leu Tyr Thr Asp Lys
1               5                   10                  15

Leu Ile Phe

<210> SEQ ID NO 10
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Cys Ala Leu Gly Asp Thr Tyr Gly Gly Gly Pro Leu Tyr Thr Asp Lys
1               5                   10                  15

Leu Ile Phe

<210> SEQ ID NO 11
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Cys Ala Leu Gly Glu Thr Tyr Gly Gly Gly Pro Leu Tyr Thr Asp Lys
1               5                   10                  15

Leu Ile Phe

<210> SEQ ID NO 12
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Cys Ala Leu Gly Asn Thr Tyr Gly Gly Gly Pro Leu Tyr Thr Asp Lys
1               5                   10                  15

Leu Ile Phe

<210> SEQ ID NO 13
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Cys Ala Leu Gly Gln Thr Tyr Gly Gly Gly Pro Leu Tyr Thr Asp Lys
1               5                   10                  15
```

Leu Ile Phe

<210> SEQ ID NO 14
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Cys Ala Leu Gly Asp Ser Phe Gly Gly Gly Pro Leu Tyr Thr Asp Lys
1               5                   10                  15

Leu Ile Phe

<210> SEQ ID NO 15
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Cys Ala Leu Gly Glu Ser Phe Gly Gly Gly Pro Leu Tyr Thr Asp Lys
1               5                   10                  15

Leu Ile Phe

<210> SEQ ID NO 16
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Cys Ala Leu Gly Asn Ser Phe Gly Gly Gly Pro Leu Tyr Thr Asp Lys
1               5                   10                  15

Leu Ile Phe

<210> SEQ ID NO 17
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Cys Ala Leu Gly Gln Ser Phe Gly Gly Gly Pro Leu Tyr Thr Asp Lys
1               5                   10                  15

Leu Ile Phe

<210> SEQ ID NO 18
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 18

Cys Ala Leu Gly Asp Thr Phe Gly Gly Gly Pro Leu Tyr Thr Asp Lys
1               5                   10                  15

Leu Ile Phe

<210> SEQ ID NO 19
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Cys Ala Leu Gly Glu Thr Phe Gly Gly Gly Pro Leu Tyr Thr Asp Lys
1               5                   10                  15

Leu Ile Phe

<210> SEQ ID NO 20
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Cys Ala Leu Gly Asn Thr Phe Gly Gly Gly Pro Leu Tyr Thr Asp Lys
1               5                   10                  15

Leu Ile Phe

<210> SEQ ID NO 21
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Cys Ala Leu Gly Gln Thr Phe Gly Gly Gly Pro Leu Tyr Thr Asp Lys
1               5                   10                  15

Leu Ile Phe

<210> SEQ ID NO 22
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Cys Ala Leu Gly Asp Ser Tyr Ala Gly Gly Pro Leu Tyr Thr Asp Lys
1               5                   10                  15

Leu Ile Phe

<210> SEQ ID NO 23
<211> LENGTH: 19
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Cys Ala Leu Gly Glu Ser Tyr Ala Gly Gly Pro Leu Tyr Thr Asp Lys
1               5                   10                  15

Leu Ile Phe

<210> SEQ ID NO 24
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Cys Ala Leu Gly Asn Ser Tyr Ala Gly Gly Pro Leu Tyr Thr Asp Lys
1               5                   10                  15

Leu Ile Phe

<210> SEQ ID NO 25
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Cys Ala Leu Gly Gln Ser Tyr Ala Gly Gly Pro Leu Tyr Thr Asp Lys
1               5                   10                  15

Leu Ile Phe

<210> SEQ ID NO 26
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Cys Ala Leu Gly Asp Thr Tyr Ala Gly Gly Pro Leu Tyr Thr Asp Lys
1               5                   10                  15

Leu Ile Phe

<210> SEQ ID NO 27
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Cys Ala Leu Gly Glu Thr Tyr Ala Gly Gly Pro Leu Tyr Thr Asp Lys
1               5                   10                  15
```

Leu Ile Phe

<210> SEQ ID NO 28
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Cys Ala Leu Gly Asn Thr Tyr Ala Gly Gly Pro Leu Tyr Thr Asp Lys
1               5                   10                  15

Leu Ile Phe

<210> SEQ ID NO 29
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Cys Ala Leu Gly Gln Thr Tyr Ala Gly Gly Pro Leu Tyr Thr Asp Lys
1               5                   10                  15

Leu Ile Phe

<210> SEQ ID NO 30
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Cys Ala Leu Gly Asp Ser Tyr Gly Ala Gly Pro Leu Tyr Thr Asp Lys
1               5                   10                  15

Leu Ile Phe

<210> SEQ ID NO 31
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Cys Ala Leu Gly Glu Ser Tyr Gly Ala Gly Pro Leu Tyr Thr Asp Lys
1               5                   10                  15

Leu Ile Phe

<210> SEQ ID NO 32
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 32

Cys Ala Leu Gly Asn Ser Tyr Gly Ala Gly Pro Leu Tyr Thr Asp Lys
1               5                   10                  15

Leu Ile Phe

<210> SEQ ID NO 33
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Cys Ala Leu Gly Gln Ser Tyr Gly Ala Gly Pro Leu Tyr Thr Asp Lys
1               5                   10                  15

Leu Ile Phe

<210> SEQ ID NO 34
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Cys Ala Leu Gly Asp Thr Tyr Gly Ala Gly Pro Leu Tyr Thr Asp Lys
1               5                   10                  15

Leu Ile Phe

<210> SEQ ID NO 35
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Cys Ala Leu Gly Glu Thr Tyr Gly Ala Gly Pro Leu Tyr Thr Asp Lys
1               5                   10                  15

Leu Ile Phe

<210> SEQ ID NO 36
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Cys Ala Leu Gly Asn Thr Tyr Gly Ala Gly Pro Leu Tyr Thr Asp Lys
1               5                   10                  15

Leu Ile Phe

<210> SEQ ID NO 37

-continued

```
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Cys Ala Leu Gly Gln Thr Tyr Gly Ala Gly Pro Leu Tyr Thr Asp Lys
1               5                   10                  15

Leu Ile Phe

<210> SEQ ID NO 38
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Cys Ala Leu Gly Asp Ser Tyr Gly Gly Ala Pro Leu Tyr Thr Asp Lys
1               5                   10                  15

Leu Ile Phe

<210> SEQ ID NO 39
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Cys Ala Leu Gly Glu Ser Tyr Gly Gly Ala Pro Leu Tyr Thr Asp Lys
1               5                   10                  15

Leu Ile Phe

<210> SEQ ID NO 40
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Cys Ala Leu Gly Asn Ser Tyr Gly Gly Ala Pro Leu Tyr Thr Asp Lys
1               5                   10                  15

Leu Ile Phe

<210> SEQ ID NO 41
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Cys Ala Leu Gly Gln Ser Tyr Gly Gly Ala Pro Leu Tyr Thr Asp Lys
```

```
1               5                  10                  15
Leu Ile Phe

<210> SEQ ID NO 42
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Cys Ala Leu Gly Asp Thr Tyr Gly Gly Ala Pro Leu Tyr Thr Asp Lys
1               5                  10                  15

Leu Ile Phe

<210> SEQ ID NO 43
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Cys Ala Leu Gly Glu Thr Tyr Gly Gly Ala Pro Leu Tyr Thr Asp Lys
1               5                  10                  15

Leu Ile Phe

<210> SEQ ID NO 44
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Cys Ala Leu Gly Asn Thr Tyr Gly Gly Ala Pro Leu Tyr Thr Asp Lys
1               5                  10                  15

Leu Ile Phe

<210> SEQ ID NO 45
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Cys Ala Leu Gly Gln Thr Tyr Gly Gly Ala Pro Leu Tyr Thr Asp Lys
1               5                  10                  15

Leu Ile Phe

<210> SEQ ID NO 46
<211> LENGTH: 19
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic peptide"

<400> SEQUENCE: 46

Cys Ala Leu Gly Asp Ser Tyr Gly Gly Gly Pro Ile Tyr Thr Asp Lys
1               5                   10                  15

Leu Ile Phe

<210> SEQ ID NO 47
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Cys Ala Leu Gly Glu Ser Tyr Gly Gly Gly Pro Ile Tyr Thr Asp Lys
1               5                   10                  15

Leu Ile Phe

<210> SEQ ID NO 48
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Cys Ala Leu Gly Asn Ser Tyr Gly Gly Gly Pro Ile Tyr Thr Asp Lys
1               5                   10                  15

Leu Ile Phe

<210> SEQ ID NO 49
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Cys Ala Leu Gly Gln Ser Tyr Gly Gly Gly Pro Ile Tyr Thr Asp Lys
1               5                   10                  15

Leu Ile Phe

<210> SEQ ID NO 50
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Cys Ala Leu Gly Asp Thr Tyr Gly Gly Gly Pro Ile Tyr Thr Asp Lys
1               5                   10                  15

Leu Ile Phe

```
<210> SEQ ID NO 51
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Cys Ala Leu Gly Glu Thr Tyr Gly Gly Gly Pro Ile Tyr Thr Asp Lys
1               5                   10                  15

Leu Ile Phe

<210> SEQ ID NO 52
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Cys Ala Leu Gly Asn Thr Tyr Gly Gly Gly Pro Ile Tyr Thr Asp Lys
1               5                   10                  15

Leu Ile Phe

<210> SEQ ID NO 53
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Cys Ala Leu Gly Gln Thr Tyr Gly Gly Gly Pro Ile Tyr Thr Asp Lys
1               5                   10                  15

Leu Ile Phe

<210> SEQ ID NO 54
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Cys Ala Leu Gly Asp Ser Phe Gly Gly Gly Pro Ile Tyr Thr Asp Lys
1               5                   10                  15

Leu Ile Phe

<210> SEQ ID NO 55
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55
```

```
Cys Ala Leu Gly Glu Ser Phe Gly Gly Gly Pro Ile Tyr Thr Asp Lys
1               5                   10                  15

Leu Ile Phe
```

<210> SEQ ID NO 56
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

```
Cys Ala Leu Gly Asn Ser Phe Gly Gly Gly Pro Ile Tyr Thr Asp Lys
1               5                   10                  15

Leu Ile Phe
```

<210> SEQ ID NO 57
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

```
Cys Ala Leu Gly Gln Ser Phe Gly Gly Gly Pro Ile Tyr Thr Asp Lys
1               5                   10                  15

Leu Ile Phe
```

<210> SEQ ID NO 58
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

```
Cys Ala Leu Gly Asp Ser Tyr Gly Gly Gly Pro Leu Phe Thr Asp Lys
1               5                   10                  15

Leu Ile Phe
```

<210> SEQ ID NO 59
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

```
Cys Ala Leu Gly Glu Ser Tyr Gly Gly Gly Pro Leu Phe Thr Asp Lys
1               5                   10                  15

Leu Ile Phe
```

<210> SEQ ID NO 60
<211> LENGTH: 19
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"

<400> SEQUENCE: 60

Cys Ala Leu Gly Asn Ser Tyr Gly Gly Gly Pro Leu Phe Thr Asp Lys
1               5                   10                  15

Leu Ile Phe

<210> SEQ ID NO 61
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Cys Ala Leu Gly Gln Ser Tyr Gly Gly Gly Pro Leu Phe Thr Asp Lys
1               5                   10                  15

Leu Ile Phe

<210> SEQ ID NO 62
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Cys Ala Leu Gly Asp Thr Tyr Gly Gly Gly Pro Leu Phe Thr Asp Lys
1               5                   10                  15

Leu Ile Phe

<210> SEQ ID NO 63
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Cys Ala Leu Gly Glu Thr Tyr Gly Gly Gly Pro Leu Phe Thr Asp Lys
1               5                   10                  15

Leu Ile Phe

<210> SEQ ID NO 64
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Cys Ala Leu Gly Asn Thr Tyr Gly Gly Gly Pro Leu Phe Thr Asp Lys
1               5                   10                  15

Leu Ile Phe
```

<210> SEQ ID NO 65
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Cys Ala Leu Gly Gln Thr Tyr Gly Gly Gly Pro Leu Phe Thr Asp Lys
1               5                   10                  15

Leu Ile Phe

<210> SEQ ID NO 66
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 66

Cys Ala Leu Gly Asp Ser Phe Gly Gly Gly Pro Leu Phe Thr Asp Lys
1               5                   10                  15

Leu Ile Phe

<210> SEQ ID NO 67
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 67

Cys Ala Leu Gly Glu Ser Phe Gly Gly Gly Pro Leu Phe Thr Asp Lys
1               5                   10                  15

Leu Ile Phe

<210> SEQ ID NO 68
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 68

Cys Ala Leu Gly Asn Ser Phe Gly Gly Gly Pro Leu Phe Thr Asp Lys
1               5                   10                  15

Leu Ile Phe

<210> SEQ ID NO 69
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 69

```
Cys Ala Leu Gly Gln Ser Phe Gly Gly Gly Pro Leu Phe Thr Asp Lys
1               5                   10                  15

Leu Ile Phe

<210> SEQ ID NO 70
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 70

Cys Ala Leu Gly Asp Ser Tyr Gly Gly Gly Pro Ile Tyr Ser Asp Lys
1               5                   10                  15

Leu Ile Phe

<210> SEQ ID NO 71
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

Cys Ala Leu Gly Glu Ser Tyr Gly Gly Gly Pro Ile Tyr Ser Asp Lys
1               5                   10                  15

Leu Ile Phe

<210> SEQ ID NO 72
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 72

Cys Ala Leu Gly Asn Ser Tyr Gly Gly Gly Pro Ile Tyr Ser Asp Lys
1               5                   10                  15

Leu Ile Phe

<210> SEQ ID NO 73
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 73

Cys Ala Leu Gly Gln Ser Tyr Gly Gly Gly Pro Ile Tyr Ser Asp Lys
1               5                   10                  15

Leu Ile Phe

<210> SEQ ID NO 74
<211> LENGTH: 19
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 74

Cys Ala Leu Gly Asp Thr Tyr Gly Gly Gly Pro Ile Tyr Ser Asp Lys
1               5                   10                  15

Leu Ile Phe

<210> SEQ ID NO 75
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 75

Cys Ala Leu Gly Glu Thr Tyr Gly Gly Gly Pro Ile Tyr Ser Asp Lys
1               5                   10                  15

Leu Ile Phe

<210> SEQ ID NO 76
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 76

Cys Ala Leu Gly Asn Thr Tyr Gly Gly Gly Pro Ile Tyr Ser Asp Lys
1               5                   10                  15

Leu Ile Phe

<210> SEQ ID NO 77
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 77

Cys Ala Leu Gly Gln Thr Tyr Gly Gly Gly Pro Ile Tyr Ser Asp Lys
1               5                   10                  15

Leu Ile Phe

<210> SEQ ID NO 78
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 78

Cys Ala Leu Gly Asp Ser Phe Gly Gly Gly Pro Ile Tyr Ser Asp Lys
1               5                   10                  15

Leu Ile Phe
```

<210> SEQ ID NO 79
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 79

Cys Ala Leu Gly Glu Ser Phe Gly Gly Gly Pro Ile Tyr Ser Asp Lys
1               5                   10                  15

Leu Ile Phe

<210> SEQ ID NO 80
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 80

Cys Ala Leu Gly Asn Ser Phe Gly Gly Gly Pro Ile Tyr Ser Asp Lys
1               5                   10                  15

Leu Ile Phe

<210> SEQ ID NO 81
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 81

Cys Ala Leu Gly Gln Ser Phe Gly Gly Gly Pro Ile Tyr Ser Asp Lys
1               5                   10                  15

Leu Ile Phe

<210> SEQ ID NO 82
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 82

Cys Ala Leu Gly Asp Ser Tyr Gly Gly Gly Pro Leu Phe Ser Asp Lys
1               5                   10                  15

Leu Ile Phe

<210> SEQ ID NO 83
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 83

Cys Ala Leu Gly Glu Ser Tyr Gly Gly Gly Pro Leu Phe Ser Asp Lys
1               5                   10                  15

Leu Ile Phe

<210> SEQ ID NO 84
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 84

Cys Ala Leu Gly Asn Ser Tyr Gly Gly Gly Pro Leu Phe Ser Asp Lys
1               5                   10                  15

Leu Ile Phe

<210> SEQ ID NO 85
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 85

Cys Ala Leu Gly Gln Ser Tyr Gly Gly Gly Pro Leu Phe Ser Asp Lys
1               5                   10                  15

Leu Ile Phe

<210> SEQ ID NO 86
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 86

Cys Ala Leu Gly Asp Thr Tyr Gly Gly Gly Pro Leu Phe Ser Asp Lys
1               5                   10                  15

Leu Ile Phe

<210> SEQ ID NO 87
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 87

Cys Ala Leu Gly Glu Thr Tyr Gly Gly Gly Pro Leu Phe Ser Asp Lys
1               5                   10                  15

Leu Ile Phe

<210> SEQ ID NO 88
<211> LENGTH: 19
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 88

Cys Ala Leu Gly Asn Thr Tyr Gly Gly Gly Pro Leu Phe Ser Asp Lys
1               5                   10                  15

Leu Ile Phe

<210> SEQ ID NO 89
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 89

Cys Ala Leu Gly Gln Thr Tyr Gly Gly Gly Pro Leu Phe Ser Asp Lys
1               5                   10                  15

Leu Ile Phe

<210> SEQ ID NO 90
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 90

Cys Ala Leu Gly Asp Ser Phe Gly Gly Gly Pro Leu Phe Ser Asp Lys
1               5                   10                  15

Leu Ile Phe

<210> SEQ ID NO 91
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 91

Cys Ala Leu Gly Glu Ser Phe Gly Gly Gly Pro Leu Phe Ser Asp Lys
1               5                   10                  15

Leu Ile Phe

<210> SEQ ID NO 92
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 92

Cys Ala Leu Gly Asn Ser Phe Gly Gly Gly Pro Leu Phe Ser Asp Lys
1               5                   10                  15
```

Leu Ile Phe

<210> SEQ ID NO 93
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 93

Cys Ala Leu Gly Gln Ser Phe Gly Gly Gly Pro Leu Phe Ser Asp Lys
1               5                   10                  15

Leu Ile Phe

<210> SEQ ID NO 94
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 94

Cys Ala Leu Gly Asp Ser Tyr Gly Gly Gly Pro Ile Tyr Thr Glu Lys
1               5                   10                  15

Leu Ile Phe

<210> SEQ ID NO 95
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 95

Cys Ala Leu Gly Glu Ser Tyr Gly Gly Gly Pro Ile Tyr Thr Glu Lys
1               5                   10                  15

Leu Ile Phe

<210> SEQ ID NO 96
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 96

Cys Ala Leu Gly Asn Ser Tyr Gly Gly Gly Pro Ile Tyr Thr Glu Lys
1               5                   10                  15

Leu Ile Phe

<210> SEQ ID NO 97
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 97

Cys Ala Leu Gly Gln Ser Tyr Gly Gly Gly Pro Ile Tyr Thr Glu Lys
1               5                   10                  15

Leu Ile Phe

<210> SEQ ID NO 98
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 98

Cys Ala Leu Gly Asp Thr Tyr Gly Gly Gly Pro Ile Tyr Thr Glu Lys
1               5                   10                  15

Leu Ile Phe

<210> SEQ ID NO 99
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 99

Cys Ala Leu Gly Glu Thr Tyr Gly Gly Gly Pro Ile Tyr Thr Glu Lys
1               5                   10                  15

Leu Ile Phe

<210> SEQ ID NO 100
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 100

Cys Ala Leu Gly Asn Thr Tyr Gly Gly Gly Pro Ile Tyr Thr Glu Lys
1               5                   10                  15

Leu Ile Phe

<210> SEQ ID NO 101
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 101

Cys Ala Leu Gly Gln Thr Tyr Gly Gly Gly Pro Ile Tyr Thr Glu Lys
1               5                   10                  15

Leu Ile Phe

<210> SEQ ID NO 102
<211> LENGTH: 19

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 102

Cys Ala Leu Gly Asp Ser Phe Gly Gly Gly Pro Ile Tyr Thr Glu Lys
1               5                   10                  15

Leu Ile Phe

<210> SEQ ID NO 103
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 103

Cys Ala Leu Gly Glu Ser Phe Gly Gly Gly Pro Ile Tyr Thr Glu Lys
1               5                   10                  15

Leu Ile Phe

<210> SEQ ID NO 104
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 104

Cys Ala Leu Gly Asn Ser Phe Gly Gly Gly Pro Ile Tyr Thr Glu Lys
1               5                   10                  15

Leu Ile Phe

<210> SEQ ID NO 105
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 105

Cys Ala Leu Gly Gln Ser Phe Gly Gly Gly Pro Ile Tyr Thr Glu Lys
1               5                   10                  15

Leu Ile Phe

<210> SEQ ID NO 106
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 106

Cys Ala Leu Gly Asp Ser Tyr Gly Gly Gly Pro Leu Phe Thr Glu Lys
1               5                   10                  15
```

Leu Ile Phe

<210> SEQ ID NO 107
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 107

Cys Ala Leu Gly Glu Ser Tyr Gly Gly Gly Pro Leu Phe Thr Glu Lys
1               5                   10                  15

Leu Ile Phe

<210> SEQ ID NO 108
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 108

Cys Ala Leu Gly Asn Ser Tyr Gly Gly Gly Pro Leu Phe Thr Glu Lys
1               5                   10                  15

Leu Ile Phe

<210> SEQ ID NO 109
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 109

Cys Ala Leu Gly Gln Ser Tyr Gly Gly Gly Pro Leu Phe Thr Glu Lys
1               5                   10                  15

Leu Ile Phe

<210> SEQ ID NO 110
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 110

Cys Ala Leu Gly Asp Thr Tyr Gly Gly Gly Pro Leu Phe Thr Glu Lys
1               5                   10                  15

Leu Ile Phe

<210> SEQ ID NO 111
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 111

Cys Ala Leu Gly Glu Thr Tyr Gly Gly Gly Pro Leu Phe Thr Glu Lys
1               5                   10                  15

Leu Ile Phe

<210> SEQ ID NO 112
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 112

Cys Ala Leu Gly Asn Thr Tyr Gly Gly Gly Pro Leu Phe Thr Glu Lys
1               5                   10                  15

Leu Ile Phe

<210> SEQ ID NO 113
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 113

Cys Ala Leu Gly Gln Thr Tyr Gly Gly Gly Pro Leu Phe Thr Glu Lys
1               5                   10                  15

Leu Ile Phe

<210> SEQ ID NO 114
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 114

Cys Ala Leu Gly Asp Ser Phe Gly Gly Gly Pro Leu Phe Thr Glu Lys
1               5                   10                  15

Leu Ile Phe

<210> SEQ ID NO 115
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 115

Cys Ala Leu Gly Glu Ser Phe Gly Gly Gly Pro Leu Phe Thr Glu Lys
1               5                   10                  15

Leu Ile Phe

<210> SEQ ID NO 116

```
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 116

Cys Ala Leu Gly Asn Ser Phe Gly Gly Gly Pro Leu Phe Thr Glu Lys
1               5                   10                  15

Leu Ile Phe

<210> SEQ ID NO 117
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 117

Cys Ala Leu Gly Gln Ser Phe Gly Gly Gly Pro Leu Phe Thr Glu Lys
1               5                   10                  15

Leu Ile Phe

<210> SEQ ID NO 118
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 118

Cys Ala Leu Gly Asp Ser Tyr Gly Gly Gly Pro Ile Tyr Thr Asn Lys
1               5                   10                  15

Leu Ile Phe

<210> SEQ ID NO 119
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 119

Cys Ala Leu Gly Glu Ser Tyr Gly Gly Gly Pro Ile Tyr Thr Asn Lys
1               5                   10                  15

Leu Ile Phe

<210> SEQ ID NO 120
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 120

Cys Ala Leu Gly Asn Ser Tyr Gly Gly Gly Pro Ile Tyr Thr Asn Lys
```

Leu Ile Phe

<210> SEQ ID NO 121
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 121

Cys Ala Leu Gly Gln Ser Tyr Gly Gly Gly Pro Ile Tyr Thr Asn Lys
1               5                   10                  15

Leu Ile Phe

<210> SEQ ID NO 122
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 122

Cys Ala Leu Gly Asp Thr Tyr Gly Gly Gly Pro Ile Tyr Thr Asn Lys
1               5                   10                  15

Leu Ile Phe

<210> SEQ ID NO 123
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 123

Cys Ala Leu Gly Glu Thr Tyr Gly Gly Gly Pro Ile Tyr Thr Asn Lys
1               5                   10                  15

Leu Ile Phe

<210> SEQ ID NO 124
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 124

Cys Ala Leu Gly Asn Thr Tyr Gly Gly Gly Pro Ile Tyr Thr Asn Lys
1               5                   10                  15

Leu Ile Phe

<210> SEQ ID NO 125
<211> LENGTH: 19
<212> TYPE: PRT
<213> ORGANISM: Artificial Sequence
<220> FEATURE:
<221> NAME/KEY: source

```
<223> OTHER INFORMATION: /note="Description of Artificial Sequence:
      Synthetic peptide"

<400> SEQUENCE: 125

Cys Ala Leu Gly Gln Thr Tyr Gly Gly Gly Pro Ile Tyr Thr Asn Lys
1               5                   10                  15

Leu Ile Phe

<210> SEQ ID NO 126
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 126

Cys Ala Leu Gly Asp Ser Phe Gly Gly Gly Pro Ile Tyr Thr Asn Lys
1               5                   10                  15

Leu Ile Phe

<210> SEQ ID NO 127
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 127

Cys Ala Leu Gly Glu Ser Phe Gly Gly Gly Pro Ile Tyr Thr Asn Lys
1               5                   10                  15

Leu Ile Phe

<210> SEQ ID NO 128
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 128

Cys Ala Leu Gly Asn Ser Phe Gly Gly Gly Pro Ile Tyr Thr Asn Lys
1               5                   10                  15

Leu Ile Phe

<210> SEQ ID NO 129
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 129

Cys Ala Leu Gly Gln Ser Phe Gly Gly Gly Pro Ile Tyr Thr Asn Lys
1               5                   10                  15

Leu Ile Phe
```

```
<210> SEQ ID NO 130
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 130

Cys Ala Leu Gly Asp Ser Tyr Gly Gly Gly Pro Leu Phe Thr Asn Lys
1               5                   10                  15

Leu Ile Phe

<210> SEQ ID NO 131
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 131

Cys Ala Leu Gly Glu Ser Tyr Gly Gly Gly Pro Leu Phe Thr Asn Lys
1               5                   10                  15

Leu Ile Phe

<210> SEQ ID NO 132
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 132

Cys Ala Leu Gly Asn Ser Tyr Gly Gly Gly Pro Leu Phe Thr Asn Lys
1               5                   10                  15

Leu Ile Phe

<210> SEQ ID NO 133
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 133

Cys Ala Leu Gly Gln Ser Tyr Gly Gly Gly Pro Leu Phe Thr Asn Lys
1               5                   10                  15

Leu Ile Phe

<210> SEQ ID NO 134
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 134
```

Cys Ala Leu Gly Asp Thr Tyr Gly Gly Gly Pro Leu Phe Thr Asn Lys
1               5                   10                  15

Leu Ile Phe

<210> SEQ ID NO 135
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 135

Cys Ala Leu Gly Glu Thr Tyr Gly Gly Gly Pro Leu Phe Thr Asn Lys
1               5                   10                  15

Leu Ile Phe

<210> SEQ ID NO 136
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 136

Cys Ala Leu Gly Asn Thr Tyr Gly Gly Gly Pro Leu Phe Thr Asn Lys
1               5                   10                  15

Leu Ile Phe

<210> SEQ ID NO 137
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 137

Cys Ala Leu Gly Gln Thr Tyr Gly Gly Gly Pro Leu Phe Thr Asn Lys
1               5                   10                  15

Leu Ile Phe

<210> SEQ ID NO 138
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 138

Cys Ala Leu Gly Asp Ser Phe Gly Gly Gly Pro Leu Phe Thr Asn Lys
1               5                   10                  15

Leu Ile Phe

<210> SEQ ID NO 139
<211> LENGTH: 19
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"

<400> SEQUENCE: 139

Cys Ala Leu Gly Glu Ser Phe Gly Gly Gly Pro Leu Phe Thr Asn Lys
1               5                   10                  15

Leu Ile Phe

<210> SEQ ID NO 140
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 140

Cys Ala Leu Gly Asn Ser Phe Gly Gly Gly Pro Leu Phe Thr Asn Lys
1               5                   10                  15

Leu Ile Phe

<210> SEQ ID NO 141
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 141

Cys Ala Leu Gly Gln Ser Phe Gly Gly Gly Pro Leu Phe Thr Asn Lys
1               5                   10                  15

Leu Ile Phe

<210> SEQ ID NO 142
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 142

Cys Ala Leu Gly Asp Ser Tyr Gly Gly Gly Pro Ile Tyr Ser Glu Lys
1               5                   10                  15

Leu Ile Phe

<210> SEQ ID NO 143
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 143

Cys Ala Leu Gly Glu Ser Tyr Gly Gly Gly Pro Ile Tyr Ser Glu Lys
1               5                   10                  15

Leu Ile Phe
```

<210> SEQ ID NO 144
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 144

Cys Ala Leu Gly Asn Ser Tyr Gly Gly Gly Pro Ile Tyr Ser Glu Lys
1               5                   10                  15

Leu Ile Phe

<210> SEQ ID NO 145
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 145

Cys Ala Leu Gly Gln Ser Tyr Gly Gly Gly Pro Ile Tyr Ser Glu Lys
1               5                   10                  15

Leu Ile Phe

<210> SEQ ID NO 146
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 146

Cys Ala Leu Gly Asp Thr Tyr Gly Gly Gly Pro Ile Tyr Ser Glu Lys
1               5                   10                  15

Leu Ile Phe

<210> SEQ ID NO 147
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 147

Cys Ala Leu Gly Glu Thr Tyr Gly Gly Gly Pro Ile Tyr Ser Glu Lys
1               5                   10                  15

Leu Ile Phe

<210> SEQ ID NO 148
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 148

-continued

Cys Ala Leu Gly Asn Thr Tyr Gly Gly Gly Pro Ile Tyr Ser Glu Lys
1               5                   10                  15

Leu Ile Phe

<210> SEQ ID NO 149
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 149

Cys Ala Leu Gly Gln Thr Tyr Gly Gly Gly Pro Ile Tyr Ser Glu Lys
1               5                   10                  15

Leu Ile Phe

<210> SEQ ID NO 150
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 150

Cys Ala Leu Gly Asp Ser Phe Gly Gly Gly Pro Ile Tyr Ser Glu Lys
1               5                   10                  15

Leu Ile Phe

<210> SEQ ID NO 151
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 151

Cys Ala Leu Gly Glu Ser Phe Gly Gly Gly Pro Ile Tyr Ser Glu Lys
1               5                   10                  15

Leu Ile Phe

<210> SEQ ID NO 152
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 152

Cys Ala Leu Gly Asn Ser Phe Gly Gly Gly Pro Ile Tyr Ser Glu Lys
1               5                   10                  15

Leu Ile Phe

<210> SEQ ID NO 153
<211> LENGTH: 19
<212> TYPE: PRT
<213> ORGANISM: Artificial Sequence -continued

```
<220> FEATURE:
<221> NAME/KEY: source
<223> OTHER INFORMATION: /note="Description of Artificial Sequence:
      Synthetic peptide"

<400> SEQUENCE: 153

Cys Ala Leu Gly Gln Ser Phe Gly Gly Gly Pro Ile Tyr Ser Glu Lys
1               5                   10                  15

Leu Ile Phe

<210> SEQ ID NO 154
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 154

Cys Ala Leu Gly Asp Ser Tyr Gly Gly Gly Pro Leu Phe Ser Glu Lys
1               5                   10                  15

Leu Ile Phe

<210> SEQ ID NO 155
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 155

Cys Ala Leu Gly Glu Ser Tyr Gly Gly Gly Pro Leu Phe Ser Glu Lys
1               5                   10                  15

Leu Ile Phe

<210> SEQ ID NO 156
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 156

Cys Ala Leu Gly Asn Ser Tyr Gly Gly Gly Pro Leu Phe Ser Glu Lys
1               5                   10                  15

Leu Ile Phe

<210> SEQ ID NO 157
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 157

Cys Ala Leu Gly Gln Ser Tyr Gly Gly Gly Pro Leu Phe Ser Glu Lys
1               5                   10                  15

Leu Ile Phe
```

```
<210> SEQ ID NO 158
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 158

Cys Ala Leu Gly Asp Thr Tyr Gly Gly Gly Pro Leu Phe Ser Glu Lys
1               5                   10                  15

Leu Ile Phe

<210> SEQ ID NO 159
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 159

Cys Ala Leu Gly Glu Thr Tyr Gly Gly Gly Pro Leu Phe Ser Glu Lys
1               5                   10                  15

Leu Ile Phe

<210> SEQ ID NO 160
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 160

Cys Ala Leu Gly Asn Thr Tyr Gly Gly Gly Pro Leu Phe Ser Glu Lys
1               5                   10                  15

Leu Ile Phe

<210> SEQ ID NO 161
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 161

Cys Ala Leu Gly Gln Thr Tyr Gly Gly Gly Pro Leu Phe Ser Glu Lys
1               5                   10                  15

Leu Ile Phe

<210> SEQ ID NO 162
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 162

Cys Ala Leu Gly Asp Ser Phe Gly Gly Gly Pro Leu Phe Ser Glu Lys
1               5                   10                  15

Leu Ile Phe

<210> SEQ ID NO 163
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 163

Cys Ala Leu Gly Glu Ser Phe Gly Gly Gly Pro Leu Phe Ser Glu Lys
1               5                   10                  15

Leu Ile Phe

<210> SEQ ID NO 164
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 164

Cys Ala Leu Gly Asn Ser Phe Gly Gly Gly Pro Leu Phe Ser Glu Lys
1               5                   10                  15

Leu Ile Phe

<210> SEQ ID NO 165
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 165

Cys Ala Leu Gly Gln Ser Phe Gly Gly Gly Pro Leu Phe Ser Glu Lys
1               5                   10                  15

Leu Ile Phe

<210> SEQ ID NO 166
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 166

Cys Ala Leu Gly Asp Ser Tyr Gly Gly Gly Pro Ile Tyr Ser Asn Lys
1               5                   10                  15

Leu Ile Phe

<210> SEQ ID NO 167
<211> LENGTH: 19
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 167

Cys Ala Leu Gly Glu Ser Tyr Gly Gly Gly Pro Ile Tyr Ser Asn Lys
1               5                   10                  15

Leu Ile Phe

<210> SEQ ID NO 168
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 168

Cys Ala Leu Gly Asn Ser Tyr Gly Gly Gly Pro Ile Tyr Ser Asn Lys
1               5                   10                  15

Leu Ile Phe

<210> SEQ ID NO 169
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 169

Cys Ala Leu Gly Gln Ser Tyr Gly Gly Gly Pro Ile Tyr Ser Asn Lys
1               5                   10                  15

Leu Ile Phe

<210> SEQ ID NO 170
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 170

Cys Ala Leu Gly Asp Thr Tyr Gly Gly Gly Pro Ile Tyr Ser Asn Lys
1               5                   10                  15

Leu Ile Phe

<210> SEQ ID NO 171
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 171

Cys Ala Leu Gly Glu Thr Tyr Gly Gly Gly Pro Ile Tyr Ser Asn Lys
1               5                   10                  15
```

Leu Ile Phe

```
<210> SEQ ID NO 172
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 172
```

Cys Ala Leu Gly Asn Thr Tyr Gly Gly Gly Pro Ile Tyr Ser Asn Lys
1               5                   10                  15

Leu Ile Phe

```
<210> SEQ ID NO 173
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 173
```

Cys Ala Leu Gly Gln Thr Tyr Gly Gly Gly Pro Ile Tyr Ser Asn Lys
1               5                   10                  15

Leu Ile Phe

```
<210> SEQ ID NO 174
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 174
```

Cys Ala Leu Gly Asp Ser Phe Gly Gly Gly Pro Ile Tyr Ser Asn Lys
1               5                   10                  15

Leu Ile Phe

```
<210> SEQ ID NO 175
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 175
```

Cys Ala Leu Gly Glu Ser Phe Gly Gly Gly Pro Ile Tyr Ser Asn Lys
1               5                   10                  15

Leu Ile Phe

```
<210> SEQ ID NO 176
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 176

Cys Ala Leu Gly Asn Ser Phe Gly Gly Gly Pro Ile Tyr Ser Asn Lys
1               5                   10                  15

Leu Ile Phe

<210> SEQ ID NO 177
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 177

Cys Ala Leu Gly Gln Ser Phe Gly Gly Gly Pro Ile Tyr Ser Asn Lys
1               5                   10                  15

Leu Ile Phe

<210> SEQ ID NO 178
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 178

Cys Ala Leu Gly Asp Ser Tyr Gly Gly Gly Pro Leu Phe Ser Asn Lys
1               5                   10                  15

Leu Ile Phe

<210> SEQ ID NO 179
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 179

Cys Ala Leu Gly Glu Ser Tyr Gly Gly Gly Pro Leu Phe Ser Asn Lys
1               5                   10                  15

Leu Ile Phe

<210> SEQ ID NO 180
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 180

Cys Ala Leu Gly Asn Ser Tyr Gly Gly Gly Pro Leu Phe Ser Asn Lys
1               5                   10                  15

Leu Ile Phe

<210> SEQ ID NO 181
<211> LENGTH: 19

-continued

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 181

Cys Ala Leu Gly Gln Ser Tyr Gly Gly Gly Pro Leu Phe Ser Asn Lys
1               5                   10                  15

Leu Ile Phe

<210> SEQ ID NO 182
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 182

Cys Ala Leu Gly Asp Thr Tyr Gly Gly Gly Pro Leu Phe Ser Asn Lys
1               5                   10                  15

Leu Ile Phe

<210> SEQ ID NO 183
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 183

Cys Ala Leu Gly Glu Thr Tyr Gly Gly Gly Pro Leu Phe Ser Asn Lys
1               5                   10                  15

Leu Ile Phe

<210> SEQ ID NO 184
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 184

Cys Ala Leu Gly Asn Thr Tyr Gly Gly Gly Pro Leu Phe Ser Asn Lys
1               5                   10                  15

Leu Ile Phe

<210> SEQ ID NO 185
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 185

Cys Ala Leu Gly Gln Thr Tyr Gly Gly Gly Pro Leu Phe Ser Asn Lys
1               5                   10                  15
```

Leu Ile Phe

<210> SEQ ID NO 186
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 186

Cys Ala Leu Gly Asp Ser Phe Gly Gly Gly Pro Leu Phe Ser Asn Lys
1               5                   10                  15

Leu Ile Phe

<210> SEQ ID NO 187
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 187

Cys Ala Leu Gly Glu Ser Phe Gly Gly Gly Pro Leu Phe Ser Asn Lys
1               5                   10                  15

Leu Ile Phe

<210> SEQ ID NO 188
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 188

Cys Ala Leu Gly Asn Ser Phe Gly Gly Gly Pro Leu Phe Ser Asn Lys
1               5                   10                  15

Leu Ile Phe

<210> SEQ ID NO 189
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 189

Cys Ala Leu Gly Gln Ser Phe Gly Gly Gly Pro Leu Phe Ser Asn Lys
1               5                   10                  15

Leu Ile Phe

<210> SEQ ID NO 190
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 190

Cys Ala Leu Gly Asp Ser Tyr Gly Gly Gly Pro Ile Tyr Thr Asp Arg
1               5                   10                  15

Leu Ile Phe

<210> SEQ ID NO 191
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 191

Cys Ala Leu Gly Glu Ser Tyr Gly Gly Gly Pro Ile Tyr Thr Asp Arg
1               5                   10                  15

Leu Ile Phe

<210> SEQ ID NO 192
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 192

Cys Ala Leu Gly Asn Ser Tyr Gly Gly Gly Pro Ile Tyr Thr Asp Arg
1               5                   10                  15

Leu Ile Phe

<210> SEQ ID NO 193
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 193

Cys Ala Leu Gly Gln Ser Tyr Gly Gly Gly Pro Ile Tyr Thr Asp Arg
1               5                   10                  15

Leu Ile Phe

<210> SEQ ID NO 194
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 194

Cys Ala Leu Gly Asp Thr Tyr Gly Gly Gly Pro Ile Tyr Thr Asp Arg
1               5                   10                  15

Leu Ile Phe

<210> SEQ ID NO 195

-continued

```
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 195

Cys Ala Leu Gly Glu Thr Tyr Gly Gly Gly Pro Ile Tyr Thr Asp Arg
1               5                   10                  15

Leu Ile Phe

<210> SEQ ID NO 196
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 196

Cys Ala Leu Gly Asn Thr Tyr Gly Gly Gly Pro Ile Tyr Thr Asp Arg
1               5                   10                  15

Leu Ile Phe

<210> SEQ ID NO 197
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 197

Cys Ala Leu Gly Gln Thr Tyr Gly Gly Gly Pro Ile Tyr Thr Asp Arg
1               5                   10                  15

Leu Ile Phe

<210> SEQ ID NO 198
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 198

Cys Ala Leu Gly Asp Ser Phe Gly Gly Gly Pro Ile Tyr Thr Asp Arg
1               5                   10                  15

Leu Ile Phe

<210> SEQ ID NO 199
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 199

Cys Ala Leu Gly Glu Ser Phe Gly Gly Gly Pro Ile Tyr Thr Asp Arg
```

```
1               5                  10                  15
Leu Ile Phe

<210> SEQ ID NO 200
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 200

Cys Ala Leu Gly Asn Ser Phe Gly Gly Gly Pro Ile Tyr Thr Asp Arg
1               5                  10                  15

Leu Ile Phe

<210> SEQ ID NO 201
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 201

Cys Ala Leu Gly Gln Ser Phe Gly Gly Gly Pro Ile Tyr Thr Asp Arg
1               5                  10                  15

Leu Ile Phe

<210> SEQ ID NO 202
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 202

Cys Ala Leu Gly Asp Ser Tyr Gly Gly Gly Pro Leu Phe Thr Asp Arg
1               5                  10                  15

Leu Ile Phe

<210> SEQ ID NO 203
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 203

Cys Ala Leu Gly Glu Ser Tyr Gly Gly Gly Pro Leu Phe Thr Asp Arg
1               5                  10                  15

Leu Ile Phe

<210> SEQ ID NO 204
<211> LENGTH: 19
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 204

Cys Ala Leu Gly Asn Ser Tyr Gly Gly Gly Pro Leu Phe Thr Asp Arg
1               5                   10                  15

Leu Ile Phe

<210> SEQ ID NO 205
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 205

Cys Ala Leu Gly Gln Ser Tyr Gly Gly Gly Pro Leu Phe Thr Asp Arg
1               5                   10                  15

Leu Ile Phe

<210> SEQ ID NO 206
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 206

Cys Ala Leu Gly Asp Thr Tyr Gly Gly Gly Pro Leu Phe Thr Asp Arg
1               5                   10                  15

Leu Ile Phe

<210> SEQ ID NO 207
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 207

Cys Ala Leu Gly Glu Thr Tyr Gly Gly Gly Pro Leu Phe Thr Asp Arg
1               5                   10                  15

Leu Ile Phe

<210> SEQ ID NO 208
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 208

Cys Ala Leu Gly Asn Thr Tyr Gly Gly Gly Pro Leu Phe Thr Asp Arg
1               5                   10                  15

Leu Ile Phe
```

```
<210> SEQ ID NO 209
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 209

Cys Ala Leu Gly Gln Thr Tyr Gly Gly Gly Pro Leu Phe Thr Asp Arg
1               5                   10                  15

Leu Ile Phe

<210> SEQ ID NO 210
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 210

Cys Ala Leu Gly Asp Ser Phe Gly Gly Gly Pro Leu Phe Thr Asp Arg
1               5                   10                  15

Leu Ile Phe

<210> SEQ ID NO 211
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 211

Cys Ala Leu Gly Glu Ser Phe Gly Gly Gly Pro Leu Phe Thr Asp Arg
1               5                   10                  15

Leu Ile Phe

<210> SEQ ID NO 212
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 212

Cys Ala Leu Gly Asn Ser Phe Gly Gly Gly Pro Leu Phe Thr Asp Arg
1               5                   10                  15

Leu Ile Phe

<210> SEQ ID NO 213
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 213
```

```
Cys Ala Leu Gly Gln Ser Phe Gly Gly Gly Pro Leu Phe Thr Asp Arg
1               5                   10                  15

Leu Ile Phe

<210> SEQ ID NO 214
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 214

Cys Ala Leu Gly Asp Ser Tyr Gly Gly Gly Pro Ile Tyr Ser Asp Arg
1               5                   10                  15

Leu Ile Phe

<210> SEQ ID NO 215
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 215

Cys Ala Leu Gly Glu Ser Tyr Gly Gly Gly Pro Ile Tyr Ser Asp Arg
1               5                   10                  15

Leu Ile Phe

<210> SEQ ID NO 216
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 216

Cys Ala Leu Gly Asn Ser Tyr Gly Gly Gly Pro Ile Tyr Ser Asp Arg
1               5                   10                  15

Leu Ile Phe

<210> SEQ ID NO 217
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 217

Cys Ala Leu Gly Gln Ser Tyr Gly Gly Gly Pro Ile Tyr Ser Asp Arg
1               5                   10                  15

Leu Ile Phe

<210> SEQ ID NO 218
<211> LENGTH: 19
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 218

Cys Ala Leu Gly Asp Thr Tyr Gly Gly Gly Pro Ile Tyr Ser Asp Arg
1               5                   10                  15

Leu Ile Phe

<210> SEQ ID NO 219
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 219

Cys Ala Leu Gly Glu Thr Tyr Gly Gly Gly Pro Ile Tyr Ser Asp Arg
1               5                   10                  15

Leu Ile Phe

<210> SEQ ID NO 220
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 220

Cys Ala Leu Gly Asn Thr Tyr Gly Gly Gly Pro Ile Tyr Ser Asp Arg
1               5                   10                  15

Leu Ile Phe

<210> SEQ ID NO 221
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 221

Cys Ala Leu Gly Gln Thr Tyr Gly Gly Gly Pro Ile Tyr Ser Asp Arg
1               5                   10                  15

Leu Ile Phe

<210> SEQ ID NO 222
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 222

Cys Ala Leu Gly Asp Ser Phe Gly Gly Gly Pro Ile Tyr Ser Asp Arg
1               5                   10                  15

Leu Ile Phe
```

```
<210> SEQ ID NO 223
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 223

Cys Ala Leu Gly Glu Ser Phe Gly Gly Gly Pro Ile Tyr Ser Asp Arg
1               5                   10                  15

Leu Ile Phe

<210> SEQ ID NO 224
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 224

Cys Ala Leu Gly Asn Ser Phe Gly Gly Gly Pro Ile Tyr Ser Asp Arg
1               5                   10                  15

Leu Ile Phe

<210> SEQ ID NO 225
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 225

Cys Ala Leu Gly Gln Ser Phe Gly Gly Gly Pro Ile Tyr Ser Asp Arg
1               5                   10                  15

Leu Ile Phe

<210> SEQ ID NO 226
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 226

Cys Ala Leu Gly Asp Ser Tyr Gly Gly Gly Pro Leu Phe Ser Asp Arg
1               5                   10                  15

Leu Ile Phe

<210> SEQ ID NO 227
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 227
```

Cys Ala Leu Gly Glu Ser Tyr Gly Gly Gly Pro Leu Phe Ser Asp Arg
1               5                   10                  15

Leu Ile Phe

<210> SEQ ID NO 228
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 228

Cys Ala Leu Gly Asn Ser Tyr Gly Gly Gly Pro Leu Phe Ser Asp Arg
1               5                   10                  15

Leu Ile Phe

<210> SEQ ID NO 229
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 229

Cys Ala Leu Gly Gln Ser Tyr Gly Gly Gly Pro Leu Phe Ser Asp Arg
1               5                   10                  15

Leu Ile Phe

<210> SEQ ID NO 230
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 230

Cys Ala Leu Gly Asp Thr Tyr Gly Gly Gly Pro Leu Phe Ser Asp Arg
1               5                   10                  15

Leu Ile Phe

<210> SEQ ID NO 231
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 231

Cys Ala Leu Gly Glu Thr Tyr Gly Gly Gly Pro Leu Phe Ser Asp Arg
1               5                   10                  15

Leu Ile Phe

<210> SEQ ID NO 232
<211> LENGTH: 19
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic peptide"

<400> SEQUENCE: 232

Cys Ala Leu Gly Asn Thr Tyr Gly Gly Gly Pro Leu Phe Ser Asp Arg
1               5                   10                  15

Leu Ile Phe

<210> SEQ ID NO 233
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 233

Cys Ala Leu Gly Gln Thr Tyr Gly Gly Gly Pro Leu Phe Ser Asp Arg
1               5                   10                  15

Leu Ile Phe

<210> SEQ ID NO 234
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 234

Cys Ala Leu Gly Asp Ser Phe Gly Gly Gly Pro Leu Phe Ser Asp Arg
1               5                   10                  15

Leu Ile Phe

<210> SEQ ID NO 235
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 235

Cys Ala Leu Gly Glu Ser Phe Gly Gly Gly Pro Leu Phe Ser Asp Arg
1               5                   10                  15

Leu Ile Phe

<210> SEQ ID NO 236
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 236

Cys Ala Leu Gly Asn Ser Phe Gly Gly Gly Pro Leu Phe Ser Asp Arg
1               5                   10                  15

Leu Ile Phe
```

<210> SEQ ID NO 237
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 237

Cys Ala Leu Gly Gln Ser Phe Gly Gly Gly Pro Leu Phe Ser Asp Arg
1               5                   10                  15

Leu Ile Phe

<210> SEQ ID NO 238
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 238

Cys Ala Thr Trp Asp Arg Pro Glu Ile Tyr Tyr Lys Lys Leu Phe
1               5                   10                  15

<210> SEQ ID NO 239
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 239

Cys Ala Thr Trp Glu Arg Pro Glu Ile Tyr Tyr Lys Lys Leu Phe
1               5                   10                  15

<210> SEQ ID NO 240
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 240

Cys Ala Thr Trp Asn Arg Pro Glu Ile Tyr Tyr Lys Lys Leu Phe
1               5                   10                  15

<210> SEQ ID NO 241
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 241

Cys Ala Thr Trp Gln Arg Pro Glu Ile Tyr Tyr Lys Lys Leu Phe
1               5                   10                  15

```
<210> SEQ ID NO 242
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 242

Cys Ala Thr Trp Asp Lys Pro Glu Ile Tyr Tyr Lys Lys Leu Phe
1               5                   10                  15

<210> SEQ ID NO 243
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 243

Cys Ala Thr Trp Glu Lys Pro Glu Ile Tyr Tyr Lys Lys Leu Phe
1               5                   10                  15

<210> SEQ ID NO 244
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 244

Cys Ala Thr Trp Asn Lys Pro Glu Ile Tyr Tyr Lys Lys Leu Phe
1               5                   10                  15

<210> SEQ ID NO 245
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 245

Cys Ala Thr Trp Gln Lys Pro Glu Ile Tyr Tyr Lys Lys Leu Phe
1               5                   10                  15

<210> SEQ ID NO 246
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 246

Cys Ala Thr Trp Asp Arg Pro Asp Ile Tyr Tyr Lys Lys Leu Phe
1               5                   10                  15

<210> SEQ ID NO 247
<211> LENGTH: 15
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 247

Cys Ala Thr Trp Glu Arg Pro Asp Ile Tyr Tyr Lys Lys Leu Phe
1               5                   10                  15

<210> SEQ ID NO 248
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 248

Cys Ala Thr Trp Asn Arg Pro Asp Ile Tyr Tyr Lys Lys Leu Phe
1               5                   10                  15

<210> SEQ ID NO 249
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 249

Cys Ala Thr Trp Gln Arg Pro Asp Ile Tyr Tyr Lys Lys Leu Phe
1               5                   10                  15

<210> SEQ ID NO 250
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 250

Cys Ala Thr Trp Asp Lys Pro Asp Ile Tyr Tyr Lys Lys Leu Phe
1               5                   10                  15

<210> SEQ ID NO 251
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 251

Cys Ala Thr Trp Glu Lys Pro Asp Ile Tyr Tyr Lys Lys Leu Phe
1               5                   10                  15

<210> SEQ ID NO 252
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 252

Cys Ala Thr Trp Asn Lys Pro Asp Ile Tyr Tyr Lys Lys Leu Phe
1               5                   10                  15

<210> SEQ ID NO 253
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 253

Cys Ala Thr Trp Gln Lys Pro Asp Ile Tyr Tyr Lys Lys Leu Phe
1               5                   10                  15

<210> SEQ ID NO 254
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 254

Cys Ala Thr Trp Asp Arg Pro Asn Ile Tyr Tyr Lys Lys Leu Phe
1               5                   10                  15

<210> SEQ ID NO 255
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 255

Cys Ala Thr Trp Glu Arg Pro Asn Ile Tyr Tyr Lys Lys Leu Phe
1               5                   10                  15

<210> SEQ ID NO 256
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 256

Cys Ala Thr Trp Asn Arg Pro Asn Ile Tyr Tyr Lys Lys Leu Phe
1               5                   10                  15

<210> SEQ ID NO 257
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 257

Cys Ala Thr Trp Gln Arg Pro Asn Ile Tyr Tyr Lys Lys Leu Phe
```

```
<210> SEQ ID NO 258
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 258

Cys Ala Thr Trp Asp Lys Pro Asn Ile Tyr Tyr Lys Lys Leu Phe
1               5                   10                  15

<210> SEQ ID NO 259
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 259

Cys Ala Thr Trp Glu Lys Pro Asn Ile Tyr Tyr Lys Lys Leu Phe
1               5                   10                  15

<210> SEQ ID NO 260
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 260

Cys Ala Thr Trp Asn Lys Pro Asn Ile Tyr Tyr Lys Lys Leu Phe
1               5                   10                  15

<210> SEQ ID NO 261
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 261

Cys Ala Thr Trp Gln Lys Pro Asn Ile Tyr Tyr Lys Lys Leu Phe
1               5                   10                  15

<210> SEQ ID NO 262
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 262

Cys Ala Thr Trp Asp Arg Pro Gln Ile Tyr Tyr Lys Lys Leu Phe
1               5                   10                  15

<210> SEQ ID NO 263
```

```
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 263

Cys Ala Thr Trp Glu Arg Pro Gln Ile Tyr Tyr Lys Lys Leu Phe
1               5                   10                  15

<210> SEQ ID NO 264
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 264

Cys Ala Thr Trp Asn Arg Pro Gln Ile Tyr Tyr Lys Lys Leu Phe
1               5                   10                  15

<210> SEQ ID NO 265
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 265

Cys Ala Thr Trp Gln Arg Pro Gln Ile Tyr Tyr Lys Lys Leu Phe
1               5                   10                  15

<210> SEQ ID NO 266
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 266

Cys Ala Thr Trp Asp Lys Pro Gln Ile Tyr Tyr Lys Lys Leu Phe
1               5                   10                  15

<210> SEQ ID NO 267
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 267

Cys Ala Thr Trp Glu Lys Pro Gln Ile Tyr Tyr Lys Lys Leu Phe
1               5                   10                  15

<210> SEQ ID NO 268
<211> LENGTH: 15
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 268

Cys Ala Thr Trp Asn Lys Pro Gln Ile Tyr Tyr Lys Lys Leu Phe
1               5                   10                  15

<210> SEQ ID NO 269
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 269

Cys Ala Thr Trp Gln Lys Pro Gln Ile Tyr Tyr Lys Lys Leu Phe
1               5                   10                  15

<210> SEQ ID NO 270
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 270

Cys Ala Thr Trp Asp Arg Pro Glu Leu Tyr Tyr Lys Lys Leu Phe
1               5                   10                  15

<210> SEQ ID NO 271
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 271

Cys Ala Thr Trp Glu Arg Pro Glu Leu Tyr Tyr Lys Lys Leu Phe
1               5                   10                  15

<210> SEQ ID NO 272
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 272

Cys Ala Thr Trp Asn Arg Pro Glu Leu Tyr Tyr Lys Lys Leu Phe
1               5                   10                  15

<210> SEQ ID NO 273
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 273

Cys Ala Thr Trp Gln Arg Pro Glu Leu Tyr Tyr Lys Lys Leu Phe
1               5                   10                  15

<210> SEQ ID NO 274
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 274

Cys Ala Thr Trp Asp Lys Pro Glu Leu Tyr Tyr Lys Lys Leu Phe
1               5                   10                  15

<210> SEQ ID NO 275
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 275

Cys Ala Thr Trp Glu Lys Pro Glu Leu Tyr Tyr Lys Lys Leu Phe
1               5                   10                  15

<210> SEQ ID NO 276
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 276

Cys Ala Thr Trp Asn Lys Pro Glu Leu Tyr Tyr Lys Lys Leu Phe
1               5                   10                  15

<210> SEQ ID NO 277
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 277

Cys Ala Thr Trp Gln Lys Pro Glu Leu Tyr Tyr Lys Lys Leu Phe
1               5                   10                  15

<210> SEQ ID NO 278
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 278

Cys Ala Thr Trp Asp Arg Pro Asp Leu Tyr Tyr Lys Lys Leu Phe
1               5                   10                  15
```

```
<210> SEQ ID NO 279
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 279

Cys Ala Thr Trp Glu Arg Pro Asp Leu Tyr Tyr Lys Lys Leu Phe
1               5                   10                  15

<210> SEQ ID NO 280
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 280

Cys Ala Thr Trp Asn Arg Pro Asp Leu Tyr Tyr Lys Lys Leu Phe
1               5                   10                  15

<210> SEQ ID NO 281
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 281

Cys Ala Thr Trp Gln Arg Pro Asp Leu Tyr Tyr Lys Lys Leu Phe
1               5                   10                  15

<210> SEQ ID NO 282
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 282

Cys Ala Thr Trp Asp Lys Pro Asp Leu Tyr Tyr Lys Lys Leu Phe
1               5                   10                  15

<210> SEQ ID NO 283
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 283

Cys Ala Thr Trp Glu Lys Pro Asp Leu Tyr Tyr Lys Lys Leu Phe
1               5                   10                  15

<210> SEQ ID NO 284
<211> LENGTH: 15
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 284

Cys Ala Thr Trp Asn Lys Pro Asp Leu Tyr Tyr Lys Lys Leu Phe
1               5                   10                  15

<210> SEQ ID NO 285
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 285

Cys Ala Thr Trp Gln Lys Pro Asp Leu Tyr Tyr Lys Lys Leu Phe
1               5                   10                  15

<210> SEQ ID NO 286
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 286

Cys Ala Thr Trp Asp Arg Pro Asn Leu Tyr Tyr Lys Lys Leu Phe
1               5                   10                  15

<210> SEQ ID NO 287
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 287

Cys Ala Thr Trp Glu Arg Pro Asn Leu Tyr Tyr Lys Lys Leu Phe
1               5                   10                  15

<210> SEQ ID NO 288
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 288

Cys Ala Thr Trp Asn Arg Pro Asn Leu Tyr Tyr Lys Lys Leu Phe
1               5                   10                  15

<210> SEQ ID NO 289
<211> LENGTH: 15
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic peptide"

<400> SEQUENCE: 289

Cys Ala Thr Trp Gln Arg Pro Asn Leu Tyr Tyr Lys Lys Leu Phe
1               5                   10                  15

<210> SEQ ID NO 290
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 290

Cys Ala Thr Trp Asp Lys Pro Asn Leu Tyr Tyr Lys Lys Leu Phe
1               5                   10                  15

<210> SEQ ID NO 291
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 291

Cys Ala Thr Trp Glu Lys Pro Asn Leu Tyr Tyr Lys Lys Leu Phe
1               5                   10                  15

<210> SEQ ID NO 292
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 292

Cys Ala Thr Trp Asn Lys Pro Asn Leu Tyr Tyr Lys Lys Leu Phe
1               5                   10                  15

<210> SEQ ID NO 293
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 293

Cys Ala Thr Trp Gln Lys Pro Asn Leu Tyr Tyr Lys Lys Leu Phe
1               5                   10                  15

<210> SEQ ID NO 294
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 294

Cys Ala Thr Trp Asp Arg Pro Gln Leu Tyr Tyr Lys Lys Leu Phe
1               5                   10                  15

<210> SEQ ID NO 295
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 295

Cys Ala Thr Trp Glu Arg Pro Gln Leu Tyr Tyr Lys Lys Leu Phe
1               5                   10                  15

<210> SEQ ID NO 296
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 296

Cys Ala Thr Trp Asn Arg Pro Gln Leu Tyr Tyr Lys Lys Leu Phe
1               5                   10                  15

<210> SEQ ID NO 297
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 297

Cys Ala Thr Trp Gln Arg Pro Gln Leu Tyr Tyr Lys Lys Leu Phe
1               5                   10                  15

<210> SEQ ID NO 298
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 298

Cys Ala Thr Trp Asp Lys Pro Gln Leu Tyr Tyr Lys Lys Leu Phe
1               5                   10                  15

<210> SEQ ID NO 299
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 299

Cys Ala Thr Trp Glu Lys Pro Gln Leu Tyr Tyr Lys Lys Leu Phe
1               5                   10                  15

<210> SEQ ID NO 300
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 300

Cys Ala Thr Trp Asn Lys Pro Gln Leu Tyr Tyr Lys Lys Leu Phe
1               5                   10                  15

<210> SEQ ID NO 301
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 301

Cys Ala Thr Trp Gln Lys Pro Gln Leu Tyr Tyr Lys Lys Leu Phe
1               5                   10                  15

<210> SEQ ID NO 302
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 302

Cys Ala Thr Trp Asp Arg Pro Glu Ile Phe Tyr Lys Lys Leu Phe
1               5                   10                  15

<210> SEQ ID NO 303
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 303

Cys Ala Thr Trp Glu Arg Pro Glu Ile Phe Tyr Lys Lys Leu Phe
1               5                   10                  15

<210> SEQ ID NO 304
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 304

Cys Ala Thr Trp Asn Arg Pro Glu Ile Phe Tyr Lys Lys Leu Phe
1               5                   10                  15

<210> SEQ ID NO 305
<211> LENGTH: 15
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 305

Cys Ala Thr Trp Gln Arg Pro Glu Ile Phe Tyr Lys Lys Leu Phe
1               5                   10                  15

<210> SEQ ID NO 306
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 306

Cys Ala Thr Trp Asp Lys Pro Glu Ile Phe Tyr Lys Lys Leu Phe
1               5                   10                  15

<210> SEQ ID NO 307
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 307

Cys Ala Thr Trp Glu Lys Pro Glu Ile Phe Tyr Lys Lys Leu Phe
1               5                   10                  15

<210> SEQ ID NO 308
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 308

Cys Ala Thr Trp Asn Lys Pro Glu Ile Phe Tyr Lys Lys Leu Phe
1               5                   10                  15

<210> SEQ ID NO 309
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 309

Cys Ala Thr Trp Gln Lys Pro Glu Ile Phe Tyr Lys Lys Leu Phe
1               5                   10                  15

<210> SEQ ID NO 310
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
```

```
                          Synthetic peptide"

<400> SEQUENCE: 310

Cys Ala Thr Trp Asp Arg Pro Asp Ile Phe Tyr Lys Lys Leu Phe
1               5                   10                  15

<210> SEQ ID NO 311
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 311

Cys Ala Thr Trp Glu Arg Pro Asp Ile Phe Tyr Lys Lys Leu Phe
1               5                   10                  15

<210> SEQ ID NO 312
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 312

Cys Ala Thr Trp Asn Arg Pro Asp Ile Phe Tyr Lys Lys Leu Phe
1               5                   10                  15

<210> SEQ ID NO 313
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 313

Cys Ala Thr Trp Gln Arg Pro Asp Ile Phe Tyr Lys Lys Leu Phe
1               5                   10                  15

<210> SEQ ID NO 314
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 314

Cys Ala Thr Trp Asp Lys Pro Asp Ile Phe Tyr Lys Lys Leu Phe
1               5                   10                  15

<210> SEQ ID NO 315
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 315
```

Cys Ala Thr Trp Glu Lys Pro Asp Ile Phe Tyr Lys Lys Leu Phe
1               5                   10                  15

<210> SEQ ID NO 316
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 316

Cys Ala Thr Trp Asn Lys Pro Asp Ile Phe Tyr Lys Lys Leu Phe
1               5                   10                  15

<210> SEQ ID NO 317
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 317

Cys Ala Thr Trp Gln Lys Pro Asp Ile Phe Tyr Lys Lys Leu Phe
1               5                   10                  15

<210> SEQ ID NO 318
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 318

Cys Ala Thr Trp Asp Arg Pro Asn Ile Phe Tyr Lys Lys Leu Phe
1               5                   10                  15

<210> SEQ ID NO 319
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 319

Cys Ala Thr Trp Glu Arg Pro Asn Ile Phe Tyr Lys Lys Leu Phe
1               5                   10                  15

<210> SEQ ID NO 320
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 320

Cys Ala Thr Trp Asn Arg Pro Asn Ile Phe Tyr Lys Lys Leu Phe
1               5                   10                  15

```
<210> SEQ ID NO 321
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 321

Cys Ala Thr Trp Gln Arg Pro Asn Ile Phe Tyr Lys Lys Leu Phe
1               5                   10                  15

<210> SEQ ID NO 322
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 322

Cys Ala Thr Trp Asp Lys Pro Asn Ile Phe Tyr Lys Lys Leu Phe
1               5                   10                  15

<210> SEQ ID NO 323
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 323

Cys Ala Thr Trp Glu Lys Pro Asn Ile Phe Tyr Lys Lys Leu Phe
1               5                   10                  15

<210> SEQ ID NO 324
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 324

Cys Ala Thr Trp Asn Lys Pro Asn Ile Phe Tyr Lys Lys Leu Phe
1               5                   10                  15

<210> SEQ ID NO 325
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 325

Cys Ala Thr Trp Gln Lys Pro Asn Ile Phe Tyr Lys Lys Leu Phe
1               5                   10                  15

<210> SEQ ID NO 326
<211> LENGTH: 15
<212> TYPE: PRT
<213> ORGANISM: Artificial Sequence
```

<220> FEATURE:
<221> NAME/KEY: source
<223> OTHER INFORMATION: /note="Description of Artificial Sequence:
      Synthetic peptide"

<400> SEQUENCE: 326

Cys Ala Thr Trp Asp Arg Pro Gln Ile Phe Tyr Lys Lys Leu Phe
1               5                   10                  15

<210> SEQ ID NO 327
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 327

Cys Ala Thr Trp Glu Arg Pro Gln Ile Phe Tyr Lys Lys Leu Phe
1               5                   10                  15

<210> SEQ ID NO 328
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 328

Cys Ala Thr Trp Asn Arg Pro Gln Ile Phe Tyr Lys Lys Leu Phe
1               5                   10                  15

<210> SEQ ID NO 329
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 329

Cys Ala Thr Trp Gln Arg Pro Gln Ile Phe Tyr Lys Lys Leu Phe
1               5                   10                  15

<210> SEQ ID NO 330
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 330

Cys Ala Thr Trp Asp Lys Pro Gln Ile Phe Tyr Lys Lys Leu Phe
1               5                   10                  15

<210> SEQ ID NO 331
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 331

Cys Ala Thr Trp Glu Lys Pro Gln Ile Phe Tyr Lys Lys Leu Phe
1               5                   10                  15

<210> SEQ ID NO 332
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 332

Cys Ala Thr Trp Asn Lys Pro Gln Ile Phe Tyr Lys Lys Leu Phe
1               5                   10                  15

<210> SEQ ID NO 333
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 333

Cys Ala Thr Trp Gln Lys Pro Gln Ile Phe Tyr Lys Lys Leu Phe
1               5                   10                  15

<210> SEQ ID NO 334
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 334

Cys Ala Thr Trp Asp Arg Pro Glu Leu Phe Tyr Lys Lys Leu Phe
1               5                   10                  15

<210> SEQ ID NO 335
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 335

Cys Ala Thr Trp Glu Arg Pro Glu Leu Phe Tyr Lys Lys Leu Phe
1               5                   10                  15

<210> SEQ ID NO 336
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 336

Cys Ala Thr Trp Asn Arg Pro Glu Leu Phe Tyr Lys Lys Leu Phe
```

```
1               5                   10                  15
```

<210> SEQ ID NO 337
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 337

```
Cys Ala Thr Trp Gln Arg Pro Glu Leu Phe Tyr Lys Lys Leu Phe
1               5                   10                  15
```

<210> SEQ ID NO 338
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 338

```
Cys Ala Thr Trp Asp Lys Pro Glu Leu Phe Tyr Lys Lys Leu Phe
1               5                   10                  15
```

<210> SEQ ID NO 339
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 339

```
Cys Ala Thr Trp Glu Lys Pro Glu Leu Phe Tyr Lys Lys Leu Phe
1               5                   10                  15
```

<210> SEQ ID NO 340
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 340

```
Cys Ala Thr Trp Asn Lys Pro Glu Leu Phe Tyr Lys Lys Leu Phe
1               5                   10                  15
```

<210> SEQ ID NO 341
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 341

```
Cys Ala Thr Trp Gln Lys Pro Glu Leu Phe Tyr Lys Lys Leu Phe
1               5                   10                  15
```

<210> SEQ ID NO 342

```
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 342

Cys Ala Thr Trp Asp Arg Pro Asp Leu Phe Tyr Lys Lys Leu Phe
1               5                   10                  15

<210> SEQ ID NO 343
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 343

Cys Ala Thr Trp Glu Arg Pro Asp Leu Phe Tyr Lys Lys Leu Phe
1               5                   10                  15

<210> SEQ ID NO 344
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 344

Cys Ala Thr Trp Asn Arg Pro Asp Leu Phe Tyr Lys Lys Leu Phe
1               5                   10                  15

<210> SEQ ID NO 345
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 345

Cys Ala Thr Trp Gln Arg Pro Asp Leu Phe Tyr Lys Lys Leu Phe
1               5                   10                  15

<210> SEQ ID NO 346
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 346

Cys Ala Thr Trp Asp Lys Pro Asp Leu Phe Tyr Lys Lys Leu Phe
1               5                   10                  15

<210> SEQ ID NO 347
<211> LENGTH: 15
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 347

Cys Ala Thr Trp Glu Lys Pro Asp Leu Phe Tyr Lys Lys Leu Phe
1               5                   10                  15

<210> SEQ ID NO 348
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 348

Cys Ala Thr Trp Asn Lys Pro Asp Leu Phe Tyr Lys Lys Leu Phe
1               5                   10                  15

<210> SEQ ID NO 349
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 349

Cys Ala Thr Trp Gln Lys Pro Asp Leu Phe Tyr Lys Lys Leu Phe
1               5                   10                  15

<210> SEQ ID NO 350
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 350

Cys Ala Thr Trp Asp Arg Pro Asn Leu Phe Tyr Lys Lys Leu Phe
1               5                   10                  15

<210> SEQ ID NO 351
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 351

Cys Ala Thr Trp Glu Arg Pro Asn Leu Phe Tyr Lys Lys Leu Phe
1               5                   10                  15

<210> SEQ ID NO 352
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 352

Cys Ala Thr Trp Asn Arg Pro Asn Leu Phe Tyr Lys Lys Leu Phe
1               5                   10                  15

<210> SEQ ID NO 353
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 353

Cys Ala Thr Trp Gln Arg Pro Asn Leu Phe Tyr Lys Lys Leu Phe
1               5                   10                  15

<210> SEQ ID NO 354
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 354

Cys Ala Thr Trp Asp Lys Pro Asn Leu Phe Tyr Lys Lys Leu Phe
1               5                   10                  15

<210> SEQ ID NO 355
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 355

Cys Ala Thr Trp Glu Lys Pro Asn Leu Phe Tyr Lys Lys Leu Phe
1               5                   10                  15

<210> SEQ ID NO 356
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 356

Cys Ala Thr Trp Asn Lys Pro Asn Leu Phe Tyr Lys Lys Leu Phe
1               5                   10                  15

<210> SEQ ID NO 357
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 357

Cys Ala Thr Trp Gln Lys Pro Asn Leu Phe Tyr Lys Lys Leu Phe
1               5                   10                  15
```

```
<210> SEQ ID NO 358
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 358

Cys Ala Thr Trp Asp Arg Pro Gln Leu Phe Tyr Lys Lys Leu Phe
1               5                   10                  15

<210> SEQ ID NO 359
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 359

Cys Ala Thr Trp Glu Arg Pro Gln Leu Phe Tyr Lys Lys Leu Phe
1               5                   10                  15

<210> SEQ ID NO 360
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 360

Cys Ala Thr Trp Asn Arg Pro Gln Leu Phe Tyr Lys Lys Leu Phe
1               5                   10                  15

<210> SEQ ID NO 361
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 361

Cys Ala Thr Trp Gln Arg Pro Gln Leu Phe Tyr Lys Lys Leu Phe
1               5                   10                  15

<210> SEQ ID NO 362
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 362

Cys Ala Thr Trp Asp Lys Pro Gln Leu Phe Tyr Lys Lys Leu Phe
1               5                   10                  15

<210> SEQ ID NO 363
<211> LENGTH: 15
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 363

Cys Ala Thr Trp Glu Lys Pro Gln Leu Phe Tyr Lys Lys Leu Phe
1               5                   10                  15

<210> SEQ ID NO 364
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 364

Cys Ala Thr Trp Asn Lys Pro Gln Leu Phe Tyr Lys Lys Leu Phe
1               5                   10                  15

<210> SEQ ID NO 365
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 365

Cys Ala Thr Trp Gln Lys Pro Gln Leu Phe Tyr Lys Lys Leu Phe
1               5                   10                  15

<210> SEQ ID NO 366
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 366

Cys Ala Thr Trp Glu Arg Pro Glu Val Phe Tyr Lys Lys Leu Phe
1               5                   10                  15

<210> SEQ ID NO 367
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 367

Cys Ala Thr Trp Asn Arg Pro Glu Val Phe Tyr Lys Lys Leu Phe
1               5                   10                  15

<210> SEQ ID NO 368
<211> LENGTH: 15
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 368

Cys Ala Thr Trp Gln Arg Pro Glu Val Phe Tyr Lys Lys Leu Phe
1               5                   10                  15

<210> SEQ ID NO 369
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 369

Cys Ala Thr Trp Asp Lys Pro Glu Val Phe Tyr Lys Lys Leu Phe
1               5                   10                  15

<210> SEQ ID NO 370
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 370

Cys Ala Thr Trp Glu Lys Pro Glu Val Phe Tyr Lys Lys Leu Phe
1               5                   10                  15

<210> SEQ ID NO 371
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 371

Cys Ala Thr Trp Asn Lys Pro Glu Val Phe Tyr Lys Lys Leu Phe
1               5                   10                  15

<210> SEQ ID NO 372
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 372

Cys Ala Thr Trp Gln Lys Pro Glu Val Phe Tyr Lys Lys Leu Phe
1               5                   10                  15

<210> SEQ ID NO 373
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 373
```

```
Cys Ala Thr Trp Asp Arg Pro Asp Val Phe Tyr Lys Lys Leu Phe
1               5                   10                  15

<210> SEQ ID NO 374
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 374

Cys Ala Thr Trp Glu Arg Pro Asp Val Phe Tyr Lys Lys Leu Phe
1               5                   10                  15

<210> SEQ ID NO 375
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 375

Cys Ala Thr Trp Asn Arg Pro Asp Val Phe Tyr Lys Lys Leu Phe
1               5                   10                  15

<210> SEQ ID NO 376
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 376

Cys Ala Thr Trp Gln Arg Pro Asp Val Phe Tyr Lys Lys Leu Phe
1               5                   10                  15

<210> SEQ ID NO 377
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 377

Cys Ala Thr Trp Asp Lys Pro Asp Val Phe Tyr Lys Lys Leu Phe
1               5                   10                  15

<210> SEQ ID NO 378
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 378

Cys Ala Thr Trp Glu Lys Pro Asp Val Phe Tyr Lys Lys Leu Phe
1               5                   10                  15
```

```
<210> SEQ ID NO 379
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 379

Cys Ala Thr Trp Asn Lys Pro Asp Val Phe Tyr Lys Lys Leu Phe
1               5                   10                  15

<210> SEQ ID NO 380
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 380

Cys Ala Thr Trp Gln Lys Pro Asp Val Phe Tyr Lys Lys Leu Phe
1               5                   10                  15

<210> SEQ ID NO 381
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 381

Cys Ala Thr Trp Asp Arg Pro Asn Val Phe Tyr Lys Lys Leu Phe
1               5                   10                  15

<210> SEQ ID NO 382
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 382

Cys Ala Thr Trp Glu Arg Pro Asn Val Phe Tyr Lys Lys Leu Phe
1               5                   10                  15

<210> SEQ ID NO 383
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 383

Cys Ala Thr Trp Asn Arg Pro Asn Val Phe Tyr Lys Lys Leu Phe
1               5                   10                  15

<210> SEQ ID NO 384
<211> LENGTH: 15
<212> TYPE: PRT
```

-continued

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 384

Cys Ala Thr Trp Gln Arg Pro Asn Val Phe Tyr Lys Lys Leu Phe
1               5                   10                  15

<210> SEQ ID NO 385
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 385

Cys Ala Thr Trp Asp Lys Pro Asn Val Phe Tyr Lys Lys Leu Phe
1               5                   10                  15

<210> SEQ ID NO 386
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 386

Cys Ala Thr Trp Glu Lys Pro Asn Val Phe Tyr Lys Lys Leu Phe
1               5                   10                  15

<210> SEQ ID NO 387
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 387

Cys Ala Thr Trp Asn Lys Pro Asn Val Phe Tyr Lys Lys Leu Phe
1               5                   10                  15

<210> SEQ ID NO 388
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 388

Cys Ala Thr Trp Gln Lys Pro Asn Val Phe Tyr Lys Lys Leu Phe
1               5                   10                  15

<210> SEQ ID NO 389
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 389

Cys Ala Thr Trp Asp Arg Pro Gln Val Phe Tyr Lys Lys Leu Phe
1               5                   10                  15

<210> SEQ ID NO 390
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 390

Cys Ala Thr Trp Glu Arg Pro Gln Val Phe Tyr Lys Lys Leu Phe
1               5                   10                  15

<210> SEQ ID NO 391
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 391

Cys Ala Thr Trp Asn Arg Pro Gln Val Phe Tyr Lys Lys Leu Phe
1               5                   10                  15

<210> SEQ ID NO 392
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 392

Cys Ala Thr Trp Gln Arg Pro Gln Val Phe Tyr Lys Lys Leu Phe
1               5                   10                  15

<210> SEQ ID NO 393
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 393

Cys Ala Thr Trp Asp Lys Pro Gln Val Phe Tyr Lys Lys Leu Phe
1               5                   10                  15

<210> SEQ ID NO 394
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 394

```
Cys Ala Thr Trp Glu Lys Pro Gln Val Phe Tyr Lys Lys Leu Phe
1               5                   10                  15
```

<210> SEQ ID NO 395
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 395

```
Cys Ala Thr Trp Asn Lys Pro Gln Val Phe Tyr Lys Lys Leu Phe
1               5                   10                  15
```

<210> SEQ ID NO 396
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 396

```
Cys Ala Thr Trp Gln Lys Pro Gln Val Phe Tyr Lys Lys Leu Phe
1               5                   10                  15
```

<210> SEQ ID NO 397
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 397

```
Cys Ala Thr Trp Glu Arg Pro Glu Val Tyr Tyr Lys Lys Leu Phe
1               5                   10                  15
```

<210> SEQ ID NO 398
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 398

```
Cys Ala Thr Trp Asn Arg Pro Glu Val Tyr Tyr Lys Lys Leu Phe
1               5                   10                  15
```

<210> SEQ ID NO 399
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 399

```
Cys Ala Thr Trp Gln Arg Pro Glu Val Tyr Tyr Lys Lys Leu Phe
1               5                   10                  15
```

```
<210> SEQ ID NO 400
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 400

Cys Ala Thr Trp Asp Lys Pro Glu Val Tyr Tyr Lys Lys Leu Phe
1               5                   10                  15

<210> SEQ ID NO 401
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 401

Cys Ala Thr Trp Glu Lys Pro Glu Val Tyr Tyr Lys Lys Leu Phe
1               5                   10                  15

<210> SEQ ID NO 402
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 402

Cys Ala Thr Trp Asn Lys Pro Glu Val Tyr Tyr Lys Lys Leu Phe
1               5                   10                  15

<210> SEQ ID NO 403
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 403

Cys Ala Thr Trp Gln Lys Pro Glu Val Tyr Tyr Lys Lys Leu Phe
1               5                   10                  15

<210> SEQ ID NO 404
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 404

Cys Ala Thr Trp Asp Arg Pro Asp Val Tyr Tyr Lys Lys Leu Phe
1               5                   10                  15

<210> SEQ ID NO 405
<211> LENGTH: 15
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 405

Cys Ala Thr Trp Glu Arg Pro Asp Val Tyr Tyr Lys Lys Leu Phe
1               5                   10                  15

<210> SEQ ID NO 406
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 406

Cys Ala Thr Trp Asn Arg Pro Asp Val Tyr Tyr Lys Lys Leu Phe
1               5                   10                  15

<210> SEQ ID NO 407
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 407

Cys Ala Thr Trp Gln Arg Pro Asp Val Tyr Tyr Lys Lys Leu Phe
1               5                   10                  15

<210> SEQ ID NO 408
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 408

Cys Ala Thr Trp Asp Lys Pro Asp Val Tyr Tyr Lys Lys Leu Phe
1               5                   10                  15

<210> SEQ ID NO 409
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 409

Cys Ala Thr Trp Glu Lys Pro Asp Val Tyr Tyr Lys Lys Leu Phe
1               5                   10                  15

<210> SEQ ID NO 410
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 410

Cys Ala Thr Trp Asn Lys Pro Asp Val Tyr Tyr Lys Lys Leu Phe
1               5                   10                  15

<210> SEQ ID NO 411
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 411

Cys Ala Thr Trp Gln Lys Pro Asp Val Tyr Tyr Lys Lys Leu Phe
1               5                   10                  15

<210> SEQ ID NO 412
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 412

Cys Ala Thr Trp Asp Arg Pro Asn Val Tyr Tyr Lys Lys Leu Phe
1               5                   10                  15

<210> SEQ ID NO 413
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 413

Cys Ala Thr Trp Glu Arg Pro Asn Val Tyr Tyr Lys Lys Leu Phe
1               5                   10                  15

<210> SEQ ID NO 414
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 414

Cys Ala Thr Trp Asn Arg Pro Asn Val Tyr Tyr Lys Lys Leu Phe
1               5                   10                  15

<210> SEQ ID NO 415
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 415

Cys Ala Thr Trp Gln Arg Pro Asn Val Tyr Tyr Lys Lys Leu Phe

```
1               5                   10                  15
```

<210> SEQ ID NO 416
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 416

```
Cys Ala Thr Trp Asp Lys Pro Asn Val Tyr Tyr Lys Lys Leu Phe
1               5                   10                  15
```

<210> SEQ ID NO 417
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 417

```
Cys Ala Thr Trp Glu Lys Pro Asn Val Tyr Tyr Lys Lys Leu Phe
1               5                   10                  15
```

<210> SEQ ID NO 418
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 418

```
Cys Ala Thr Trp Asn Lys Pro Asn Val Tyr Tyr Lys Lys Leu Phe
1               5                   10                  15
```

<210> SEQ ID NO 419
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 419

```
Cys Ala Thr Trp Gln Lys Pro Asn Val Tyr Tyr Lys Lys Leu Phe
1               5                   10                  15
```

<210> SEQ ID NO 420
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 420

```
Cys Ala Thr Trp Asp Arg Pro Gln Val Tyr Tyr Lys Lys Leu Phe
1               5                   10                  15
```

<210> SEQ ID NO 421

```
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 421

Cys Ala Thr Trp Glu Arg Pro Gln Val Tyr Tyr Lys Lys Leu Phe
1               5                   10                  15

<210> SEQ ID NO 422
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 422

Cys Ala Thr Trp Asn Arg Pro Gln Val Tyr Tyr Lys Lys Leu Phe
1               5                   10                  15

<210> SEQ ID NO 423
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 423

Cys Ala Thr Trp Gln Arg Pro Gln Val Tyr Tyr Lys Lys Leu Phe
1               5                   10                  15

<210> SEQ ID NO 424
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 424

Cys Ala Thr Trp Asp Lys Pro Gln Val Tyr Tyr Lys Lys Leu Phe
1               5                   10                  15

<210> SEQ ID NO 425
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 425

Cys Ala Thr Trp Glu Lys Pro Gln Val Tyr Tyr Lys Lys Leu Phe
1               5                   10                  15

<210> SEQ ID NO 426
<211> LENGTH: 15
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 426

Cys Ala Thr Trp Asn Lys Pro Gln Val Tyr Tyr Lys Lys Leu Phe
1               5                   10                  15

<210> SEQ ID NO 427
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 427

Cys Ala Thr Trp Gln Lys Pro Gln Val Tyr Tyr Lys Lys Leu Phe
1               5                   10                  15

<210> SEQ ID NO 428
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 428

Ala Thr Trp Asp Arg Pro Glu Ile Tyr Tyr Lys Lys Leu
1               5                   10

<210> SEQ ID NO 429
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 429
gatcaagtgt ggcccagaag                                           20

<210> SEQ ID NO 430
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 430
ctgccagtca gaaatcttcc                                           20

<210> SEQ ID NO 431
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 431
```
ttcaccagac aagcgaca                                                  18

<210> SEQ ID NO 432
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 432
ggggaaacat ctgcatca                                                  18

<210> SEQ ID NO 433
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 433

Ser Leu Leu Met Trp Ile Thr Gln Val
1               5

<210> SEQ ID NO 434
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 434

Gln Tyr Asp Pro Val Ala Ala Leu Phe
1               5

<210> SEQ ID NO 435
<211> LENGTH: 9
<212> TYPE: PRT
<213> ORGANISM: Homo sapiens

<400> SEQUENCE: 435

Arg Met Phe Pro Asn Ala Pro Tyr Leu
1               5

<210> SEQ ID NO 436
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 436
gagtagcgcg agcacagcta                                                20

<210> SEQ ID NO 437
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 437
ggagcgcacc atcttcttca            20

<210> SEQ ID NO 438
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 438

Arg Tyr Pro Leu Thr Phe Gly Trp Cys Phe
1               5                   10

<210> SEQ ID NO 439
<211> LENGTH: 350
<212> TYPE: PRT
<213> ORGANISM: Homo sapiens

<400> SEQUENCE: 439

Met Ala Val Met Ala Pro Arg Thr Leu Val Leu Leu Leu Ser Gly Ala
1               5                   10                  15

Leu Ala Leu Thr Gln Thr Trp Ala Gly Ser His Ser Met Arg Tyr Phe
            20                  25                  30

Phe Thr Ser Val Ser Arg Pro Gly Arg Gly Glu Pro Arg Phe Ile Ala
        35                  40                  45

Val Gly Tyr Val Asp Asp Thr Gln Phe Val Arg Phe Asp Ser Asp Ala
    50                  55                  60

Ala Ser Gln Arg Met Glu Pro Arg Ala Pro Trp Ile Glu Gln Glu Gly
65                  70                  75                  80

Pro Glu Tyr Trp Asp Gly Glu Thr Arg Lys Val Lys Ala His Ser Gln
                85                  90                  95

Thr His Arg Val Asp Leu Gly Thr Leu Arg Gly Tyr Tyr Asn Gln Ser
            100                 105                 110

Glu Ala Gly Ser His Thr Val Gln Arg Met Tyr Gly Cys Asp Val Gly
        115                 120                 125

Ser Asp Trp Arg Phe Leu Arg Gly Tyr His Gln Tyr Ala Tyr Asp Gly
    130                 135                 140

Lys Asp Tyr Ile Ala Leu Lys Glu Asp Leu Arg Ser Trp Thr Ala Ala
145                 150                 155                 160

Asp Met Ala Ala Gln Thr Thr Lys His Lys Trp Glu Ala Ala His Val
                165                 170                 175

Ala Glu Gln Leu Arg Ala Tyr Leu Glu Gly Thr Cys Val Glu Trp Leu
            180                 185                 190

Arg Arg Tyr Leu Glu Asn Gly Lys Glu Thr Leu Gln Arg Thr Asp Ala
        195                 200                 205

Pro Lys Thr His Met Thr His His Ala Val Ser Asp His Glu Ala Thr
    210                 215                 220

Leu Arg Cys Trp Ala Leu Ser Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
            260                 265                 270

```
Val Pro Ser Gly Gln Glu Gln Arg Tyr Thr Cys His Val Gln His Glu
        275                 280                 285

Gly Leu Pro Lys Pro Leu Thr Leu Arg Trp Glu Pro Ser Ser Gln Pro
        290                 295                 300

Thr Ile Pro Ile Val Gly Ile Ile Ala Gly Leu Val Leu Phe Gly Ala
305                 310                 315                 320

Val Ile Thr Gly Ala Val Val Ala Ala Val Met Trp Arg Arg Lys Ser
                325                 330                 335

Ser Asp Arg Lys Gly Gly Ser Tyr Ser Gln Ala Ala Ser Ser
                340                 345                 350

<210> SEQ ID NO 440
<211> LENGTH: 350
<212> TYPE: PRT
<213> ORGANISM: Homo sapiens

<400> SEQUENCE: 440

Met Ala Val Met Ala Pro Arg Thr Leu Val Leu Leu Leu Ser Gly Ala
1               5                   10                  15

Leu Ala Leu Thr Gln Thr Trp Ala Gly Ser His Ser Met Arg Tyr Phe
                20                  25                  30

Ser Thr Ser Val Ser Arg Pro Gly Arg Gly Glu Pro Arg Phe Ile Ala
        35                  40                  45

Val Gly Tyr Val Asp Asp Thr Gln Phe Val Arg Phe Asp Ser Asp Ala
    50                  55                  60

Ala Ser Gln Arg Met Glu Pro Arg Ala Pro Trp Ile Glu Gln Glu Gly
65                  70                  75                  80

Pro Glu Tyr Trp Asp Glu Glu Thr Gly Lys Val Lys Ala His Ser Gln
                85                  90                  95

Thr Asp Arg Glu Asn Leu Arg Ile Ala Leu Arg Tyr Tyr Asn Gln Ser
            100                 105                 110

Glu Ala Gly Ser His Thr Leu Gln Met Met Phe Gly Cys Asp Val Gly
        115                 120                 125

Ser Asp Gly Arg Phe Leu Arg Gly Tyr His Gln Tyr Ala Tyr Asp Gly
    130                 135                 140

Lys Asp Tyr Ile Ala Leu Lys Glu Asp Leu Arg Ser Trp Thr Ala Ala
145                 150                 155                 160

Asp Met Ala Ala Gln Ile Thr Lys Arg Lys Trp Glu Ala Ala His Val
                165                 170                 175

Ala Glu Gln Gln Arg Ala Tyr Leu Glu Gly Thr Cys Val Asp Gly Leu
            180                 185                 190

Arg Arg Tyr Leu Glu Asn Gly Lys Glu Thr Leu Gln Arg Thr Asp Pro
        195                 200                 205

Pro Lys Thr His Met Thr His His Pro Ile Ser Asp His Glu Ala Thr
    210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Glu Pro Ser Ser Gln Pro
```

```
                290             295             300
Thr Val Pro Ile Val Gly Ile Ile Ala Gly Leu Val Leu Gly Ala
305                 310             315             320

Val Ile Thr Gly Ala Val Val Ala Ala Val Met Trp Arg Arg Asn Ser
                325             330             335

Ser Asp Arg Lys Gly Gly Ser Tyr Ser Gln Ala Ala Ser Ser
            340             345             350

<210> SEQ ID NO 441
<211> LENGTH: 30
<212> TYPE: PRT
<213> ORGANISM: Homo sapiens

<400> SEQUENCE: 441

His Val Ala Glu Gln Gln Arg Ala Tyr Leu Glu Gly Thr Cys Val Asp
1               5                   10                  15

Gly Leu Arg Arg Tyr Leu Glu Asn Gly Lys Glu Thr Leu Gln
            20                  25                  30

<210> SEQ ID NO 442
<211> LENGTH: 30
<212> TYPE: PRT
<213> ORGANISM: Homo sapiens

<400> SEQUENCE: 442

His Val Ala Glu Gln Leu Arg Ala Tyr Leu Glu Gly Thr Cys Val Glu
1               5                   10                  15

Trp Leu Arg Arg Tyr Leu Glu Asn Gly Lys Glu Thr Leu Gln
            20                  25                  30

<210> SEQ ID NO 443
<211> LENGTH: 30
<212> TYPE: PRT
<213> ORGANISM: Homo sapiens

<400> SEQUENCE: 443

His Val Ala Glu Gln Gln Arg Ala Tyr Leu Glu Gly Thr Cys Val Glu
1               5                   10                  15

Trp Leu Arg Arg Tyr Leu Glu Asn Gly Lys Glu Thr Leu Gln
            20                  25                  30

<210> SEQ ID NO 444
<211> LENGTH: 30
<212> TYPE: PRT
<213> ORGANISM: Homo sapiens

<400> SEQUENCE: 444

His Glu Ala Glu Gln Trp Arg Ala Tyr Leu Glu Gly Arg Cys Val Glu
1               5                   10                  15

Trp Leu Arg Arg Tyr Leu Glu Asn Gly Lys Glu Thr Leu Gln
            20                  25                  30
```